United States Patent [19]
Lok et al.

[11] Patent Number: 5,945,511
[45] Date of Patent: Aug. 31, 1999

[54] CLASS II CYTOKINE RECEPTOR

[75] Inventors: Si Lok, Seattle, Wash.; Choon J. Kho, Singapore, Singapore; Anna C. Jelmberg, Issaquah, Wash.; Robyn L Adams, Bellevue, Wash.; Theodore E. Whitmore, Redmond, Wash.; Theresa M. Farrah, Seattle, Wash.

[73] Assignee: ZymoGenetics, Inc., Seattle, Wash.

[21] Appl. No.: 08/943,087

[22] Filed: Oct. 2, 1997

Related U.S. Application Data

[63] Continuation-in-part of application No. 08/803,305, Feb. 20, 1997, abandoned.
[51] Int. Cl.[6] .................................................. C07K 1/00
[52] U.S. Cl. ..................... 530/350; 530/351; 530/395; 424/85.1; 514/2; 435/69.1; 435/69.5; 930/120; 930/140; 536/235
[58] Field of Search ..................... 530/350, 351; 424/85.1; 930/120, 140

[56] References Cited

PUBLICATIONS

Hillier et al., The Wash U–Merck EST Project, 1995.
LIFESEQ™ Clone Information Results, Incyte Pharmaceuticals, Inc., 1996.
LIFESEQ™ Clone Information Results, Incyte Pharmaceuticals, Inc., 1995.

*Primary Examiner*—Garnette D. Draper
*Attorney, Agent, or Firm*—Paul G. Lunn, Esq.

[57] ABSTRACT

Novel receptor polypeptides, polynucleotides encoding the polypeptides, and related compositions and methods are disclosed. The polypeptides comprise an extracellular domain of a cell-surface receptor that is expressed in kidneys, pancreas, prostate, adrenal cortex and nervous tissue. The polypeptides may be used within methods for detecting ligands that promote the proliferation and/or differentiation of these organs.

4 Claims, No Drawings

CLASS II CYTOKINE RECEPTOR

The present application is a continuation-in-part of U.S. patent application Ser. No. 08/803,305 filed Feb. 20, 1997 now abandoned.

BACKGROUND OF THE INVENTION

Cytokines are soluble proteins that influence the growth and differentiation of many cell types. Their receptors are composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons (IFNs) are members of the type II cytokine receptor family (CRF2), based upon a characteristic 200 residue extracellular domain. The demonstrated in vivo activities of these interferons illustrate the enormous clinical potential of, and need for, other cytokines, cytokine agonists, and cytokine antagonists.

SUMMARY OF THE INVENTION

The present invention fills this need by providing novel cytokine receptors and related compositions and methods. In particular, the present invention provides for an extracellular ligand-binding region of a mammalian Zcytor7 receptor, alternatively also containing either a transmembrane domain or both an intracellular domain and a transmembrane domain.

Within one aspect, the present invention provides an isolated polynucleotide encoding a ligand-binding receptor polypeptide. The polypeptide comprises a sequence of amino acids selected from the group consisting of (a) residues 30 through 250 of SEQ ID NO:2; (b) allelic variants of (a); and (c) sequences that are at least 80% identical to (a) or (b). Within one embodiment, the polypeptide comprises residues 30 through 250 of SEQ ID NO:2. Within another embodiment, the polypeptide encoded by the isolated polynucleotide further comprises a transmembrane domain. The transmembrane domain may comprise residues 251 through 274 of SEQ ID NO:2, or an allelic variant thereof. Within another embodiment, the polypeptide encoded by the isolated polynucleotide further comprises an intracellular domain, such as an intracellular domain comprising residues 275 through 553 of SEQ ID NO:2, or an allelic variant thereof. Within further embodiments, the polynucleotide encodes a polypeptide that comprises residues 1 through 553, 1 through 274, 1 through 250, 30 through 274 or 30 through 553 of SEQ ID NO:2. Within an additional embodiment, the polypeptide further comprises an affinity tag. Within a further embodiment, the polynucleotide is DNA. Also claimed are the isolated polypeptides encoded by these polynucleotides.

Within a second aspect of the invention there is provided an expression vector comprising (a) a transcription promoter; (b) a DNA segment encoding a ligand-binding receptor polypeptide, wherein the ligand-binding receptor polypeptide comprises a sequence of amino acids selected from the group consisting of: (i) residues 30 through 250 of SEQ ID NO:2; (ii) allelic variants of (i); and (iii) sequences that are at least 80% identical to (i) or (ii); and (c) a transcription terminator, wherein the promoter, DNA segment, and terminator are operably linked. The ligand-binding receptor polypeptide may further comprise a secre-tory peptide, a transmembrane domain, a transmembrane domain and an intracellular domain, or a secretory peptide, a transmembrane domain and an intracellular domain.

Within a third aspect of the invention there is provided a cultured eukaryotic cell into which has been introduced an expression vector as disclosed above, wherein said cell expresses a receptor polypeptide encoded by the DNA segment. Within one embodiment, the cell further expresses a necessary receptor subunit which forms a functional receptor complex. Within another embodiment, the cell is dependent upon an exogenously supplied hematopoietic growth factor for proliferation.

Within a fourth aspect of the invention there is provided an isolated polypeptide comprising a sequence selected from the group consisting of (a) residues 30, a valine, through residue 250, a lysine, of SEQ ID NO:2; (b) allelic variants of (a); and (c) sequences that are at least 80% identical to (a) or (b), wherein said polypeptide is substantially free of transmembrane and intracellular domains ordinarily associated with hematopoietic receptors. Also claimed are polypeptides comprised of a sequence defined by residues 30, a valine, through residue 274, a tyrosine; and a polypeptide comprised of a sequence defined by residues 30, a valine, through residue 553 an asparagine. Also claimed are the polypeptides and polynucleotides defined by the sequences of SEQ ID NOs: 13–60.

Within a further aspect of the invention there is provided a chimeric polypeptide consisting essentially of a first portion and a second portion joined by a peptide bond. The first portion of the chimeric polypeptide consists essentially of a ligand binding domain of a receptor polypeptide selected from the group consisting of (a) a receptor polypeptide as shown in SEQ ID NO:2; (b) allelic variants of SEQ ID NO:2; and (c) receptor polypeptides that are at least 80% identical to (a) or (b). The second portion of the chimeric polypeptide consists essentially of an affinity tag. Within one embodiment the affinity tag is an immunoglobulin $F_c$ polypeptide. The invention also provides expression vectors encoding the chimeric polypeptides and host cells transfected to produce the chimeric polypeptides.

The present invention also provides for an isolated polynucleotide encoding a polypeptide selected from a group defined SEQ ID NO:2 consisting of residues 1 through 250, residues 1 through 274, residues 1 through 553, residues 2 through 250, residues 2 through 274, residues 2 through 553, residues 251 through 274, residues 251 through 553 and residues 275 through 553. Also claimed are the isolated polypeptide expressed by these polynucleotides.

The invention also provides a method for detecting a ligand within a test sample, comprising contacting a test sample with a polypeptide as disclosed above, and detecting binding of the polypeptide to ligand in the sample. Within one embodiment the polypeptide further comprises transmembrane and intracellular domains. The polypeptide can be membrane bound within a cultured cell, wherein the detecting step comprises measuring a biological response in the cultured cell. Within another embodiment, the polypeptide is immobilized on a solid support.

Within an additional aspect of the invention there is provided an antibody that specifically binds to a polypeptide as disclosed above, as well as an anti-idiotypic antibody which binds to the antigen-binding region of an antibody to Zcytor7.

In still another aspect of the present invention, polynucleotide primers and probes are provided which can detect mutations in the Zcytor7 gene. The polynucleotide probe should at least be 20–25 bases in length, preferably at least 50 bases in length and most preferably about 80 to 100 bases in length. In addition to the detection of mutations, these probes can be used to discover the Zcytor7 gene in other mammalian species. The probes can either be positive strand or anti-sense strands, and they can be comprised of DNA or RNA.

These and other aspects of the invention will become evident upon reference to the following detailed description and the attached drawing.

DETAILED DESCRIPTION OF THE INVENTION

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The present invention is based in part upon the discovery of a novel DNA sequence that encodes a protein having the structure of a cytokine receptor, including the conserved WSXWS motif (SEQ ID NO:10). Analysis of the tissue distribution of the mRNA corresponding to this novel DNA showed that mRNA level was highest in pancreas, prostate, kidney and adrenal cortex followed by lower levels in testis, stomach, adrenal medulla and thymus. The receptor has been designated "Zcytor7".

Cytokine receptors subunits are characterized by a multi-domain structure comprising a ligand-binding domain and an effector domain that is typically involved in signal transduction. Multimeric cytokine receptors include homodimers (e.g., PDGF receptor $\alpha\alpha$ and $\beta\beta$ isoforms, erythropoietin receptor, MPL [thrombopoietin receptor], and G-CSF receptor), heterodimers whose subunits each have ligand-binding and effector domains (e.g., PDGF receptor $\alpha\beta$ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Class I hematopoietic receptors, for example, are characterized by the presence of a domain containing conserved cysteine residues and the WSXWS motif (SEQ ID NO:10). Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, *Ann. Reports Med. Chem.* 26:221–228, 1991 and Cosman, *Cytokine* 5:95–106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Cell-surface cytokine receptors are further characterized by the presence of additional domains. These receptors are anchored in the cell membrane by a transmembrane domain characterized by a sequence of hydrophobic amino acid residues (typically about 21–25 residues), which is commonly flanked by positively charged residues (Lys or Arg). On the opposite end of the protein from the extracellular domain and separated from it by the transmembrane domain is an intracellular domain.

The novel receptor of the present invention, Zcytor7, is a class II cytokine receptor. These receptors usually bind to four-helix-bundle cytokines. Interleukin-10 and the interferons have receptors in this class (e.g., interferon-gamma alpha and beta chains and the interferon-alpha/beta receptor alpha and beta chains). Class II cytokine receptors are characterized by the presence of one or more cytokine receptor modules (CRM) in their extracellular domains. The CRMs of class II cytokine receptors are somewhat different than the better known CRMs of class I cytokine receptors. While the class II CRMs contain two type-III fibronectin-like domains, they differ in organization. In particular, they contain two WSXWS (SEQ ID NO: 10) motifs, one in each fibronectin III-like domain. These WSXWS (SEQ ID NO: 10) motifs, however, are less conserved than those found in class I CRMs.

Zcytor7, like all known class II receptors except interferon-alpha/beta receptor alpha chain, has only a single class II CRM in its extracellular domain. Zcytor7 appears to be a receptor for a helical cytokine of the interferon/IL-10 class. Using the Zcytor7 receptor we can identify ligands and additional compounds which would be of significant therapeutic value. Furthermore, the extracellular portion of Zcytor7 extending from residue 30, a valine, through residue 250 of SEQ ID NO: 2 can be expressed and used as a soluble receptor to down-regulate the effects of the ligand of Zcytor7.

As was stated above, Zcytor7 was initially identified by the overall homology to CRF2-4, an orphan Class II cytokine receptor. See Lutfalla G. et al. *Genomics,* 16:366–373 (1993). Analysis of a human cDNA clone encoding Zcytor7 (SEQ ID NO:1) revealed an open reading frame encoding 553 amino acids (SEQ ID NO:2) comprising an extracellular ligand-binding domain of approximately 221 amino acid residues (residues 30–250 of SEQ ID NO:2), a transmembrane domain of approximately 24 amino acid residues (residues 251–274 of SEQ ID NO:2), and an intracellular domain of approximately 279 amino acid residues (residues 275–553 of SEQ ID NO:2). Those skilled in the art will recognize that these domain boundaries are approximate and are based on alignments with known proteins and predictions of protein folding. Deletion of residues from the ends of the domains is possible.

Within preferred embodiments of the invention the isolated polynucleotides will hybridize to similar sized regions of SEQ ID NO:1 or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C. As previously noted, the isolated polynucleotides of the present invention include DNA and RNA. Methods for isolating DNA and RNA are well known in the art. It is generally preferred to isolate RNA from pancreas or prostate tissues although cDNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. Polynucleotides encoding ZCytor7 polypeptides are then identified and isolated by, for example, hybridization or PCR.

Those skilled in the art will recognize that the sequences disclosed in SEQ ID NOS:1 and 2 represent single alleles of the human ZCytor7 receptor. Allelic variants of these sequences can be cloned by probing cDNA or genomic libraries from different individuals according to standard procedures. Other specific embodiments include the polynucleotides and polypeptides defined by SEQ ID NOS: 13–60.

The present invention further provides counterpart receptors and polynucleotides from other species ("species orthologs"). Of particular interest are ZCytor7 receptors from other mammalian species, including murine, porcine, ovine, bovine, canine, feline, equine, and other primate receptors. Species orthologs of the human ZCytor7 receptor can be cloned using information and compositions provided by the present invention in combination with conventional cloning techniques. For example, a cDNA can be cloned using mRNA obtained from a tissue or cell type that expresses the receptor. Suitable sources of mRNA can be identified by probing Northern blots with probes designed from the sequences disclosed herein. A library is then prepared from mRNA of a positive tissue or cell line. A receptor-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the receptor. Similar techniques can also be applied to the isolation of genomic clones.

The present invention also provides isolated receptor polypeptides that are substantially homologous to the receptor polypeptide of SEQ ID NO: 2. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NO:2,. Such polypeptides will more preferably be at least 90% identical, and most preferably 95% or more identical to SEQ ID NO:2. Percent sequence identity is determined by conventional methods. See, for example, Altschul et al., *Bull. Math. Bio.* 48:603–616, 1986 and Henikoff and Henikoff, *Proc. Natl. Acad. Sci. USA*

89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide. Also claimedmall deletions of SEQ ID NO:2, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), or other antigenic epitope or binding domain. See, in general Ford et al., *Protein Expression and Purification* 2:95–107, 1991. DNAs encoding affinity tags are available from commercial suppliers (e.g., Pharmacia Biotech, Piscataway, N.J.).

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |

TABLE 2-continued

Conservative amino acid substitutions

| | |
|---|---|
| Small: | glycine |
| | alanine |
| | serine |
| | threonine |
| | methionine |

Essential amino acids in the receptor polypeptides of the present invention can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related receptors.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988)

Mutagenesis methods as disclosed above can be combined with high-throughput screening methods to detect activity of cloned, mutagenized receptors in host cells. Preferred assays in this regard include cell proliferation assays and biosensor-based ligand-binding assays, which are described below. Mutagenized DNA molecules that encode active receptors or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 30 to 250 of SEQ ID NO:2 or allelic variants thereof and retain the ligand-binding properties of the wild-type receptor. Such polypeptides may include additional amino acids from an extracellular ligand-binding domain of a Zcytor7 receptor as well as part or all of the transmembrane and intracellular domains. Such polypeptides may also include additional polypeptide segments as generally disclosed above.

Polynucleotides, generally a cDNA sequence, of the present invention encode the above-described polypeptides. A cDNA sequence which encodes a polypeptide of the present invention is comprised of a series of codons, each amino acid residue of the polypeptide being encoded by a codon and each codon being comprised of three nucleotides. The amino acid residues are encoded their respective codons as follows.

Alanine (Ala) is encoded by GCA, GCC, GCG or GCT;

Cysteine (Cys) is encoded by TGC or TGT;

Aspartic acid (Asp) is encoded by GAC or GAT;

Glutamic acid (Glu) is encoded by GAA or GAG;

Phenylalanine (Phe) is encoded by TTC or TTT;

Glycine (Gly) is encoded by GGA, GGC, GGG or GGT;

Histidine (His) is encoded by CAC or CAT;

Isoleucine (Ile) is encoded by ATA, ATC or ATT;

Lysine (Lys) is encoded by AAA, or AAG;

Leucine (Leu) is encoded by TTA, TTG, CTA, CTC, CTG or CTT;

Methionine (Met) is encoded by ATG;

Asparagine (Asn) is encoded by AAC or AAT;

Proline (Pro) is encoded by CCA, CCC, CCG or CCT;

Glutamine (Gln) is encoded by CAA or CAG;

Arginine (Arg) is encoded by AGA, AGG, CGA, CGC, CGG or CGT;

Serine (Ser) is encoded by AGC, AGT, TCA, TCC, TCG or TCT;

Threonine (Thr) is encoded by ACA, ACC, ACG or ACT;

Valine (Val) is encoded by GTA, GTC, GTG or GTT;

Tryptophan (Trp) is encoded by TGG; and

Tyrosine (Tyr) is encoded by TAC or TAT.

It is to be recognized that according to the present invention, when a cDNA is claimed as described above, it is understood that what is claimed are both the sense strand, the anti-sense strand, and the DNA as double-stranded having both the sense and anti-sense strand annealed together by their respective hydrogen bonds. Also claimed is the messenger RNA (mRNA) encodes the polypeptides of the present invention, and which mRNA is encoded by the above the above-described cDNA. A messenger RNA (mRNA) will encode a polypeptide using the same codons as those defined above, with the exception that each thymine nucleotide (T) is replaced by a uracil nucleotide (U).

The receptor polypeptides of the present invention, including full-length receptors, receptor fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., ibid.

The polynucleotides of the present invention can be synthesized using gene machines. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. The sequences of the strands are planned so that, after annealing, the two end segments of the gene are aligned to give blunt ends. Each internal section of the gene has complementary 3' and 5' terminal extensions that are designed to base pair precisely with an adjacent section. Thus, after the gene is assembled, the only remaining requirement to complete the process is sealing the nicks along the backbones of the two strands with T4 DNA ligase. In addition to the protein coding sequence, synthetic genes can be designed with terminal sequences that facilitate insertion into a restriction endonuclease sites of a cloning vector and other sequences should also be added that contain signals for the proper initiation and termination of transcription and translation.

An alternative way to prepare a full-size gene is to synthesize a specified set of overlapping oligonucleotides (40 to 100 nucleotides). After the 3' and 5' extensions (6 to 10 nucleotides) are annealed, large gaps still remain, but the base-paired regions are both long enough and stable enough to hold the structure together. The duplex is completed and the gaps filled by enzymatic DNA synthesis with *E. coli* DNA polymerase I. This enzyme uses the 3'-hydroxyl groups as replication initiation points and the single-stranded regions as templates. After the enzymatic synthesis is completed, the nicks are sealed with T4 DNA ligase. For larger genes ($\geq 1,000$ base pairs), the complete gene sequence is usually assembled from double-stranded fragments that are each put together by joining four to six overlapping oligonucleotides (20 to 60 bp each). If there is a sufficient amount of the double-stranded fragments after each synthesis and annealing step, they are simply joined to one another. Otherwise, each fragment is cloned into a vector to amplify the amount of DNA available. In both cases, the double-stranded constructs are sequentially linked to one another to form the entire gene sequence. Because it is absolutely essential that a chemically synthesized gene have the correct sequence of nucleotides, each double-stranded fragment and then the complete sequence is characterized by DNA sequence analysis. See Glick, Bernard R. and Jack J. Pasternak, *Molecular Biotechnology, Principles & Applications of Recombinant DNA*, (ASM Press, Washington, D.C. 1994), Itakura, K. et al. Synthesis and use of synthetic oligonucleotides. *Annu. Rev. Biochem.* 53:323–356 (1984), and Climie, S. et al. Chemical synthesis of the thymidylate synthase gene. *Proc. Natl. Acad. Sci. USA* 87:633–637 (1990).

A DNA sequence encoding a ZCytor7 receptor polypeptide can then be operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zcytor7 receptor polypeptide into the secretory pathway of a host cell, a secretory signal sequence (also known as a leader sequence, prepro sequence or pre sequence) is provided in the expression vector. The secretory signal sequence may be that of the receptor, or may be derived from another secreted protein (e.g., t-PA) or synthesized de novo. The secretory signal sequence is joined to the ZCytor7 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), and liposome-mediated transfection (Hawley-Nelson et al., *Focus* 15:73, 1993; Ciccarone et al., *Focus* 15:80, 1993. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463. The use of *Agrobacterium rhizogenes* as a vector for expressing genes in plant cells has been reviewed by Sinkar et al., *J. Biosci.* (Bangalore) 11:47–58, 1987.

Fungal cells, including yeast cells, and particularly cells of the genus Saccharomyces, can also be used within the present invention, such as for producing receptor fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat.

No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Within one aspect of the present invention, a novel receptor is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing ZCytor7 receptors and transducing a receptor-mediated signal include cells that express other receptor subunits which may form a functional complex with Zcytor7. These subunits may include those of the interferon receptor family or of other class II or class I cytokine receptors. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines. In the alternative, suitable host cells can be engineered to produce the necessary receptor subunit or other cellular component needed for the desired cellular response. For example, the murine cell line BaF3 (Palacios and Steinmetz, *Cell* 41:727–734, 1985; Mathey-Prevot et al., *Mol. Cell. Biol.* 6:4133–4135, 1986) or a baby hamster kidney (BHK) cell line can be transfected to express the necessary β subunit (also known as KH97) as well as a ZCytor7 receptor. The latter approach is advantageous because cell lines can be engineered to express receptor subunits from any species, thereby overcoming potential limitations arising from species specificity. In the alternative, species orthologs of the human receptor cDNA can be cloned and used within cell lines from the same species, such as a mouse cDNA in the BaF3 cell line. Cell lines that are dependent upon one hematopoietic growth factor, such as GM-CSF, can thus be engineered to become dependent upon a ZCytor7 ligand.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium b romide (MTT) (Mosman, *J. Immunol. Meth.* 65:55–63, 1983). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE (see, e.g., Shaw et al., *Cell* 56:563–572, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:29094–29101, 1994; Schenborn and Goiffin, *Promega Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

A natural ligand for the ZCytor7 receptor can also be identified by mutagenizing a cell line expressing the receptor and culturing it under conditions that select for autocrine growth. See WIPO publication WO 95/21930. Within a typical procedure, BaF3 cells expressing ZCytor7 and the necessary additional subunits are mutagenized, such as with 2-ethylmethanesulfonate (EMS). The cells are then allowed to recover in the presence of IL-3, then transferred to a culture medium lacking IL-3 and IL-4. Surviving cells are screened for the production of a ZCytor7 ligand, such as by adding soluble receptor to the culture medium or by assaying conditioned media on wild-type BaF3 cells and BaF3 cells expressing the receptor.

An additional screening approach provided by the present invention includes the use of hybrid receptor polypeptides. These hybrid polypeptides fall into two general classes. Within the first class, the intracellular domain of Z-Cytor7, comprising approximately residues 275 to 553 of SEQ ID NO:2, is joined to the ligand-binding domain of a second receptor. It is preferred that the second receptor be a hematopoietic cytokine receptor, such as mpl receptor (Souyri et al., *Cell* 63:1137–1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by ZCytor7 while using readily available ligands. This system can also be used to determine if particular cell lines are capable of responding to signals transduced by ZCytor7. A second class of hybrid receptor polypeptides comprise the extracellular (ligand-binding) domain of ZCytor7 (approximately residues 30 to 250 of SEQ ID NO:2) with an intracellular domain of a second receptor, preferably a hematopoietic cytokine receptor, and a transmembrane domain. Hybrid receptors of this second class are expressed in cells known to be capable of responding to signals transduced by the second receptor. Together, these two classes of hybrid receptors enable the identification of a responsive cell type for the development of an assay for detecting a Zcytor7 ligand.

Cells found to express the ligand are then used to prepare a cDNA library from which the ligand-encoding cDNA can be isolated as disclosed above. The present invention thus provides, in addition to novel receptor polypeptides, methods for cloning polypeptide ligands for the receptors.

The tissue specificity of Zcytor7 expression suggests a role in the development of the kidney, pancreas, prostate or nervous tissues. In view of the tissue specificity observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists may be useful in specifically promoting the growth and/or development of nervous, pancreatic or prostate-derived cells in culture. Antagonists are useful as research reagents for characterizing sites of ligand-receptor interaction. In vivo, receptor agonists or antagonists may find application in the treatment of renal, neural, pancreatic or prostate diseases.

ZCytor7 may also be used within diagnostic systems for the detection of circulating levels of ligand. Within a related embodiment, antibodies or other agents that specifically bind to ZCytor7 can be used to detect circulating receptor polypeptides. Elevated or depressed levels of ligand or receptor polypeptides may be indicative of pathological conditions, including cancer.

ZCytor7 receptor polypeptides can be prepared by expressing a truncated DNA encoding the extracellular domain, for example, a polypeptide which contains residues 30 through 250 of a human ZCytor7 receptor (SEQ ID NO:2) or the corresponding region of a non-human receptor. It is preferred that the extracellular domain polypeptides be prepared in a form substantially free of transmembrane and intracellular polypeptide segments. For example, the C-terminus of the receptor polypeptide may be at residue 250 of SEQ ID NO:2 or the corresponding region of an allelic variant or a non-human receptor. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a polyhystidine histidine tag, substance P, Flag™ peptide (Hopp et al., *Biotechnology* 6:1204–1210, 1988; available from Eastman Kodak Co., New Haven, Conn.) or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_c$ fragment, which contains two constant region domains and a hinge region but lacks the variable region. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a ZCytor7-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, *J. Immunol. Methods* 145:229–240, 1991 and Cunningham and Wells, *J. Mol. Biol.* 234:554–563, 1993. A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see, Scatchard, *Ann. NY Acad. Sci.* 51:660–672, 1949) and calorimetric assays (Cunningham et al., *Science* 253:545–548, 1991; Cunningham et al., *Science* 254:821–825, 1991).

A receptor ligand-binding polypeptide can also be used for purification of ligand. The receptor polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration or pH to disrupt ligand-receptor binding.

ZCytor7 polypeptides can also be used to prepare antibodies that specifically bind to ZCytor7 polypeptides. As used herein, the term "antibodies" includes polyclonal antibodies, monoclonal antibodies, single-chain antibodies and antigen-binding fragments thereof such as F(ab')$_2$ and Fab fragments, and the like, including genetically engineered antibodies. Antibodies are defined to be specifically binding if they bind to a ZCytor7 polypeptide with a K$_a$ of greater than or equal to $10^7$/M. The affinity of a monoclonal antibody can be readily determined by one of ordinary skill in the art (see, for example, Scatchard, ibid.).

Methods for preparing polyclonal and monoclonal antibodies are well known in the art (see for example, Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a ZCytor7 polypeptide may be increased through the use of an adjuvant such as Freund's complete or incomplete adjuvant. A variety of assays known to those skilled in the art can be utilized to detect antibodies which specifically bind to ZCytor7 polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Antibodies to ZCytor7 may be used for tagging cells that express the receptor, for affinity purification, within diagnostic assays for determining circulating levels of soluble receptor polypeptides, and as antagonists to block ligand binding and signal transduction in vitro and in vivo.

Anti-idiotypic antibodies which bind to the antigenic binding site of antibodies to Zcytor7 are also considered part of the present invention. The antigenic binding region of the anti-idiotypic antibody thus will mimic the ligand binding region of Zcytor7. An anti-idiotypic antibody thus could be used to screen for possible ligands of the Zcytor7 receptor. Thus neutralizing antibodies to Zcytor7 can be used to produce anti-idiotypic antibodies by methods well known in the art as is described in, for example, Sambrook et al., *Molecular Cloning: A Laboratory Manual, Second Edition*, (Cold Spring Harbor, N.Y., 1989); and Hurrell, J. G. R., Ed., *Monoclonal Hybridoma Antibodies: Techniques and Applications*, (CRC Press, Inc., Boca Raton, Fla., 1982).

Zcytor-7 maps 795.76 cR from the top of the human chromosome 6 linkage group on the WICGR radiation hybrid map. Relative to the centromere, its nearest proximal marker was CHLC.GATA32B03 and its nearest distal maker was SGC32063. The use of surrounding markers also helped position zcytor-7 in the 6q22-q23 region on the CHLC chromosome 6 version v8c7 integrated marker map. The locus where Zcytor7 maps onto chromosome 6 is a common breakpoint area in ALL(acute lymphoblastic leukemia) and NHL(non-Hodgkin lymphoma) as well as in AML(acute myelogenous leukemia) and CML(chronic myeloid leukemia). It is interesting to note that the MYB (avian myeloblastosis viral oncogene homolog) gene, which encodes proteins critical for hematopoetic cell proliferation and development, appears to be less than 800 kB from zcytor7. The 6q- deletion breakpoints occur slightly distal to the MYB gene and although the neoplasms show high levels of MYB mRNA, the gene itself appears to be intact.

Thus Zcytor7 could be used to generate a probe that could allow detection of an aberration of the Zctyor7 gene in the 6q chromosome which may indicate the presence of a cancerous cell such as leukemic cells which may still be present in after chemical or radiation therapy. If the Zcytor7 gene is deleted by the chromosomal abnormality, only one copy can be used to determine whether one or two copies of the gene are present per nucleus, thus indicating the percentage cancerous cells might be present relative to normal cells. For further discussions on developing polynucleotide probes and hybridization see *Current Protocols in Molecular Biology* Ausubel, F. et al. Eds. (John Wiley & Sons Inc. 1991).

Pharmaceutical Compositions

Pharmaceutical compositions can be formulated hich contain the soluble receptor, antibody or anti-idiotypic antibodies of the present invention. Generally included in such protein therapeutic compositions are buffers; surface adsorption inhibitors such as surfactants and polyols; and isotonic amounts of a physiologically acceptable salt. The composition may be formulated as an aqueous solution or a lyophilized powder. The latter is reconstituted prior to use with a pharmaceutically acceptable diluent such as sterile water for injection.

Examples of buffers which can be used for the above-described pharmaceutical compositions include low ionic strength, physiologically acceptable buffers that are effective within the pH range of 5.0–7.0. Such buffers include phosphate, acetate, citrate, succinate and histidine buffers.

Examples of surface adsorption inhibitors which can be used in the above-described pharmaceutical compositions include non-ionic surfactants and polyols. Non-ionic surfactants include polyoxyethylene sorbitan fatty acid esters, such as polysorbate 20 (polyoxyethylene sorbitan monolaurate), and the like. Other non-ionic surfactants useful in this regard include polyethylene oxides; sorbitan esters; polyoxyethylene alkyl ethers; and glycerides of fatty acid, including glyceryl monooleate and glyceryl monostearate. Polyols which can be used include polyethylene glycol, e.g. PEG 3350, mannitol, xylitol, sorbitol, inositol, and glycerol. In general, the surface adsorption inhibitor will be included within the composition at a concentration from 0.001% to 5%.

Physiologically acceptable salts are generally included in a protein therapeutic composition generally in an amount isotonic to human blood. Preferred salts in this regard include chloride salts such as NaCl, KCl, CaCl$_2$ and MgCl$_2$.

Albumin may also be included in the above-described pharmaceutical compositions. Human serum albumin is preferred for inclusion in pharmaceutical compositions intended for human use. Albumin is useful as an excipient in lyophilized compositions and acts as a stabilizer when included at a concentration of 0.1–1.0%. Albumin may useful as a surface adsorption inhibitor.

One or more preservatives may also be included in the pharmaceutical compositions of the present invention. Common preservative include methylparaben, propylparaben, benzyl alcohol, m-cresol, ethylmercurithiosalycilate, phenol, thimerosol and the like. Methods of formulation of pharmaceutical compositions are well known in the art and are disclosed, for example, in *Remington's Pharmaceutical Sciences*, Gennaro, ed., (Mack Publishing Co., Easton, Pa., 1996)

Dosages

Therapeutic doses of the protein compositions of the present invention will generally be in the range of 0.1 to 100 µg/kg of patient per day with the exact dose determined by the clinician.

The invention is further illustrated by the following non-limiting examples.

EXAMPLE 1

Cloning of Zcytor7

Expressed sequence tag (EST) 277139 (SEQ ID NO:3) was identified. The cDNA clone (ID No. 50416) was obtained from the IMAGE consortium Lawrence Livermore National Laboratory through Genome Systems, Inc. The cDNA was supplied as an agar stab containing E. coli transfected with a plasmid having the cDNA of interest. The E. coli was streaked on an agar plate. The plasmid was designated pSL7139. The cDNA insert in plasmid pSL7139 was sequenced. The insert was determined to be 1231 bp in length, but was not a full length sequence.

A human testis cDNA template was made using a MARATHON™ cDNA Amplification Kit (Clontech Laboratories, Inc., Palo Alto, Calif.) according to the supplier's instructions. A 5' RACE reaction was used to obtain a full-length cDNA. The RACE reaction was carried out in two reactions employing two sets of primers. Reaction I (outer nest), using primers ZC11,107 (SEQ ID NO:4) and AP-1 (SEQ ID NO: 5) (Clontech Laboratories) was run for 35 cycles at 98° C. for 20 seconds, 45° C. for 20 seconds; 68° for 4 minutes and a final extension time of 10 minutes at 68° C. One µl of a 1:100 dilution of the reaction product was used as a template in reaction II (inner nest). Primers were ZC11,108 (SEQ ID NO:6 ) and AP-2 (SEQ ID NO:7 ) (Clontech Laboratories). The reaction was run at 98° C. for 30 seconds, and 30 cycles each cycle being comprised of 98° C. for 28 seconds; 43° C. for 20 seconds; and 68° C. for 3.5 minutes with a final extension at 68° C. for 10 minutes.

The product of the inner nest RACE reaction was subcloned using a PCR-SCRIPT™ kit (Stratagene Cloning Systems, La Jolla, Calif.) to prepare the plasmid pSLR7-1. Sequence analysis of this plasmid indicated that the 5'RACE-generated sequence extended the sequence of pSL7139 by 555 bp.

Full-length cDNA was obtained by screening a λZAP® II human testis cDNA library using a probe that was generated by PCR primers ZC11,526 (SEQ ID NO:9) and ZC11,108 (SEQ ID NO:6) and pSLR7-1 as template and then re-amplified. The resulting probe was purified through recovery from low-melt agarose gel electrophoresis and was labeled with $^{32}$P-α-dCTP using a MEGAPRIME™ labeling kit (Amersham Corp., Arlington, Heights, Ill.). The labeled probe was purified on a push column (NUCTRAP® probe purification column; Stratagene Cloning Systems).

The first strand cDNA reaction contained 15 µl of human testis twice poly d(T)-selected poly (A)$^+$ mRNA (Clontech Laboratories) at a concentration of 1.0 µg/µl, and 3 µl of 20 pmole/µl first strand primer ZC6091 (SEQ ID NO:8) containing an Xho I restriction site. The mixture was heated at 70° C. for 4 minutes and cooled by chilling on ice. First stand cDNA synthesis was initiated by the addition of 12 µl of first strand buffer (5x SUPERSCRIPT™ buffer; Life Technologies, Gaithersburgh, Md.), 6 µl of 100 mM dithiothreitol, 3 µl of deoxynucleotide triphosphate solution containing 10 mM each of dTTP, dATP, dGTP, and 5-methyl-dCTP (Pharmacia LKB Biotechnology, Piscataway, N.J.) to the RNA-primer mixture. The reaction mixture was incubated at 37° C. for 2 minutes, followed by the addition of 15 µl of 200 U/µl Rnase H$^-$ reverse transcriptase (SUPERSCRIPT II®; Life Technologies). The efficiency of the first strand synthesis was analyzed in a parallel reaction by the addition of 5 µCi of $^{32}$P-αdCTP to 5 µl aliquot from one of the reaction mixtures to label the reaction for analysis. The reactions were incubated at 37° C. for 10 minutes, 45° C. for 1 hour, then incubated at 50° C. for 10 minutes. Unincorporated $^{32}$P-αdCTP in the labeled reaction and the unincorporated nucleotides and primers in the unlabeled first strand reactions were removed by chromatography on a 400 pore size gel filtration column (Clontech Laboratories). The length of labeled first strand cDNA was determined by agarose gel electrophoresis.

The second strand reaction contained 120 µl of the unlabeled first strand cDNA, 36 µl of 5x polymerase I buffer (125 mM Tris: HCl pH 7.5, 500 mM KCl, 25 mM MgCl$_2$, 50 mM (NH$_4$)$_2$SO$_4$)), 2.4 µl of 100 mM dithiothreitol, 3.6 µl of a solution containing 10 mM of each deoxynucleotide triphosphate, 6 µl of 5 mM β-NAD, 3.6 µl of 3 U/µl E. coli DNA ligase (New England Biolabs),9 µl of 10 U/µl E. coli DNA polymerase I (New England Biolabs), and 1.8 µl of 2 U/µl RNase H (life Technologies). A 10 µl aliquot from one of the second strand synthesis reactions was labeled by the addition of 10 µCi $^{32}$P-αdCTP to monitor the efficiency of second strand synthesis. The reactions were incubated at 16° C. for two hours, followed by the addition of 15 µl T4 DNA polymerase (10 U/µl, Boerhinger Mannheim, Indianapolis, Ind.) and incubated for an additional 5 minutes at 16° C. Unincorporated $^{32}$P-αdCTP in the labeled reaction was removed by chromatography through a 400 pore size gel filtration (Clontech Laboratories) before analysis by agarose gel electrophoresis. The unlabeled second strand reaction was terminated by the addition of 20 µl 0.5 M EDTA and extraction with phenol/chloroform and chloroform followed by ethanol precipitation in the presence of 2.5 M ammonium acetate and 4 µg of glycogen carrier. The yield of cDNA was estimated to be approximately 3 µg from starting mRNA template of 15 µg.

Eco RI adapters were ligated onto the 5' ends of the cDNA described above to enable cloning into an expression vector. A 10 µl aliquot of cDNA (approximately 1.5 µg) and 5 µl of 65 pmole/µl of Eco RI adapter (Pharmacia LKB Biotechnology Inc.) were mixed with 2 µl 10x ligase buffer (660 mM Tris-HCl pH 7.5, 100 mM MgCl$_2$), 2 µl of 10 mM ATP and 1 µl of 15 U/µl T4 DNA ligase (Promega Corp., Madison, Wis.). The reaction was incubated 2 hours at 5° C., two hours at 7.5° C., 2 hours at 10° C., and 10 hours at 12.5° C. The reaction was terminated by incubation at 70° C. for 20 minutes.

To facilitate the directional cloning of the cDNA into an expression vector, the cDNA was digested with Xho I, resulting in a cDNA having a 5' Eco RI cohesive end and a 3' Xho cohesive end. The Xho I restriction site at the 3' end of the cDNA had been previously introduced using the ZC6091 primer (SEQ ID NO: 8). Restriction enzyme digestion was carried out in a reaction mixture containing 20 µl of cDNA as described above, 10 µl of 10x H Buffer Xho I (Boehringer Mannheim), 69 µl H$_2$O and 1.0 µl of 40 U/µl Xho I (Boehringer Mannheim). Digestion was carried out at 37° C. for 40 minutes. The reaction was terminated by incubation at 70° C. for 10 minutes and chromatography through a 400 pore size gel filtration column (Clontech Laboratories).

The cDNA was ethanol precipitated, washed with 70% ethanol, air dried and resuspended in 14 µl water, 2 µl of ligase buffer (Promega Corp., Madison, Wis.), 2 μl T4 polynucleotide kinase (10 U/μl, Life Technologies). Following incubation at 37° C. for 30 minutes, the cDNA was heated to 65° C. for 5 minutes, cooled on ice, and electrophoresed on a 0.8% low melt agarose gel. The contaminating adapters and cDNA below 0.6 kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10× β-agarose I buffer (New England Biolabs) were added to the tube, and the agarose was melted by heating to 65° C. for 15 minutes. Following equilibration of the sample to 45° C., 3 μl of 1 U/μl β-agarose I (New England Biolabs) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 10 μl water.

The resulting cDNA was cloned into the lambda phage vector λZap® II (Stratagene Cloning Systems) that was predigested with Eco RI and Xho I and dephosphorylated. Ligation of the cDNA to the λZap® II vector was carried out in a reaction mixture containing 1.0 μl of prepared vector, 1.0 μl of human testis cDNA, 1.0 μl 10× Ligase Buffer (Promega Corp.), 1.0 μl of 10 mM ATP, 5 μl water, and 1.0 μl of T4 DNA Ligase at 15 units/ml (Promega Corp.). The ligation mixture was incubated at 5°–15° C. overnight in a temperature gradient. After incubation, the ligation mixture was packaged into phage using an in vitro packaging extract (Gigapack® III Gold packaging extract; Stratagene Cloning Systems), and the resulting library was titered according to the manufacturer's specifications.

The human testis λZAP® II library was used to infect E. coli host cells (XL1-Blue MRF' strain (Stratagene Cloning Systems), and 1.5×10⁶ plaque forming units (pfu) were plated onto 150-mm NZY plates at a density of about 50,000 pfu/plate. The inoculated plates were incubated overnight at 37° C. Filter plaque lifts were made using nylon membranes (Hybond™-N; Amersham Corp., Arlington Heights, Ill.), according to the procedures provided by the manufacturer. The filters were processed by denaturation in solution containing 1.5 M NaCl and 0.5 M NaOH for 6 minutes at room temperature. The filters were blotted briefly on filter paper to remove excess denaturation solution, followed by neutralization for 6 minutes in 1 M Tris-HCl, pH 7.5, and 1.5 M NaCl. Phage DNA was fixed onto the filters with 1,200 μJoules of UV energy in a UV Crosslinker (Stratalinker®; Stratagene Cloning Systems). After fixing, the filters were first pre-washed in an aqueous solution containing 0.25× standard sodium citrate (SSC), 0.25% sodium dodecyl sulfate (SDS) and 1 mM EDTA to remove cellular debris and then prehybridized in hybridization solution (5×SSC, 5×Denhardt's solution, 0.2% SDS and 1 mM EDTA). Heat-denatured, sheared salmon sperm DNA at a final concentration of 100 μg/ml was added. The filters were prehybridized at 65° C. overnight.

A probe was prepared as a PCR product by using oligonucleotide primers designed to amplify the human Zcytor7 coding region. A PCR reaction mixture was prepared containing 2 μl of ZC11526 (SEQ ID NO:9) 2 μl of ZC11,108 (SEQ ID NO:6), 1 μl of an overnight bacterial culture of pSLR7-1, 1 μl of 10 mM dNTP, 10 μl of 10× KlenTaq buffer (Clontech Laboratories), 82 μl water, and 2 μl KlenTaq DNA polymerase (Clontech laboratories). The PCR reaction was run as follows: 94° C. for 1 minute; 30 cycles of 95° C. for 20 seconds, 43° C. for 20 seconds, 68° C. for 1 minute; then held at 68° C. for 10 minutes. The PCR product was re-amplified and gel purified on a 0.8% low melt agarose gel.

Fifty nanograms PCR product was radiolabeled with $^{32}$P-α-dCTP by random priming using the MEGAPRIME® DNA Labeling System (Amersham), according to the manufacturer's specifications. The prehybridization solution was replaced with fresh hybridization solution containing 1.4× 10⁶ cpm/ml labeled probe and allowed to hybridize for 64 hours at 60° C. After hybridization, the hybridization solution was removed and the filters were rinsed in a wash solution containing 0.25×SSC, 0.25% SDS and 1 mM EDTA at 65° C. The filters were placed on autoradiograph film and exposed at −70° C. with intensifying screens for 72 hours.

Examination of the autoradiographs revealed multiple regions that hybridized with labeled probe. Agar plugs were picked from 12 regions for purification. Each agar plug was soaked 2 hours in 0.5 ml of SM solution containing 25 ml 4 M NaCl, 10 ml 1 M MgSO$_4$, 25 ml 2 M Tris HCl, 5 ml 2% gelatin and 935 ml H$_2$O and 10% (v/v) chloroform (Sambrook et al. *Molecular Cloning: A Laboratory Manual,* $2^{nd}$ ed., Cold Spring Harbor Laboratory Press, Cold Spring Harbor, N.Y., 1989). After incubation, the phages from each plug were diluted 1:1000 in SM. Aliquots of 50 μl were plated on 100 mm plates containing 300 μl of *E. coli* XL-1 Blue MRF' cells. The plates were incubated overnight at 37° C., and filter lifts were prepared, prehybridized overnight, hybridized overnight with a hybridization solution containing 1.1×10⁶ cpm/ml labeled probe, washed and autoradiographed. Examination of the resulting autoradiographs revealed 10 positive signals. The positive plaques were subjected to an additional round of purification.

The plasmids were excised using an ExASSIST/SOLR® system (Stratagene Cloning Systems), according to the manufacturer's specifications. These plasmid inserts were amplified by PCR for size determination. A clone, designated pSLR7-2 was sequenced and determined to have an insert of 3,532 bp in size.

EXAMPLE 2

Northern Blot Analysis

A 970 bp fragment of the Zcytor7 cDNA containing nucleotides 822–1791 was random primer labeled using a MULTIPRIME™ kit (Amersham Corp.). Labeled cDNA was purified from free counts using a push column (Stratagene Cloning Systems). A human RNA master dot blot (Clontech Laboratories) for three hours at 65° C., then hybridized with 10⁶ cpm/ml of labeled cDNA probe. The expression pattern for this blot, which contained RNA samples which had been normalized to the mRNA expression levels of eight different housekeeping genes, was highest in kidney, followed by spinal cord, prostate, and cerebellum.

EXAMPLE 3

Expression of Human Zcytor7 mRNA in Human Tissues

Poly(A)⁺ RNAs isolated from adrenal cortex, adrenal medulla, brain, colon, heart, kidney, liver, lung, ovary, pancreas, prostate, placenta, peripheral blood leukocytes, stomach, spleen, skeletal muscle, small intestine, testis, thymus, thyroid, fetal brain, fetal lung, fetal liver and fetal kidney were hybridized under high stringency conditions with a radiolabeled DNA probe containing nucleotides 822–1791 of (SEQ ID NO:1). Membranes were purchased from Clontech. The membrane were washed with 0.1×SSC, 0.1% SDS at 50° C. and autoradiographed for 24 hours. The mRNA levels were highest in adrenal cortex, pancreas and prostate with lower levels in testis, stomach, adrenal medulla and thyroid.

EXAMPLE 4

Chromosomal Assignment and Placement of Zcytor-7

Zcytor-7 was mapped to chromosome 6 using the commercially available version of the Whitehead Institute/MIT Center for Genome Research's "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zcytor-7 with the "GeneBridge 4 RH Panel", 25 µl reactions were set up in a PCRable 96-well microtiter plate (Stratagene, La Jolla, Calif.) and used in a "RoboCycler Gradient 96" thermal cycler (Stratagene). Each of the 95 PCR reactions consisted of 2.5 µl 50× "Advantage KlenTaq Polymerase Mix" (CLONTECH Laboratories, Inc., Palo Alto, Calif.), 2 µl dNTPs mix (2.5 mM each, PERKIN-ELMER, Foster City, Calif.), 1.25 µl sense primer, ZC 11,131, (SEQ ID NO: 11), 1.25 µl antisense primer, ZC 11,155, (SEQ ID NO: 12), 2.5 µl "Redi-Load" (Research Genetics, Inc., Huntsville, Ala.), 0.5 µl "Advantage KlenTaq Polymerase Mix" (Clontech Laboratories, Inc.), 25 ng of DNA from an individual hybrid clone or control and water is added to bring up the total volume to 25 µl. The reactions were overlaid with an equal amount of mineral oil and sealed. The PCR cycler conditions were as follows: an initial 1 cycle 4 minute denaturation at 94° C., 35 cycles of a 1 minute denaturation at 94° C., 1.5 minute annealing at 63° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that zcytor-7 maps 795.76 cR from the top of the human chromosome 6 linkage group on the WICGR radiation hybrid map. Relative to the centromere, its nearest proximal marker was CHLC.GATA32B03 and its nearest distal maker was SGC32063. The use of surrounding markers also helped position zcytor-7 in the 6q22-q23 region on the CHLC chromosome 6 version v8c7 integrated marker map (The Cooperative Human Linkage Center, WWW server: http://www.chlc.org/ChlcIntegratedMaps.html) and to 6q22.33-q23.1 on the integrated LDB chromosome 6 map (The Genetic Location Database, University of Southhampton, WWW server:http://cedar.genetics.soton.ac.uk/public_html/).

This is a common breakpoint area in ALL(acute lymphoblastic leukemia) and NHL(non-Hodgkin lymphoma) as well as in AML(acute myelogenous leukemia) and CML (chronic myeloid leukemia). It is interesting to note that the MYB (avian myeloblastosis viral oncogene homolog) gene, which encodes proteins critical for hematopoetic cell proliferation and development, appears to be less than 800 kB from zcytor7. The 6q- deletion breakpoints occur slightly distal to the MYB gene and although the neoplasms show high levels of MYB mRNA, the gene itself appears to be intact.

We claim:

1. An isolated polypeptide comprised of a sequence of amino acid residues extending from valine residue 30 through lysine residue 250 of SEQ ID NO: 2.

2. The isolated polypeptide of claim 1 wherein the sequence of amino acid residues extends from residue 30, a valine, through residue 274, a tyrosine.

3. The isolated polypeptide of claim 1 wherein the sequence of amino acid residues extends from residue 30, a valine residue, through residue 553, an asparagine residue.

4. A polypeptide comprised of SEQ ID NO:2.

* * * * *

SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
      (A) LENGTH: 3516 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 237...1895
      (D) OTHER INFORMATION:

(xi) SEQUENCE DESCRIPTION: SEQ ID NO:1:

```
TCCAGCTGGG TAGCCGGGGG AGCGCGCGTG GGGGCTCCGC GAGTCGCTCG CCCTTGGTTT      60

CTGGGGAAGC CTGGGGGACG CGGCTGTGGC GGAGGCGCCC TGGGACTCAG GTCGCCTGGA     120

GCGTGGCACG CAGAGCCCCA GGCGCGGAGC TGAGGCCGCG CGGCCGCGCT TGGCCCCAGC     180
```

-continued

| | |
|---|---|
| GGGCGTGGGA CTGAGCAGTC TGCTGCCCCC CGACATGTGA CCCAGCCCCG CCGCCC ATG<br>                                                                                         Met<br>                                                                                         1 | 239 |
| CGG GCT CCC GGC CGC CCG GCC CTG CGG CCG CTG CCG CTG CCG CCG CTG<br>Arg Ala Pro Gly Arg Pro Ala Leu Arg Pro Leu Pro Leu Pro Pro Leu<br>               5                           10                        15 | 287 |
| CTG CTG TTG CTC CTG GCG GCG CCT TGG GGA CGG GCA GTT CCC TGT GTC<br>Leu Leu Leu Leu Leu Ala Ala Pro Trp Gly Arg Ala Val Pro Cys Val<br>         20                       25                       30 | 335 |
| TCT GGT GGT TTG CCT AAA CCT GCA AAC ATC ACC TTC TTA TCC ATC AAC<br>Ser Gly Gly Leu Pro Lys Pro Ala Asn Ile Thr Phe Leu Ser Ile Asn<br> 35                        40                       45 | 383 |
| ATG AAG AAT GTC CTA CAA TGG ACT CCA CCA GAG GGT CTT CAA GGA GTT<br>Met Lys Asn Val Leu Gln Trp Thr Pro Pro Glu Gly Leu Gln Gly Val<br>50                   55                       60                   65 | 431 |
| AAA GTT ACT TAC ACT GTG CAG TAT TTC ATA TAT GGG CAA AAG AAA TGG<br>Lys Val Thr Tyr Thr Val Gln Tyr Phe Ile Tyr Gly Gln Lys Lys Trp<br>                    70                       75                       80 | 479 |
| CTG AAT AAA TCA GAA TGC AGA AAT ATC AAT AGA ACC TAC TGT GAT CTT<br>Leu Asn Lys Ser Glu Cys Arg Asn Ile Asn Arg Thr Tyr Cys Asp Leu<br>               85                       90                       95 | 527 |
| TCT GCT GAA ACT TCT GAC TAC GAA CAC CAG TAT TAT GCC AAA GTT AAG<br>Ser Ala Glu Thr Ser Asp Tyr Glu His Gln Tyr Tyr Ala Lys Val Lys<br>         100                      105                     110 | 575 |
| GCC ATT TGG GGA ACA AAG TGT TCC AAA TGG GCT GAA AGT GGA CGG TTC<br>Ala Ile Trp Gly Thr Lys Cys Ser Lys Trp Ala Glu Ser Gly Arg Phe<br>115                  120                     125 | 623 |
| TAT CCT TTT TTA GAA ACA CAA ATT GGC CCA CCA GAG GTG GCA CTG ACT<br>Tyr Pro Phe Leu Glu Thr Gln Ile Gly Pro Pro Glu Val Ala Leu Thr<br>130                  135                   140                145 | 671 |
| ACA GAT GAG AAG TCC ATT TCT GTT GTC CTG ACA GCT CCA GAG AAG TGG<br>Thr Asp Glu Lys Ser Ile Ser Val Val Leu Thr Ala Pro Glu Lys Trp<br>                  150                   155                 160 | 719 |
| AAG AGA AAT CCA GAA GAC CTT CCT GTT TCC ATG CAA CAA ATA TAC TCC<br>Lys Arg Asn Pro Glu Asp Leu Pro Val Ser Met Gln Gln Ile Tyr Ser<br>               165                     170                   175 | 767 |
| AAT CTG AAG TAT AAC GTG TCT GTG TTG AAT ACT AAA TCA AAC AGA ACG<br>Asn Leu Lys Tyr Asn Val Ser Val Leu Asn Thr Lys Ser Asn Arg Thr<br>      180                      185                   190 | 815 |
| TGG TCC CAG TGT GTG ACC AAC CAC ACG CTG GTG CTC ACC TGG CTG GAG<br>Trp Ser Gln Cys Val Thr Asn His Thr Leu Val Leu Thr Trp Leu Glu<br>195                  200                     205 | 863 |
| CCG AAC ACT CTT TAC TGC GTA CAC GTG GAG TCC TTC GTC CCA GGG CCC<br>Pro Asn Thr Leu Tyr Cys Val His Val Glu Ser Phe Val Pro Gly Pro<br>210                  215                   220                225 | 911 |
| CCT CGC CGT GCT CAG CCT TCT GAG AAG CAG TGT GCC AGG ACT TTG AAA<br>Pro Arg Arg Ala Gln Pro Ser Glu Lys Gln Cys Ala Arg Thr Leu Lys<br>                  230                   235                 240 | 959 |
| GAT CAA TCA TCA GAG TTC AAG GCT AAA ATC ATC TTC TGG TAT GTT TTG<br>Asp Gln Ser Ser Glu Phe Lys Ala Lys Ile Ile Phe Trp Tyr Val Leu<br>               245                     250                   255 | 1007 |
| CCC ATA TCT ATT ACC GTG TTT CTT TTT TCT GTG ATG GGC TAT TCC ATC<br>Pro Ile Ser Ile Thr Val Phe Leu Phe Ser Val Met Gly Tyr Ser Ile<br>      260                      265                   270 | 1055 |
| TAC CGA TAT ATC CAC GTT GGC AAA GAG AAA CAC CCA GCA AAT TTG ATT<br>Tyr Arg Tyr Ile His Val Gly Lys Glu Lys His Pro Ala Asn Leu Ile<br>275                  280                     285 | 1103 |
| TTG ATT TAT GGA AAT GAA TTT GAC AAA AGA TTC TTT GTG CCT GCT GAA<br>Leu Ile Tyr Gly Asn Glu Phe Asp Lys Arg Phe Phe Val Pro Ala Glu<br>290                  295                   300                305 | 1151 |

-continued

| | | |
|---|---|---|
| AAA ATC GTG ATT AAC TTT ATC ACC CTC AAT ATC TCG GAT GAT TCT AAA<br>Lys Ile Val Ile Asn Phe Ile Thr Leu Asn Ile Ser Asp Asp Ser Lys<br>                 310                 315                 320 | 1199 |
| ATT TCT CAT CAG GAT ATG AGT TTA CTG GGA AAA AGC AGT GAT GTA TCC<br>Ile Ser His Gln Asp Met Ser Leu Leu Gly Lys Ser Ser Asp Val Ser<br>             325                 330                 335 | 1247 |
| AGC CTT AAT GAT CCT CAG CCC AGC GGG AAC CTG AGG CCC CCT CAG GAG<br>Ser Leu Asn Asp Pro Gln Pro Ser Gly Asn Leu Arg Pro Pro Gln Glu<br>        340                 345                 350 | 1295 |
| GAA GAG GAG GTG AAA CAT TTA GGG TAT GCT TCG CAT TTG ATG GAA ATT<br>Glu Glu Glu Val Lys His Leu Gly Tyr Ala Ser His Leu Met Glu Ile<br>355                 360                 365 | 1343 |
| TTT TGT GAC TCT GAA GAA AAC ACG GAA GGT ACT TCT TTC ACC CAG CAA<br>Phe Cys Asp Ser Glu Glu Asn Thr Glu Gly Thr Ser Phe Thr Gln Gln<br>370                 375                 380                 385 | 1391 |
| GAG TCC CTC AGC AGA ACA ATA CCC CCG GAT AAA ACA GTC ATT GAA TAT<br>Glu Ser Leu Ser Arg Thr Ile Pro Pro Asp Lys Thr Val Ile Glu Tyr<br>                 390                 395                 400 | 1439 |
| GAA TAT GAT GTC AGA ACC ACT GAC ATT TGT GCG GGG CCT GAA GAG CAG<br>Glu Tyr Asp Val Arg Thr Thr Asp Ile Cys Ala Gly Pro Glu Glu Gln<br>             405                 410                 415 | 1487 |
| GAG CTC AGT TTG CAG GAG GAG GTG TCC ACA CAA GGA ACA TTA TTG GAG<br>Glu Leu Ser Leu Gln Glu Glu Val Ser Thr Gln Gly Thr Leu Leu Glu<br>        420                 425                 430 | 1535 |
| TCG CAG GCA GCG TTG GCA GTC TTG GGC CCG CAA ACG TTA CAG TAC TCA<br>Ser Gln Ala Ala Leu Ala Val Leu Gly Pro Gln Thr Leu Gln Tyr Ser<br>435                 440                 445 | 1583 |
| TAC ACC CCT CAG CTC CAA GAC TTA GAC CCC CTG GCG CAG GAG CAC ACA<br>Tyr Thr Pro Gln Leu Gln Asp Leu Asp Pro Leu Ala Gln Glu His Thr<br>450                 455                 460                 465 | 1631 |
| GAC TCG GAG GAG GGG CCG GAG GAA GAG CCA TCG ACG ACC CTG GTC GAC<br>Asp Ser Glu Glu Gly Pro Glu Glu Pro Ser Thr Thr Leu Val Asp<br>                 470                 475                 480 | 1679 |
| TGG GAT CCC CAA ACT GGC AGG CTG TGT ATT CCT TCG CTG TCC AGC TTC<br>Trp Asp Pro Gln Thr Gly Arg Leu Cys Ile Pro Ser Leu Ser Ser Phe<br>             485                 490                 495 | 1727 |
| GAC CAG GAT TCA GAG GGC TGC GAG CCT TCT GAG GGG GAT GGG CTC GGA<br>Asp Gln Asp Ser Glu Gly Cys Glu Pro Ser Glu Gly Asp Gly Leu Gly<br>        500                 505                 510 | 1775 |
| GAG GAG GGT CTT CTA TCT AGA CTC TAT GAG GAG CCG GCT CCA GAC AGG<br>Glu Glu Gly Leu Leu Ser Arg Leu Tyr Glu Glu Pro Ala Pro Asp Arg<br>515                 520                 525 | 1823 |
| CCA CCA GGA GAA AAT GAA ACC TAT CTC ATG CAA TTC ATG GAG GAA TGG<br>Pro Pro Gly Glu Asn Glu Thr Tyr Leu Met Gln Phe Met Glu Glu Trp<br>530                 535                 540                 545 | 1871 |
| GGG TTA TAT GTG CAG ATG GAA AAC TGATGCCAAC ACTTCCTTTT GCCTTTTGTT<br>Gly Leu Tyr Val Gln Met Glu Asn<br>                 550 | 1925 |
| TCCTGTGCAA ACAAGTGAGT CACCCCTTTG ATCCCAGCCA TAAAGTACCT GGGATGAAAG | 1985 |
| AAGTTTTTTC CAGTTTGTCA GTGTCTGTGA GAATTACTTA TTTCTTTTCT CTATTCTCAT | 2045 |
| AGCACGTGTG TGATTGGTTC ATGCATGTAG GTCTCTTAAC AATGATGGTG GGCCTCTGGA | 2105 |
| GTCCAGGGGC TGGCCGGTTG TTCTATGCAG AGAAAGCAGT CAATAAATGT TGCCAGACT | 2165 |
| GGGTGCAGAA TTTATTCAGG TGGGTGTACT CTGGCCTCTT GGTTCATTAT TTTCAAACAA | 2225 |
| GCACACTTGT ACAATTATTT TCTGGGTACT TCCCATATGC ACATAGCACT GTAAAAAATA | 2285 |
| TTTCCCAAAG ATCACTCATT TTATAAATAC CACTTTTTCA GAATTGGGTT TATTGCGAGC | 2345 |
| AGGAGGAGAT ACTTAAAACA TGCACATATA CCAGGTTGGT GGTAAGTTGG TCACATGTGA | 2405 |

```
AAACCTCAAC TATTTAATCA TCATGATTCA TATTTTGAGT GAATACATCA GGCACAGACC      2465

TTCATGATAT CACACACTCT TGGCTACTTT AAGAGGCCAT CTTTAATACT TTATGAGTAG      2525

TTCTGGAGTG TAAACATAAA CGAGTATTCT TTTGTAGTCA GAAAAGTGTC CTCTCAATAA      2585

TTTAGTAGGG GCTTATTGTC TCTCAAAACT AACCTAAAAG AAAATGACAC ATTTTATAAT      2645

AGAATATTAC ATTTATTTCT GGAAGTGTGT TTTCAAAAAG ATATTTACAT AGTCTGTAAA      2705

CTAGAAAGTG TTAGGTAAAG CTCTAGGTTA CTGTGTTACT ATTATAATAT TAAACATTCG      2765

AATAGGCAGT CGTTCAAAGA CTCTTTGGAA TATCTATGAA TGAATATCCT CTATTCTTAT      2825

AATATTAAAA CCCATAAGTA AATATAGGAC ATACAAGAGA AATGAGTTAA ATGACTATGT      2885

AAGGGAGAGT TTATTAAAAT TTGATGAAAT TTACTGTAGG AACTAAACTA TGCCATAAAA      2945

CAATAGCTTT CTAGTTCATT TCCAGTAACT GTTCCCATCT CCTTTACCAC TTGTTAAGAA      3005

AATTAAATTC TTCAGTCACG CTGCTTTAAA ATGGGACAAA ATCTATTAAG TTGAACCATA      3065

TATAATTGTG GATATTTGGC TGTTTTTAAT CTGACAAGCA GTAACTTCAT ATGGTTTGCC      3125

TTAATATATA TTTGTTTTAG TCATGAACTC ATAATCCATT GATGCTCTTT CATGAGAAGA      3185

GATATGACCC ATATTTCCTT ATTGATATTA TTGGTACAGG CAGACAACCC TGGTAGGAGA      3245

GATGGATTCT GGGGTCATGA CCTTTCGTGA TTATCCGCAA ATGCAAACAG TTTCAGATCT      3305

AATGGTTTAA TTTAGGGAGT AATTATATTA ATCAGAGTGT TCTGTTATTC TCAATCTTTA      3365

TAGAAACGAT TCTGCTGGTT TTGAAGAACA GATGTATTAC ACTAACTGTA AAAGTAGTTC      3425

AAGAGTGAGA AAGAATAAAT TGTTATTAAG AGCAAAAGAA AAATAAAGTG ATTGATGATA      3485

AAAAAAAAAA AAAAAAAGCG GCCGCCTCGA G                                    3516
```

(2) INFORMATION FOR SEQ ID NO:2:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Arg Ala Pro Gly Arg Pro Ala Leu Arg Pro Leu Pro Leu Pro Pro
 1               5                  10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
 50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
130                 135                 140
```

```
Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
    290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
        355                 360                 365

Ile Phe Cys Asp Ser Glu Glu Asn Thr Glu Gly Thr Ser Phe Thr Gln
    370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550
```

(2) INFORMATION FOR SEQ ID NO:3:

(i) SEQUENCE CHARACTERISTICS:
           (A) LENGTH: 451 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:3:

AGTGTGTGAC CAACCACACG CTGGTGCTCA CCTGGGCTGG AGCCGAACAC TCTTTACTGC     60

GTACACGTGG AGTCCTTCGT CCCAGGGCCC CCTCGCCGTG CTCAGCCTTC TGAGAAGCAG    120

TGTGCCAGGA CTTTGAAAGA TCAATCATCA GAGTTCAAGG CTAAAATCAT CTTCTGGTAT    180

GTTTTGCCCA TATCTATTAC CGTGTTTCTT TTTTCTGTGA TGGGCTATTC CATCTACCGA    240

TATATCCACG TTGGGCAAAG AGAAACACCC AGGCAAATTT GATTTTGATT TATGGGAAAT    300

GAATTTGACA AAAGATTCTT TGTGCCTGCT GGAAAAAATC GTGGATTAAC TTTATTCACC    360

CTCAATATCT CGGGTGGATT CTAAAATTTT CTCCATCCAG GGGTATGGAG GTTTACTGGG    420

GGTAAANGCG GGTGTTGTTT NCCAGGCCTT A                                   451

(2) INFORMATION FOR SEQ ID NO:4:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: Other (vii) IMMEDIATE SOURCE:
           (B) CLONE: ZC11107

(xi) SEQUENCE DESCRIPTION: SEQ ID NO:4:

GCTGGGTGTT TCTCTTTG                                                   18

(2) INFORMATION FOR SEQ ID NO:5:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: Other (xi) SEQUENCE DESCRIPTION: SEQ ID NO:5:

CCATCCTAAT ACGACTCACT ATAGGGC                                         27

(2) INFORMATION FOR SEQ ID NO:6:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: Other (vii) IMMEDIATE SOURCE:
           (B) CLONE: ZC11108

(xi) SEQUENCE DESCRIPTION: SEQ ID NO:6:

GGAATAGCCC ATCACAGAAA                                                 20

(2) INFORMATION FOR SEQ ID NO:7:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO:7:

ACTCACTATA GGGCTCGAGC GGC                                       23

(2) INFORMATION FOR SEQ ID NO:8:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC6091

(xi) SEQUENCE DESCRIPTION: SEQ ID NO:8:

GAGCACAGAA TTCACTACTC GAGGCGGCCG CTTTTTTTTT TTTTTTTTT           49

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC11526

(xi) SEQUENCE DESCRIPTION: SEQ ID NO:9:

CACCAGAGGG TCTTCAAGGA GT                                        22

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...3
        (D) OTHER INFORMATION: Xaa = any amino acid (xi) SEQUENCE DESCRIPTION: SEQ ID NO:10:

Trp Ser Xaa Trp Ser
 1           5

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

AGATCCTTTG TGCCTGCTGA                                                             20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

GTATTGTTCT GCTGAGGGAC                                                             20

(2) INFORMATION FOR SEQ ID NO:13:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:13:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGA CGG GCC GTT CCC TGT        96
Leu Leu Leu Leu Leu Leu Ala Ala Pro Trp Gly Arg Ala Val Pro Cys
             20                  25                  30

GTC TCT GGT GGT TTG CCT AAA CCT GCC AAC ATC ACC TTC TTA TCC ATC       144
Val Ser Gly Gly Leu Pro Lys Pro Ala Asn Ile Thr Phe Leu Ser Ile
         35                  40                  45

AAC ATG AAG AAT GTC CTA CAA TGG ACT CCA CCA GAG GGT CTT CAA GGA       192
Asn Met Lys Asn Val Leu Gln Trp Thr Pro Pro Glu Gly Leu Gln Gly
     50                  55                  60

GTT AAA GTT ACT TAC ACT GTG CAG TAT TTC ATA TAT GGG CAA AAG AAA       240
Val Lys Val Thr Tyr Thr Val Gln Tyr Phe Ile Tyr Gly Gln Lys Lys
 65                  70                  75                  80

TGG CTG AAT AAA TCA GAA TGT AGA AAT ATC AAT AGA ACC TAC TGT GAT       288
Trp Leu Asn Lys Ser Glu Cys Arg Asn Ile Asn Arg Thr Tyr Cys Asp
                 85                  90                  95

CTT TCT GCT GAA ACT TCT GAC TAC GAA CAC CAG TAT TAT GCC AAA GTT       336
Leu Ser Ala Glu Thr Ser Asp Tyr Glu His Gln Tyr Tyr Ala Lys Val
            100                 105                 110

AAG GCC ATT TGG GGA ACA AAG TGT TCC AAA TGG GCT GAA AGT GGA CGG       384
Lys Ala Ile Trp Gly Thr Lys Cys Ser Lys Trp Ala Glu Ser Gly Arg
        115                 120                 125

TTC TAT CCT TTT TTA GAA ACA CAA ATT GGC CCA CCA GAG GTG GCC CTG       432
Phe Tyr Pro Phe Leu Glu Thr Gln Ile Gly Pro Pro Glu Val Ala Leu
    130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160
```

```
TGG AAG AGA AAT CCA GAA GAC CTT CCT GTT TCC ATG CAA CAA ATA TAC      528
Trp Lys Arg Asn Pro Glu Asp Leu Pro Val Ser Met Gln Gln Ile Tyr
            165             170             175

TCC AAT CTG AAG TAT AAC GTG TCT GTG TTG AAT ACT AAA TCA AAC AGA      576
Ser Asn Leu Lys Tyr Asn Val Ser Val Leu Asn Thr Lys Ser Asn Arg
            180             185             190

ACG TGG TCC CAG TGT GTG ACC AAC CAC ACG CTG GTG CTC ACC TGG CTG      624
Thr Trp Ser Gln Cys Val Thr Asn His Thr Leu Val Leu Thr Trp Leu
            195             200             205

GAG CCG AAC ACT CTT TAC TGT GTA CAC GTG GAG TCC TTC GTC CCA GGG      672
Glu Pro Asn Thr Leu Tyr Cys Val His Val Glu Ser Phe Val Pro Gly
210             215             220

CCC CCT CGC CGT GCT CAG CCT TCT GAG AAG CAG TGT GCC AGG ACT TTG      720
Pro Pro Arg Arg Ala Gln Pro Ser Glu Lys Gln Cys Ala Arg Thr Leu
225             230             235             240

AAA GAT CAA TCA TCA GAG TTC AAG GCT AAA ATC ATC TTC TGG TAT GTT      768
Lys Asp Gln Ser Ser Glu Phe Lys Ala Lys Ile Ile Phe Trp Tyr Val
            245             250             255

TTG CCC ATA TCT ATT ACC GTG TTT CTT TTT TCT GTG ATG GGC TAT TCC      816
Leu Pro Ile Ser Ile Thr Val Phe Leu Phe Ser Val Met Gly Tyr Ser
            260             265             270

ATC TAC CGA TAT ATC CAC GTT GGC AAA GAG AAA CAC CCA GCC AAT TTG      864
Ile Tyr Arg Tyr Ile His Val Gly Lys Glu Lys His Pro Ala Asn Leu
            275             280             285

ATT TTG ATT TAT GGA AAT GAA TTT GAC AAA AGA TTC TTT GTG CCT GCT      912
Ile Leu Ile Tyr Gly Asn Glu Phe Asp Lys Arg Phe Phe Val Pro Ala
290             295             300

GAA AAA ATC GTG ATT AAC TTT ATC ACC CTC AAT ATC TCG GAT GAT TCT      960
Glu Lys Ile Val Ile Asn Phe Ile Thr Leu Asn Ile Ser Asp Asp Ser
305             310             315             320

AAA ATT TCT CAT CAG GAT ATG AGT TTA CTG GGA AAA AGC AGT GAT GTA     1008
Lys Ile Ser His Gln Asp Met Ser Leu Leu Gly Lys Ser Ser Asp Val
            325             330             335

TCC AGC CTT AAT GAT CCT CAG CCC AGC GGG AAC CTG AGG CCC CCT CAG     1056
Ser Ser Leu Asn Asp Pro Gln Pro Ser Gly Asn Leu Arg Pro Pro Gln
            340             345             350

GAG GAA GAG GAG GTG AAA CAT TTA GGG TAT GCT TCG CAT TTG ATG GAA     1104
Glu Glu Glu Glu Val Lys His Leu Gly Tyr Ala Ser His Leu Met Glu
            355             360             365

ATT TTT TGT GAC TCT GAA GAA AAC ACG GAA GGT ACT TCT TTC ACC CAG     1152
Ile Phe Cys Asp Ser Glu Glu Asn Thr Glu Gly Thr Ser Phe Thr Gln
            370             375             380

CAA GAG TCC CTC AGC AGA ACA ATA CCC CCG GAT AAA ACA GTC ATT GAA     1200
Gln Glu Ser Leu Ser Arg Thr Ile Pro Pro Asp Lys Thr Val Ile Glu
385             390             395             400

TAT GAA TAT GAT GTC AGA ACC ACT GAC ATT TGT GCG GGG CCT GAA GAG     1248
Tyr Glu Tyr Asp Val Arg Thr Thr Asp Ile Cys Ala Gly Pro Glu Glu
            405             410             415

CAG GAG CTC AGT TTG CAG GAG GAG GTG TCC ACA CAA GGA ACA TTA TTG     1296
Gln Glu Leu Ser Leu Gln Glu Glu Val Ser Thr Gln Gly Thr Leu Leu
            420             425             430

GAG TCG CAG GCC GCG TTG GCC GTC TTG GGC CCG CAA ACG TTA CAG TAC     1344
Glu Ser Gln Ala Ala Leu Ala Val Leu Gly Pro Gln Thr Leu Gln Tyr
            435             440             445

TCA TAC ACC CCT CAG CTC CAA GAC TTA GAC CCC CTG GCG CAG GAG CAC     1392
Ser Tyr Thr Pro Gln Leu Gln Asp Leu Asp Pro Leu Ala Gln Glu His
            450             455             460

ACA GAC TCG GAG GAG GGG CCG GAG GAA GAG CCA TCG ACG ACC CTG GTC     1440
Thr Asp Ser Glu Glu Gly Pro Glu Glu Glu Pro Ser Thr Thr Leu Val
465             470             475             480
```

```
GAC TGG GAT CCC CAA ACT GGC AGG CTG TGT ATT CCT TCG CTG TCC AGC      1488
Asp Trp Asp Pro Gln Thr Gly Arg Leu Cys Ile Pro Ser Leu Ser Ser
            485                 490                 495

TTC GAC CAG GAT TCA GAG GGC TGT GAG CCT TCT GAG GGG GAT GGG CTC      1536
Phe Asp Gln Asp Ser Glu Gly Cys Glu Pro Ser Glu Gly Asp Gly Leu
                500                 505                 510

GGA GAG GAG GGT CTT CTA TCT AGA CTC TAT GAG GAG CCG GCT CCA GAC      1584
Gly Glu Glu Gly Leu Leu Ser Arg Leu Tyr Glu Glu Pro Ala Pro Asp
        515                 520                 525

AGG CCA CCA GGA GAA AAT GAA ACC TAT CTC ATG CAA TTC ATG GAG GAA      1632
Arg Pro Pro Gly Glu Asn Glu Thr Tyr Leu Met Gln Phe Met Glu Glu
    530                 535                 540

TGG GGG TTA TAT GTG CAG ATG GAA AAC                                   1659
Trp Gly Leu Tyr Val Gln Met Glu Asn
545                 550
```

(2) INFORMATION FOR SEQ ID NO:14:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:14:

```
Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240
```

-continued

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
    290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
        355                 360                 365

Ile Phe Cys Asp Ser Glu Glu Asn Thr Glu Gly Thr Ser Phe Thr Gln
    370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550

(2) INFORMATION FOR SEQ ID NO:15:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:15:

-continued

| | | | | | | | | | | | | | | | | |
|---|---|---|---|---|---|---|---|---|---|---|---|---|---|---|---|---|
| ATG | CGG | GCT | CCC | GGC | CGC | CCG | GCC | CTG | CGG | CCG | CTG | CCG | CTG | CCG | CCG | 48 |
| Met | Arg | Ala | Pro | Gly | Arg | Pro | Ala | Leu | Arg | Pro | Leu | Pro | Leu | Pro | Pro | |
| 1 | | | | 5 | | | | | 10 | | | | | 15 | | |

| CTG | CTG | CTG | TTG | CTC | CTG | GCG | GCG | CCT | TGG | GGA | CGG | GCA | GTT | CCC | TGT | 96 |
|---|---|---|---|---|---|---|---|---|---|---|---|---|---|---|---|---|
| Leu | Leu | Leu | Leu | Leu | Leu | Ala | Ala | Pro | Trp | Gly | Arg | Ala | Val | Pro | Cys | |
| | | | 20 | | | | | 25 | | | | | 30 | | | |

| GTC | TCT | GGT | GGT | TTG | CCT | AAA | CCT | GCA | AAC | ATC | ACC | TTC | TTA | TCC | ATC | 144 |
|---|---|---|---|---|---|---|---|---|---|---|---|---|---|---|---|---|
| Val | Ser | Gly | Gly | Leu | Pro | Lys | Pro | Ala | Asn | Ile | Thr | Phe | Leu | Ser | Ile | |
| | 35 | | | | | 40 | | | | | 45 | | | | | |

| AAC | ATG | AAG | AAT | GTC | CTA | CAA | TGG | ACT | CCA | CCA | GAG | GGT | CTT | CAA | GGA | 192 |
|---|---|---|---|---|---|---|---|---|---|---|---|---|---|---|---|---|
| Asn | Met | Lys | Asn | Val | Leu | Gln | Trp | Thr | Pro | Pro | Glu | Gly | Leu | Gln | Gly | |
| 50 | | | | | 55 | | | | | 60 | | | | | | |

| GTT | AAA | GTT | ACT | TAC | ACT | GTG | CAG | TAT | TTC | ATA | TAT | GGG | CAA | AAG | AAA | 240 |
|---|---|---|---|---|---|---|---|---|---|---|---|---|---|---|---|---|
| Val | Lys | Val | Thr | Tyr | Thr | Val | Gln | Tyr | Phe | Ile | Tyr | Gly | Gln | Lys | Lys | |
| 65 | | | | 70 | | | | | 75 | | | | | 80 | | |

| TGG | CTG | AAT | AAA | TCA | GAA | TGT | AGA | AAT | ATC | AAT | AGA | ACC | TAC | TGT | GAT | 288 |
|---|---|---|---|---|---|---|---|---|---|---|---|---|---|---|---|---|
| Trp | Leu | Asn | Lys | Ser | Glu | Cys | Arg | Asn | Ile | Asn | Arg | Thr | Tyr | Cys | Asp | |
| | | | | 85 | | | | | 90 | | | | | 95 | | |

| CTT | TCT | GCT | GAA | ACT | TCT | GAT | TAC | GAA | CAC | CAG | TAT | TAT | GCC | AAA | GTT | 336 |
|---|---|---|---|---|---|---|---|---|---|---|---|---|---|---|---|---|
| Leu | Ser | Ala | Glu | Thr | Ser | Asp | Tyr | Glu | His | Gln | Tyr | Tyr | Ala | Lys | Val | |
| | | | 100 | | | | | 105 | | | | | 110 | | | |

| AAG | GCC | ATT | TGG | GGA | ACA | AAG | TGT | TCC | AAA | TGG | GCT | GAA | AGT | GGA | CGG | 384 |
|---|---|---|---|---|---|---|---|---|---|---|---|---|---|---|---|---|
| Lys | Ala | Ile | Trp | Gly | Thr | Lys | Cys | Ser | Lys | Trp | Ala | Glu | Ser | Gly | Arg | |
| | | 115 | | | | | 120 | | | | | 125 | | | | |

| TTC | TAT | CCT | TTT | TTA | GAA | ACA | CAA | ATT | GGC | CCA | CCA | GAG | GTG | GCA | CTG | 432 |
|---|---|---|---|---|---|---|---|---|---|---|---|---|---|---|---|---|
| Phe | Tyr | Pro | Phe | Leu | Glu | Thr | Gln | Ile | Gly | Pro | Pro | Glu | Val | Ala | Leu | |
| 130 | | | | | 135 | | | | | 140 | | | | | | |

| ACT | ACA | GAT | GAG | AAG | TCC | ATT | TCT | GTT | GTC | CTG | ACA | GCT | CCA | GAG | AAG | 480 |
|---|---|---|---|---|---|---|---|---|---|---|---|---|---|---|---|---|
| Thr | Thr | Asp | Glu | Lys | Ser | Ile | Ser | Val | Val | Leu | Thr | Ala | Pro | Glu | Lys | |
| 145 | | | | | 150 | | | | | 155 | | | | | 160 | |

| TGG | AAG | AGA | AAT | CCA | GAA | GAT | CTT | CCT | GTT | TCC | ATG | CAA | CAA | ATA | TAC | 528 |
|---|---|---|---|---|---|---|---|---|---|---|---|---|---|---|---|---|
| Trp | Lys | Arg | Asn | Pro | Glu | Asp | Leu | Pro | Val | Ser | Met | Gln | Gln | Ile | Tyr | |
| | | | | 165 | | | | | 170 | | | | | 175 | | |

| TCC | AAT | CTG | AAG | TAT | AAC | GTG | TCT | GTG | TTG | AAT | ACT | AAA | TCA | AAC | AGA | 576 |
|---|---|---|---|---|---|---|---|---|---|---|---|---|---|---|---|---|
| Ser | Asn | Leu | Lys | Tyr | Asn | Val | Ser | Val | Leu | Asn | Thr | Lys | Ser | Asn | Arg | |
| | | | 180 | | | | | 185 | | | | | 190 | | | |

| ACG | TGG | TCC | CAG | TGT | GTG | ACC | AAC | CAC | ACG | CTG | GTG | CTC | ACC | TGG | CTG | 624 |
|---|---|---|---|---|---|---|---|---|---|---|---|---|---|---|---|---|
| Thr | Trp | Ser | Gln | Cys | Val | Thr | Asn | His | Thr | Leu | Val | Leu | Thr | Trp | Leu | |
| | | 195 | | | | | 200 | | | | | 205 | | | | |

| GAG | CCG | AAC | ACT | CTT | TAC | TGT | GTA | CAC | GTG | GAG | TCC | TTC | GTC | CCA | GGG | 672 |
|---|---|---|---|---|---|---|---|---|---|---|---|---|---|---|---|---|
| Glu | Pro | Asn | Thr | Leu | Tyr | Cys | Val | His | Val | Glu | Ser | Phe | Val | Pro | Gly | |
| 210 | | | | | 215 | | | | | 220 | | | | | | |

| CCC | CCT | CGC | CGT | GCT | CAG | CCT | TCT | GAG | AAG | CAG | TGT | GCC | AGG | ACT | TTG | 720 |
|---|---|---|---|---|---|---|---|---|---|---|---|---|---|---|---|---|
| Pro | Pro | Arg | Arg | Ala | Gln | Pro | Ser | Glu | Lys | Gln | Cys | Ala | Arg | Thr | Leu | |
| 225 | | | | 230 | | | | | 235 | | | | | 240 | | |

| AAA | GAT | CAA | TCA | TCA | GAG | TTC | AAG | GCT | AAA | ATC | ATC | TTC | TGG | TAT | GTT | 768 |
|---|---|---|---|---|---|---|---|---|---|---|---|---|---|---|---|---|
| Lys | Asp | Gln | Ser | Ser | Glu | Phe | Lys | Ala | Lys | Ile | Ile | Phe | Trp | Tyr | Val | |
| | | | 245 | | | | | 250 | | | | | 255 | | | |

| TTG | CCC | ATA | TCT | ATT | ACC | GTG | TTT | CTT | TTT | TCT | GTG | ATG | GGC | TAT | TCC | 816 |
|---|---|---|---|---|---|---|---|---|---|---|---|---|---|---|---|---|
| Leu | Pro | Ile | Ser | Ile | Thr | Val | Phe | Leu | Phe | Ser | Val | Met | Gly | Tyr | Ser | |
| | | | 260 | | | | | 265 | | | | | 270 | | | |

| ATC | TAC | CGA | TAT | ATC | CAC | GTT | GGC | AAA | GAG | AAA | CAC | CCA | GCA | AAT | TTG | 864 |
|---|---|---|---|---|---|---|---|---|---|---|---|---|---|---|---|---|
| Ile | Tyr | Arg | Tyr | Ile | His | Val | Gly | Lys | Glu | Lys | His | Pro | Ala | Asn | Leu | |
| | | 275 | | | | | 280 | | | | | 285 | | | | |

| ATT | TTG | ATT | TAT | GGA | AAT | GAA | TTT | GAT | AAA | AGA | TTC | TTT | GTG | CCT | GCT | 912 |
|---|---|---|---|---|---|---|---|---|---|---|---|---|---|---|---|---|
| Ile | Leu | Ile | Tyr | Gly | Asn | Glu | Phe | Asp | Lys | Arg | Phe | Phe | Val | Pro | Ala | |
| | 290 | | | | | 295 | | | | | 300 | | | | | |

| GAA | AAA | ATC | GTG | ATT | AAC | TTT | ATC | ACC | CTC | AAT | ATC | TCG | GAT | GAT | TCT | 960 |
|---|---|---|---|---|---|---|---|---|---|---|---|---|---|---|---|---|
| Glu | Lys | Ile | Val | Ile | Asn | Phe | Ile | Thr | Leu | Asn | Ile | Ser | Asp | Asp | Ser | |
| 305 | | | | | 310 | | | | | 315 | | | | | 320 | |

```
AAA ATT TCT CAT CAG GAT ATG AGT TTA CTG GGA AAA AGC AGT GAT GTA        1008
Lys Ile Ser His Gln Asp Met Ser Leu Leu Gly Lys Ser Ser Asp Val
                325                 330                 335

TCC AGC CTT AAT GAT CCT CAG CCC AGC GGG AAC CTG AGG CCC CCT CAG        1056
Ser Ser Leu Asn Asp Pro Gln Pro Ser Gly Asn Leu Arg Pro Pro Gln
            340                 345                 350

GAG GAA GAG GAG GTG AAA CAT TTA GGG TAT GCT TCG CAT TTG ATG GAA        1104
Glu Glu Glu Glu Val Lys His Leu Gly Tyr Ala Ser His Leu Met Glu
        355                 360                 365

ATT TTT TGT GAT TCT GAA GAA AAC ACG GAA GGT ACT TCT TTC ACC CAG        1152
Ile Phe Cys Asp Ser Glu Glu Asn Thr Glu Gly Thr Ser Phe Thr Gln
    370                 375                 380

CAA GAG TCC CTC AGC AGA ACA ATA CCC CCG GAT AAA ACA GTC ATT GAA        1200
Gln Glu Ser Leu Ser Arg Thr Ile Pro Pro Asp Lys Thr Val Ile Glu
385                 390                 395                 400

TAT GAA TAT GAT GTC AGA ACC ACT GAT ATT TGT GCG GGG CCT GAA GAG        1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTA TTG        1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC        1344
Glu Ser Gln Ala Ala Leu Ala Val Leu Gly Pro Gln Thr Leu Gln Tyr
        435                 440                 445

TCA TAC ACC CCT CAG CTC CAA GAT TTA GAT CCC CTG GCG CAG GAG CAC        1392
Ser Tyr Thr Pro Gln Leu Gln Asp Leu Asp Pro Leu Ala Gln Glu His
    450                 455                 460

ACA GAT TCG GAG GAG GGG CCG GAG GAA GAG CCA TCG ACG ACC CTG GTC        1440
Thr Asp Ser Glu Glu Gly Pro Glu Glu Glu Pro Ser Thr Thr Leu Val
465                 470                 475                 480

GAT TGG GAT CCC CAA ACT GGC AGG CTG TGT ATT CCT TCG CTG TCC AGC        1488
Asp Trp Asp Pro Gln Thr Gly Arg Leu Cys Ile Pro Ser Leu Ser Ser
                485                 490                 495

TTC GAT CAG GAT TCA GAG GGC TGT GAG CCT TCT GAG GGG GAT GGG CTC        1536
Phe Asp Gln Asp Ser Glu Gly Cys Glu Pro Ser Glu Gly Asp Gly Leu
            500                 505                 510

GGA GAG GAG GGT CTT CTA TCT AGA CTC TAT GAG GAG CCG GCT CCA GAT        1584
Gly Glu Glu Gly Leu Leu Ser Arg Leu Tyr Glu Glu Pro Ala Pro Asp
        515                 520                 525

AGG CCA CCA GGA GAA AAT GAA ACC TAT CTC ATG CAA TTC ATG GAG GAA        1632
Arg Pro Pro Gly Glu Asn Glu Thr Tyr Leu Met Gln Phe Met Glu Glu
    530                 535                 540

TGG GGG TTA TAT GTG CAG ATG GAA AAC                                    1659
Trp Gly Leu Tyr Val Gln Met Glu Asn
545                 550

(2) INFORMATION FOR SEQ ID NO:16:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:16:

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30
```

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
 65              70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
             100                 105                 110

Lys Ala Ile Trp Gly Thr Lys Cys Ser Lys Trp Ala Glu Ser Gly Arg
         115                 120                 125

Phe Tyr Pro Phe Leu Glu Thr Gln Ile Gly Pro Pro Glu Val Ala Leu
         130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                 165                 170                 175

Ser Asn Leu Lys Tyr Asn Val Ser Val Leu Asn Thr Lys Ser Asn Arg
             180                 185                 190

Thr Trp Ser Gln Cys Val Thr Asn His Thr Leu Val Leu Thr Trp Leu
         195                 200                 205

Glu Pro Asn Thr Leu Tyr Cys Val His Val Glu Ser Phe Val Pro Gly
         210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                 245                 250                 255

Leu Pro Ile Ser Ile Thr Val Phe Leu Phe Ser Val Met Gly Tyr Ser
             260                 265                 270

Ile Tyr Arg Tyr Ile His Val Gly Lys Glu Lys His Pro Ala Asn Leu
         275                 280                 285

Ile Leu Ile Tyr Gly Asn Glu Phe Asp Lys Arg Phe Phe Val Pro Ala
         290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                 325                 330                 335

Ser Ser Leu Asn Asp Pro Gln Pro Ser Gly Asn Leu Arg Pro Pro Gln
             340                 345                 350

Glu Glu Glu Glu Val Lys His Leu Gly Tyr Ala Ser His Leu Met Glu
         355                 360                 365

Ile Phe Cys Asp Ser Glu Glu Asn Thr Glu Gly Thr Ser Phe Thr Gln
         370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                 405                 410                 415

Gln Glu Leu Ser Leu Gln Glu Glu Val Ser Thr Gln Gly Thr Leu Leu
             420                 425                 430

Glu Ser Gln Ala Ala Leu Ala Val Leu Gly Pro Gln Thr Leu Gln Tyr
         435                 440                 445
```

-continued

```
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                    485                 490                 495
Phe Asp Gln Asp Ser Glu Gly Cys Glu Pro Ser Glu Gly Asp Gly Leu
                500                 505                 510
Gly Glu Glu Gly Leu Leu Ser Arg Leu Tyr Glu Glu Pro Ala Pro Asp
            515                 520                 525
Arg Pro Pro Gly Glu Asn Glu Thr Tyr Leu Met Gln Phe Met Glu Glu
        530                 535                 540
Trp Gly Leu Tyr Val Gln Met Glu Asn
545                 550
```

(2) INFORMATION FOR SEQ ID NO:17:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:17:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGA CGG GCA GTT CCC TGT        96
Leu Leu Leu Leu Leu Leu Ala Ala Pro Trp Gly Arg Ala Val Pro Cys
             20                  25                  30

GTC TCT GGT GGT TTG CCT AAA CCT GCA AAC ATC ACC TTC TTA TCC ATC       144
Val Ser Gly Gly Leu Pro Lys Pro Ala Asn Ile Thr Phe Leu Ser Ile
         35                  40                  45

AAC ATG AAG AAT GTC CTA CAA TGG ACT CCA CCA GAG GGT CTT CAA GGA       192
Asn Met Lys Asn Val Leu Gln Trp Thr Pro Pro Glu Gly Leu Gln Gly
     50                  55                  60

GTT AAA GTT ACT TAC ACT GTG CAG TAT TTC ATA TAT GGG CAA AAG AAA       240
Val Lys Val Thr Tyr Thr Val Gln Tyr Phe Ile Tyr Gly Gln Lys Lys
 65                  70                  75                  80

TGG CTG AAT AAA TCA GAG TGC AGA AAT ATC AAT AGA ACC TAC TGT GAT       288
Trp Leu Asn Lys Ser Glu Cys Arg Asn Ile Asn Arg Thr Tyr Cys Asp
                 85                  90                  95

CTT TCT GCT GAG ACT TCT GAT TAC GAG CAC CAG TAT TAT GCC AAA GTT       336
Leu Ser Ala Glu Thr Ser Asp Tyr Glu His Gln Tyr Tyr Ala Lys Val
            100                 105                 110

AAG GCC ATT TGG GGA ACA AAG TGT TCC AAA TGG GCT GAG AGT GGA CGG       384
Lys Ala Ile Trp Gly Thr Lys Cys Ser Lys Trp Ala Glu Ser Gly Arg
        115                 120                 125

TTC TAT CCT TTT TTA GAG ACA CAA ATT GGC CCA CCA GAG GTG GCA CTG       432
Phe Tyr Pro Phe Leu Glu Thr Gln Ile Gly Pro Pro Glu Val Ala Leu
    130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160
```

```
TGG AAG AGA AAT CCA GAG GAT CTT CCT GTT TCC ATG CAA CAA ATA TAC      528
Trp Lys Arg Asn Pro Glu Asp Leu Pro Val Ser Met Gln Gln Ile Tyr
            165                 170                 175

TCC AAT CTG AAG TAT AAC GTG TCT GTG TTG AAT ACT AAA TCA AAC AGA      576
Ser Asn Leu Lys Tyr Asn Val Ser Val Leu Asn Thr Lys Ser Asn Arg
        180                 185                 190

ACG TGG TCC CAG TGT GTG ACC AAC CAC ACG CTG GTG CTC ACC TGG CTG      624
Thr Trp Ser Gln Cys Val Thr Asn His Thr Leu Val Leu Thr Trp Leu
            195                 200                 205

GAG CCG AAC ACT CTT TAC TGC GTA CAC GTG GAG TCC TTC GTC CCA GGG      672
Glu Pro Asn Thr Leu Tyr Cys Val His Val Glu Ser Phe Val Pro Gly
    210                 215                 220

CCC CCT CGC CGT GCT CAG CCT TCT GAG AAG CAG TGT GCC AGG ACT TTG      720
Pro Pro Arg Arg Ala Gln Pro Ser Glu Lys Gln Cys Ala Arg Thr Leu
225                 230                 235                 240

AAA GAT CAA TCA TCA GAG TTC AAG GCT AAA ATC ATC TTC TGG TAT GTT      768
Lys Asp Gln Ser Ser Glu Phe Lys Ala Lys Ile Ile Phe Trp Tyr Val
                245                 250                 255

TTG CCC ATA TCT ATT ACC GTG TTT CTT TTT TCT GTG ATG GGC TAT TCC      816
Leu Pro Ile Ser Ile Thr Val Phe Leu Phe Ser Val Met Gly Tyr Ser
            260                 265                 270

ATC TAC CGA TAT ATC CAC GTT GGC AAA GAG AAA CAC CCA GCA AAT TTG      864
Ile Tyr Arg Tyr Ile His Val Gly Lys Glu Lys His Pro Ala Asn Leu
        275                 280                 285

ATT TTG ATT TAT GGA AAT GAG TTT GAT AAA AGA TTC TTT GTG CCT GCT      912
Ile Leu Ile Tyr Gly Asn Glu Phe Asp Lys Arg Phe Phe Val Pro Ala
    290                 295                 300

GAG AAA ATC GTG ATT AAC TTT ATC ACC CTC AAT ATC TCG GAT GAT TCT      960
Glu Lys Ile Val Ile Asn Phe Ile Thr Leu Asn Ile Ser Asp Asp Ser
305                 310                 315                 320

AAA ATT TCT CAT CAG GAT ATG AGT TTA CTG GGA AAA AGC AGT GAT GTA     1008
Lys Ile Ser His Gln Asp Met Ser Leu Leu Gly Lys Ser Ser Asp Val
                325                 330                 335

TCC AGC CTT AAT GAT CCT CAG CCC AGC GGG AAC CTG AGG CCC CCT CAG     1056
Ser Ser Leu Asn Asp Pro Gln Pro Ser Gly Asn Leu Arg Pro Pro Gln
            340                 345                 350

GAG GAG GAG GAG GTG AAA CAT TTA GGG TAT GCT TCG CAT TTG ATG GAG     1104
Glu Glu Glu Glu Val Lys His Leu Gly Tyr Ala Ser His Leu Met Glu
        355                 360                 365

ATT TTT TGT GAT TCT GAG GAG AAC ACG GAG GGT ACT TCT TTC ACC CAG     1152
Ile Phe Cys Asp Ser Glu Glu Asn Thr Glu Gly Thr Ser Phe Thr Gln
    370                 375                 380

CAA GAG TCC CTC AGC AGA ACA ATA CCC CCG GAT AAA ACA GTC ATT GAG     1200
Gln Glu Ser Leu Ser Arg Thr Ile Pro Pro Asp Lys Thr Val Ile Glu
385                 390                 395                 400

TAT GAG TAT GAT GTC AGA ACC ACT GAT ATT TGT GCG GGG CCT GAG GAG     1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTA TTG     1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC     1344
Glu Ser Gln Ala Ala Leu Ala Val Leu Gly Pro Gln Thr Leu Gln Tyr
        435                 440                 445

TCA TAC ACC CCT CAG CTC CAA GAT TTA GAT CCC CTG GCG CAG GAG CAC     1392
Ser Tyr Thr Pro Gln Leu Gln Asp Leu Asp Pro Leu Ala Gln Glu His
    450                 455                 460

ACA GAT TCG GAG GAG GGG CCG GAG GAG GAG CCA TCG ACG ACC CTG GTC     1440
Thr Asp Ser Glu Glu Gly Pro Glu Glu Glu Pro Ser Thr Thr Leu Val
465                 470                 475                 480
```

```
GAT TGG GAT CCC CAA ACT GGC AGG CTG TGT ATT CCT TCG CTG TCC AGC       1488
Asp Trp Asp Pro Gln Thr Gly Arg Leu Cys Ile Pro Ser Leu Ser Ser
            485                 490                 495

TTC GAT CAG GAT TCA GAG GGC TGC GAG CCT TCT GAG GGG GAT GGG CTC       1536
Phe Asp Gln Asp Ser Glu Gly Cys Glu Pro Ser Glu Gly Asp Gly Leu
        500                 505                 510

GGA GAG GAG GGT CTT CTA TCT AGA CTC TAT GAG GAG CCG GCT CCA GAT       1584
Gly Glu Glu Gly Leu Leu Ser Arg Leu Tyr Glu Glu Pro Ala Pro Asp
        515                 520                 525

AGG CCA CCA GGA GAG AAT GAG ACC TAT CTC ATG CAA TTC ATG GAG GAG       1632
Arg Pro Pro Gly Glu Asn Glu Thr Tyr Leu Met Gln Phe Met Glu Glu
    530                 535                 540

TGG GGG TTA TAT GTG CAG ATG GAG AAC                                   1659
Trp Gly Leu Tyr Val Gln Met Glu Asn
545                 550
```

(2) INFORMATION FOR SEQ ID NO:18:

(i) SEQUENCE CHARACTERISTICS:
  (A) LENGTH: 553 amino acids
  (B) TYPE: amino acid
  (C) STRANDEDNESS: single
  (D) TOPOLOGY: linear (ii) MOLECULE TYPE: protein (v) FRAGMENT TYPE: internal (xi) SEQUENCE DESCRIPTION: SEQ ID NO:18:

```
Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125

Phe Tyr Pro Phe Leu Glu Thr Gln Ile Gly Pro Pro Glu Val Ala Leu
        130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240
```

-continued

```
Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
                260                 265                 270

Ile Tyr Arg Tyr Ile His Val Gly Lys Glu Lys His Pro Ala Asn Leu
                275                 280                 285

Ile Leu Ile Tyr Gly Asn Glu Phe Asp Lys Arg Phe Phe Val Pro Ala
                290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
                370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
                420                 425                 430

Glu Ser Gln Ala Ala Leu Ala Val Leu Gly Pro Gln Thr Leu Gln Tyr
                435                 440                 445

Ser Tyr Thr Pro Gln Leu Gln Asp Leu Asp Pro Leu Ala Gln Glu His
                450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Glu Pro Ala Pro Asp
                515                 520                 525

Arg Pro Pro Gly Glu Asn Glu Thr Tyr Leu Met Gln Phe Met Glu Glu
                530                 535                 540

Trp Gly Leu Tyr Val Gln Met Glu Asn
545                 550
```

(2) INFORMATION FOR SEQ ID NO:19:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:19:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
 1               5                  10                 15

CTG CTG CTG TTG CTC CTG GCG GCG CCT TGG GGA CGG GCA GTT CCC TGT        96
Leu Leu Leu Leu Leu Leu Ala Ala Pro Trp Gly Arg Ala Val Pro Cys
             20                  25                 30

GTC TCT GGT GGT TTG CCT AAA CCT GCA AAC ATC ACC TTT TTA TCC ATC       144
Val Ser Gly Gly Leu Pro Lys Pro Ala Asn Ile Thr Phe Leu Ser Ile
         35                  40                 45

AAC ATG AAG AAT GTC CTA CAA TGG ACT CCA CCA GAG GGT CTT CAA GGA       192
Asn Met Lys Asn Val Leu Gln Trp Thr Pro Pro Glu Gly Leu Gln Gly
     50                  55                 60

GTT AAA GTT ACT TAC ACT GTG CAG TAT TTT ATA TAT GGG CAA AAG AAA       240
Val Lys Val Thr Tyr Thr Val Gln Tyr Phe Ile Tyr Gly Gln Lys Lys
 65                  70                 75                 80

TGG CTG AAT AAA TCA GAG TGC AGA AAT ATC AAT AGA ACC TAC TGT GAT       288
Trp Leu Asn Lys Ser Glu Cys Arg Asn Ile Asn Arg Thr Tyr Cys Asp
                 85                  90                 95

CTT TCT GCT GAG ACT TCT GAC TAC GAG CAC CAG TAT TAT GCC AAA GTT       336
Leu Ser Ala Glu Thr Ser Asp Tyr Glu His Gln Tyr Tyr Ala Lys Val
             100                 105                110

AAG GCC ATT TGG GGA ACA AAG TGT TCC AAA TGG GCT GAG AGT GGA CGG       384
Lys Ala Ile Trp Gly Thr Lys Cys Ser Lys Trp Ala Glu Ser Gly Arg
         115                 120                 125

TTT TAT CCT TTT TTA GAG ACA CAA ATT GGC CCA CCA GAG GTG GCA CTG       432
Phe Tyr Pro Phe Leu Glu Thr Gln Ile Gly Pro Pro Glu Val Ala Leu
     130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160

TGG AAG AGA AAT CCA GAG GAC CTT CCT GTT TCC ATG CAA CAA ATA TAC       528
Trp Lys Arg Asn Pro Glu Asp Leu Pro Val Ser Met Gln Gln Ile Tyr
                 165                 170                 175

TCC AAT CTG AAG TAT AAC GTG TCT GTG TTG AAT ACT AAA TCA AAC AGA       576
Ser Asn Leu Lys Tyr Asn Val Ser Val Leu Asn Thr Lys Ser Asn Arg
             180                 185                 190

ACG TGG TCC CAG TGT GTG ACC AAC CAC ACG CTG GTG CTC ACC TGG CTG       624
Thr Trp Ser Gln Cys Val Thr Asn His Thr Leu Val Leu Thr Trp Leu
         195                 200                 205

GAG CCG AAC ACT CTT TAC TGC GTA CAC GTG GAG TCC TTT GTC CCA GGG       672
Glu Pro Asn Thr Leu Tyr Cys Val His Val Glu Ser Phe Val Pro Gly
     210                 215                 220

CCC CCT CGC CGT GCT CAG CCT TCT GAG AAG CAG TGT GCC AGG ACT TTG       720
Pro Pro Arg Arg Ala Gln Pro Ser Glu Lys Gln Cys Ala Arg Thr Leu
225                 230                 235                 240

AAA GAT CAA TCA TCA GAG TTT AAG GCT AAA ATC ATC TTT TGG TAT GTT       768
Lys Asp Gln Ser Ser Glu Phe Lys Ala Lys Ile Ile Phe Trp Tyr Val
                 245                 250                 255

TTG CCC ATA TCT ATT ACC GTG TTT CTT TTT TCT GTG ATG GGC TAT TCC       816
Leu Pro Ile Ser Ile Thr Val Phe Leu Phe Ser Val Met Gly Tyr Ser
             260                 265                 270

ATC TAC CGA TAT ATC CAC GTT GGC AAA GAG AAA CAC CCA GCA AAT TTG       864
Ile Tyr Arg Tyr Ile His Val Gly Lys Glu Lys His Pro Ala Asn Leu
         275                 280                 285

ATT TTG ATT TAT GGA AAT GAG TTT GAC AAA AGA TTT TTT GTG CCT GCT       912
Ile Leu Ile Tyr Gly Asn Glu Phe Asp Lys Arg Phe Phe Val Pro Ala
     290                 295                 300

GAG AAA ATC GTG ATT AAC TTT ATC ACC CTC AAT ATC TCG GAT GAT TCT       960
Glu Lys Ile Val Ile Asn Phe Ile Thr Leu Asn Ile Ser Asp Asp Ser
305                 310                 315                 320
```

```
AAA ATT TCT CAT CAG GAT ATG AGT TTA CTG GGA AAA AGC AGT GAT GTA        1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG        1056
Ser Ser Leu Asn Asp Pro Gln Pro Ser Gly Asn Leu Arg Pro Pro Gln
        340                 345                 350

GAG GAG GAG GAG GTG AAA CAT TTA GGG TAT GCT TCG CAT TTG ATG GAG        1104
Glu Glu Glu Glu Val Lys His Leu Gly Tyr Ala Ser His Leu Met Glu
                355                 360                 365

ATT TTT TGT GAC TCT GAG GAG AAC ACG GAG GGT ACT TCT TTT ACC CAG        1152
Ile Phe Cys Asp Ser Glu Glu Asn Thr Glu Gly Thr Ser Phe Thr Gln
370                 375                 380

CAA GAG TCC CTC AGC AGA ACA ATA CCC CCG GAT AAA ACA GTC ATT GAG        1200
Gln Glu Ser Leu Ser Arg Thr Ile Pro Pro Asp Lys Thr Val Ile Glu
385                 390                 395                 400

TAT GAG TAT GAT GTC AGA ACC ACT GAC ATT TGT GCG GGG CCT GAG GAG        1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTA TTG        1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC        1344
Glu Ser Gln Ala Ala Leu Ala Val Leu Gly Pro Gln Thr Leu Gln Tyr
        435                 440                 445

TCA TAC ACC CCT CAG CTC CAA GAC TTA GAC CCC CTG GCG CAG GAG CAC        1392
Ser Tyr Thr Pro Gln Leu Gln Asp Leu Asp Pro Leu Ala Gln Glu His
    450                 455                 460

ACA GAC TCG GAG GAG GGG CCG GAG GAG GAG CCA TCG ACG ACC CTG GTC        1440
Thr Asp Ser Glu Glu Gly Pro Glu Glu Glu Pro Ser Thr Thr Leu Val
465                 470                 475                 480

GAC TGG GAT CCC CAA ACT GGC AGG CTG TGT ATT CCT TCG CTG TCC AGC        1488
Asp Trp Asp Pro Gln Thr Gly Arg Leu Cys Ile Pro Ser Leu Ser Ser
                485                 490                 495

TTT GAC CAG GAT TCA GAG GGC TGC GAG CCT TCT GAG GGG GAT GGG CTC        1536
Phe Asp Gln Asp Ser Glu Gly Cys Glu Pro Ser Glu Gly Asp Gly Leu
            500                 505                 510

GGA GAG GAG GGT CTT CTA TCT AGA CTC TAT GAG GAG CCG GCT CCA GAC        1584
Gly Glu Glu Gly Leu Leu Ser Arg Leu Tyr Glu Glu Pro Ala Pro Asp
        515                 520                 525

AGG CCA CCA GGA GAG AAT GAG ACC TAT CTC ATG CAA TTT ATG GAG GAG        1632
Arg Pro Pro Gly Glu Asn Glu Thr Tyr Leu Met Gln Phe Met Glu Glu
    530                 535                 540

TGG GGG TTA TAT GTG CAG ATG GAG AAC                                    1659
Trp Gly Leu Tyr Val Gln Met Glu Asn
545                 550
```

(2) INFORMATION FOR SEQ ID NO:20:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:20:

```
Met Arg Ala Pro Gly Arg Pro Ala Leu Arg Pro Leu Pro Leu Pro Pro
 1               5                  10                  15

Leu Leu Leu Leu Leu Ala Ala Pro Trp Gly Arg Ala Val Pro Cys
             20                  25                  30
```

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
 65              70                  75                      80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
             100                 105                 110

Lys Ala Ile Trp Gly Thr Lys Cys Ser Lys Trp Ala Glu Ser Gly Arg
             115                 120                 125

Phe Tyr Pro Phe Leu Glu Thr Gln Ile Gly Pro Pro Glu Val Ala Leu
             130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                 165                 170                 175

Ser Asn Leu Lys Tyr Asn Val Ser Val Leu Asn Thr Lys Ser Asn Arg
             180                 185                 190

Thr Trp Ser Gln Cys Val Thr Asn His Thr Leu Val Leu Thr Trp Leu
             195                 200                 205

Glu Pro Asn Thr Leu Tyr Cys Val His Val Glu Ser Phe Val Pro Gly
210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                 245                 250                 255

Leu Pro Ile Ser Ile Thr Val Phe Leu Phe Ser Val Met Gly Tyr Ser
             260                 265                 270

Ile Tyr Arg Tyr Ile His Val Gly Lys Glu Lys His Pro Ala Asn Leu
             275                 280                 285

Ile Leu Ile Tyr Gly Asn Glu Phe Asp Lys Arg Phe Phe Val Pro Ala
290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                 325                 330                 335

Ser Ser Leu Asn Asp Pro Gln Pro Ser Gly Asn Leu Arg Pro Pro Gln
             340                 345                 350

Glu Glu Glu Glu Val Lys His Leu Gly Tyr Ala Ser His Leu Met Glu
             355                 360                 365

Ile Phe Cys Asp Ser Glu Glu Asn Thr Glu Gly Thr Ser Phe Thr Gln
             370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                 405                 410                 415

Gln Glu Leu Ser Leu Gln Glu Glu Val Ser Thr Gln Gly Thr Leu Leu
             420                 425                 430

Glu Ser Gln Ala Ala Leu Ala Val Leu Gly Pro Gln Thr Leu Gln Tyr
             435                 440                 445
```

```
Ser Tyr Thr Pro Gln Leu Gln Asp Leu Asp Pro Leu Ala Gln Glu His
    450                 455                 460

Thr Asp Ser Glu Glu Gly Pro Glu Glu Glu Pro Ser Thr Thr Leu Val
465                 470                 475                 480

Asp Trp Asp Pro Gln Thr Gly Arg Leu Cys Ile Pro Ser Leu Ser Ser
                    485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Glu Pro Ala Pro Asp
            515                 520                 525

Arg Pro Pro Gly Glu Asn Glu Thr Tyr Leu Met Gln Phe Met Glu Glu
        530                 535                 540

Trp Gly Leu Tyr Val Gln Met Glu Asn
545                 550
```

(2) INFORMATION FOR SEQ ID NO:21:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:21:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGC CGG GCA GTT CCC TGT        96
Leu Leu Leu Leu Leu Leu Ala Ala Pro Trp Gly Arg Ala Val Pro Cys
                20                  25                  30

GTC TCT GGT GGT TTG CCT AAA CCT GCA AAC ATC ACC TTT TTA TCC ATC       144
Val Ser Gly Gly Leu Pro Lys Pro Ala Asn Ile Thr Phe Leu Ser Ile
            35                  40                  45

AAC ATG AAG AAT GTC CTA CAA TGG ACT CCA CCA GAG GGT CTT CAA GGC       192
Asn Met Lys Asn Val Leu Gln Trp Thr Pro Pro Glu Gly Leu Gln Gly
        50                  55                  60

GTT AAA GTT ACT TAC ACT GTG CAG TAT TTT ATA TAT GGG CAA AAG AAA       240
Val Lys Val Thr Tyr Thr Val Gln Tyr Phe Ile Tyr Gly Gln Lys Lys
65                  70                  75                  80

TGG CTG AAT AAA TCA GAA TGC AGA AAT ATC AAT AGA ACC TAC TGT GAT       288
Trp Leu Asn Lys Ser Glu Cys Arg Asn Ile Asn Arg Thr Tyr Cys Asp
                85                  90                  95

CTT TCT GCT GAA ACT TCT GAC TAC GAA CAC CAG TAT TAT GCC AAA GTT       336
Leu Ser Ala Glu Thr Ser Asp Tyr Glu His Gln Tyr Tyr Ala Lys Val
                100                 105                 110

AAG GCC ATT TGG GGC ACA AAG TGT TCC AAA TGG GCT GAA AGT GGC CGG       384
Lys Ala Ile Trp Gly Thr Lys Cys Ser Lys Trp Ala Glu Ser Gly Arg
            115                 120                 125

TTT TAT CCT TTT TTA GAA ACA CAA ATT GGC CCA CCA GAG GTG GCA CTG       432
Phe Tyr Pro Phe Leu Glu Thr Gln Ile Gly Pro Pro Glu Val Ala Leu
        130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160
```

```
TGG AAG AGA AAT CCA GAA GAC CTT CCT GTT TCC ATG CAA CAA ATA TAC      528
Trp Lys Arg Asn Pro Glu Asp Leu Pro Val Ser Met Gln Gln Ile Tyr
            165                 170                 175

TCC AAT CTG AAG TAT AAC GTG TCT GTG TTG AAT ACT AAA TCA AAC AGA      576
Ser Asn Leu Lys Tyr Asn Val Ser Val Leu Asn Thr Lys Ser Asn Arg
        180                 185                 190

ACG TGG TCC CAG TGT GTG ACC AAC CAC ACG CTG GTG CTC ACC TGG CTG      624
Thr Trp Ser Gln Cys Val Thr Asn His Thr Leu Val Leu Thr Trp Leu
                195                 200                 205

GAG CCG AAC ACT CTT TAC TGC GTA CAC GTG GAG TCC TTT GTC CCA GGG      672
Glu Pro Asn Thr Leu Tyr Cys Val His Val Glu Ser Phe Val Pro Gly
    210                 215                 220

CCC CCT CGC CGT GCT CAG CCT TCT GAG AAG CAG TGT GCC AGG ACT TTG      720
Pro Pro Arg Arg Ala Gln Pro Ser Glu Lys Gln Cys Ala Arg Thr Leu
225                 230                 235                 240

AAA GAT CAA TCA TCA GAG TTT AAG GCT AAA ATC ATC TTT TGG TAT GTT      768
Lys Asp Gln Ser Ser Glu Phe Lys Ala Lys Ile Ile Phe Trp Tyr Val
                245                 250                 255

TTG CCC ATA TCT ATT ACC GTG TTT CTT TTT TCT GTG ATG GGC TAT TCC      816
Leu Pro Ile Ser Ile Thr Val Phe Leu Phe Ser Val Met Gly Tyr Ser
            260                 265                 270

ATC TAC CGA TAT ATC CAC GTT GGC AAA GAG AAA CAC CCA GCA AAT TTG      864
Ile Tyr Arg Tyr Ile His Val Gly Lys Glu Lys His Pro Ala Asn Leu
        275                 280                 285

ATT TTG ATT TAT GGC AAT GAA TTT GAC AAA AGA TTT TTT GTG CCT GCT      912
Ile Leu Ile Tyr Gly Asn Glu Phe Asp Lys Arg Phe Phe Val Pro Ala
                290                 295                 300

GAA AAA ATC GTG ATT AAC TTT ATC ACC CTC AAT ATC TCG GAT GAT TCT      960
Glu Lys Ile Val Ile Asn Phe Ile Thr Leu Asn Ile Ser Asp Asp Ser
305                 310                 315                 320

AAA ATT TCT CAT CAG GAT ATG AGT TTA CTG GGC AAA AGC AGT GAT GTA     1008
Lys Ile Ser His Gln Asp Met Ser Leu Leu Gly Lys Ser Ser Asp Val
                325                 330                 335

TCC AGC CTT AAT GAT CCT CAG CCC AGC GGG AAC CTG AGG CCC CCT CAG     1056
Ser Ser Leu Asn Asp Pro Gln Pro Ser Gly Asn Leu Arg Pro Pro Gln
            340                 345                 350

GAG GAA GAG GAG GTG AAA CAT TTA GGG TAT GCT TCG CAT TTG ATG GAA     1104
Glu Glu Glu Glu Val Lys His Leu Gly Tyr Ala Ser His Leu Met Glu
        355                 360                 365

ATT TTT TGT GAC TCT GAA GAA AAC ACG GAA GGT ACT TCT TTT ACC CAG     1152
Ile Phe Cys Asp Ser Glu Glu Asn Thr Glu Gly Thr Ser Phe Thr Gln
                370                 375                 380

CAA GAG TCC CTC AGC AGA ACA ATA CCC CCG GAT AAA ACA GTC ATT GAA     1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GA G    1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGC ACA TTA T TG    1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC     1344
Glu Ser Gln Ala Ala Leu Ala Val Leu Gly Pro Gln Thr Leu Gln Tyr
        435                 440                 445

TCA TAC ACC CCT CAG CTC CAA GAC TTA GAC CCC CTG GCG CAG GAG CAC     1392
Ser Tyr Thr Pro Gln Leu Gln Asp Leu Asp Pro Leu Ala Gln Glu His
                450                 455                 460

ACA GAC TCG GAG GAG GGG CCG GAG GAA GAG CCA TCG ACG ACC CT G GTC   1440
Thr Asp Ser Glu Glu Gly Pro Glu Glu Glu Pro Ser Thr Thr Leu Val
465                 470                 475                 480
```

```
GAC TGG GAT CCC CAA ACT GGC AGG CTG TGT ATT CCT TCG CTG T CC AGC    1488
Asp Trp Asp Pro Gln Thr Gly Arg Leu Cys Ile Pro Ser Leu Ser Ser
                485                 490                 495

TTT GAC CAG GAT TCA GAG GGC TGC GAG CCT TCT GAG GGG GAT GGG CTC     1536
Phe Asp Gln Asp Ser Glu Gly Cys Glu Pro Ser Glu Gly Asp Gly Leu
                500                 505                 510

GGC GAG GAG GGT CTT CTA TCT AGA CTC TAT GAG GAG CCG GCT CCA GAC     1584
Gly Glu Glu Gly Leu Leu Ser Arg Leu Tyr Glu Glu Pro Ala Pro Asp
                515                 520                 525

AGG CCA CCA GGC GAA AAT GAA ACC TAT CTC ATG CAA TTT ATG GAG GAA     1632
Arg Pro Pro Gly Glu Asn Glu Thr Tyr Leu Met Gln Phe Met Glu Glu
        530                 535                 540

TGG GGG TTA TAT GTG CAG ATG GAA AAC                                 1659
Trp Gly Leu Tyr Val Gln Met Glu Asn
545                 550
```

(2) INFORMATION FOR SEQ ID NO:22:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:22:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
                20                  25                  30

Val Ser Gly Gly Leu Pro Lys Pro Ala Asn Ile Thr Phe Leu Ser Ile
                35                  40                  45

Asn Met Lys Asn Val Leu Gln Trp Thr Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240
```

| | | | | | | | | | | | |
|---|---|---|---|---|---|---|---|---|---|---|---|
| Lys | Asp | Gln | Ser | Ser | Glu | Phe | Lys | Ala | Lys | Ile | Ile | Phe | Trp | Tyr | Val |
| | | | 245 | | | | | 250 | | | | | 255 | | |
| Leu | Pro | Ile | Ser | Ile | Thr | Val | Phe | Leu | Phe | Ser | Val | Met | Gly | Tyr | Ser |
| | | | 260 | | | | | 265 | | | | | 270 | | |
| Ile | Tyr | Arg | Tyr | Ile | His | Val | Gly | Lys | Glu | Lys | His | Pro | Ala | Asn | Leu |
| | | | 275 | | | | | 280 | | | | | 285 | | |
| Ile | Leu | Ile | Tyr | Gly | Asn | Glu | Phe | Asp | Lys | Arg | Phe | Phe | Val | Pro | Ala |
| | | | 290 | | | | | 295 | | | | | 300 | | |
| Glu | Lys | Ile | Val | Ile | Asn | Phe | Ile | Thr | Leu | Asn | Ile | Ser | Asp | Asp | Ser |
| 305 | | | | | 310 | | | | | 315 | | | | | 320 |

Lys Ile Ser His Gln Asp Met Ser Leu Leu Gly Lys Ser Ser Asp Val
                    325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
                420                 425                 430

Glu Ser Gln Ala Ala Leu Ala Val Leu Gly Pro Gln Thr Leu Gln Tyr
                435                 440                 445

Ser Tyr Thr Pro Gln Leu Gln Asp Leu Asp Pro Leu Ala Gln Glu His
                450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Glu Pro Ala Pro Asp
                515                 520                 525

Arg Pro Pro Gly Glu Asn Glu Thr Tyr Leu Met Gln Phe Met Glu Glu
                530                 535                 540

Trp Gly Leu Tyr Val Gln Met Glu Asn
545                 550

(2) INFORMATION FOR SEQ ID NO:23:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:23:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGC CGG GCA GTT CCC TGT        96
Leu Leu Leu Leu Leu Leu Ala Ala Pro Trp Gly Arg Ala Val Pro Cys
             20                  25                  30

GTC TCT GGT GGT TTG CCT AAA CCT GCA AAC ATC ACC TTC TTA TCC ATC       144
Val Ser Gly Gly Leu Pro Lys Pro Ala Asn Ile Thr Phe Leu Ser Ile
         35                  40                  45

AAC ATG AAG AAT GTC CTA CAA TGG ACT CCA CCA GAG GGT CTT CAA GGC       192
Asn Met Lys Asn Val Leu Gln Trp Thr Pro Pro Glu Gly Leu Gln Gly
     50                  55                  60

GTT AAA GTT ACT TAC ACT GTG CAG TAT TTC ATA TAT GGG CAA AAG AAA       240
Val Lys Val Thr Tyr Thr Val Gln Tyr Phe Ile Tyr Gly Gln Lys Lys
 65                  70                  75                  80

TGG CTG AAT AAA TCA GAA TGC AGA AAT ATC AAT AGA ACC TAC TGT GAT       288
Trp Leu Asn Lys Ser Glu Cys Arg Asn Ile Asn Arg Thr Tyr Cys Asp
                 85                  90                  95

CTT TCT GCT GAA ACT TCT GAC TAC GAA CAT CAG TAT TAT GCC AAA GTT       336
Leu Ser Ala Glu Thr Ser Asp Tyr Glu His Gln Tyr Tyr Ala Lys Val
             100                 105                 110

AAG GCC ATT TGG GGC ACA AAG TGT TCC AAA TGG GCT GAA AGT GGC CGG       384
Lys Ala Ile Trp Gly Thr Lys Cys Ser Lys Trp Ala Glu Ser Gly Arg
         115                 120                 125

TTC TAT CCT TTT TTA GAA ACA CAA ATT GGC CCA CCA GAG GTG GCA CTG       432
Phe Tyr Pro Phe Leu Glu Thr Gln Ile Gly Pro Pro Glu Val Ala Leu
     130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160

TGG AAG AGA AAT CCA GAA GAC CTT CCT GTT TCC ATG CAA CAA ATA TAC       528
Trp Lys Arg Asn Pro Glu Asp Leu Pro Val Ser Met Gln Gln Ile Tyr
                 165                 170                 175

TCC AAT CTG AAG TAT AAC GTG TCT GTG TTG AAT ACT AAA TCA AAC AGA       576
Ser Asn Leu Lys Tyr Asn Val Ser Val Leu Asn Thr Lys Ser Asn Arg
             180                 185                 190

ACG TGG TCC CAG TGT GTG ACC AAC CAT ACG CTG GTG CTC ACC TGG CTG       624
Thr Trp Ser Gln Cys Val Thr Asn His Thr Leu Val Leu Thr Trp Leu
         195                 200                 205

GAG CCG AAC ACT CTT TAC TGC GTA CAT GTG GAG TCC TTC GTC CCA GGG       672
Glu Pro Asn Thr Leu Tyr Cys Val His Val Glu Ser Phe Val Pro Gly
     210                 215                 220

CCC CCT CGC CGT GCT CAG CCT TCT GAG AAG CAG TGT GCC AGG ACT TTG       720
Pro Pro Arg Arg Ala Gln Pro Ser Glu Lys Gln Cys Ala Arg Thr Leu
225                 230                 235                 240

AAA GAT CAA TCA TCA GAG TTC AAG GCT AAA ATC ATC TTC TGG TAT GTT       768
Lys Asp Gln Ser Ser Glu Phe Lys Ala Lys Ile Ile Phe Trp Tyr Val
                 245                 250                 255

TTG CCC ATA TCT ATT ACC GTG TTT CTT TTT TCT GTG ATG GGC TAT TCC       816
Leu Pro Ile Ser Ile Thr Val Phe Leu Phe Ser Val Met Gly Tyr Ser
             260                 265                 270

ATC TAC CGA TAT ATC CAT GTT GGC AAA GAG AAA CAT CCA GCA AAT TTG       864
Ile Tyr Arg Tyr Ile His Val Gly Lys Glu Lys His Pro Ala Asn Leu
         275                 280                 285

ATT TTG ATT TAT GGC AAT GAA TTT GAC AAA AGA TTC TTT GTG CCT GCT       912
Ile Leu Ile Tyr Gly Asn Glu Phe Asp Lys Arg Phe Phe Val Pro Ala
     290                 295                 300

GAA AAA ATC GTG ATT AAC TTT ATC ACC CTC AAT ATC TCG GAT GAT TCT       960
Glu Lys Ile Val Ile Asn Phe Ile Thr Leu Asn Ile Ser Asp Asp Ser
305                 310                 315                 320
```

```
AAA ATT TCT CAT CAG GAT ATG AGT TTA CTG GGC AAA AGC AGT GAT GTA      1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG      1056
Ser Ser Leu Asn Asp Pro Gln Pro Ser Gly Asn Leu Arg Pro Pro Gln
                340                 345                 350

GAG GAA GAG GAG GTG AAA CAT TTA GGG TAT GCT TCG CAT TTG ATG GAA      1104
Glu Glu Glu Glu Val Lys His Leu Gly Tyr Ala Ser His Leu Met Glu
                    355                 360                 365

ATT TTT TGT GAC TCT GAA GAA AAC ACG GAA GGT ACT TCT TTC ACC CAG      1152
Ile Phe Cys Asp Ser Glu Glu Asn Thr Glu Gly Thr Ser Phe Thr Gln
            370                 375                 380

CAA GAG TCC CTC AGC AGA ACA ATA CCC CCG GAT AAA ACA GTC ATT GAA      1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG      1248
Tyr Glu Tyr Asp Val Arg Thr Thr Asp Ile Cys Ala Gly Pro Glu Glu
                    405                 410                 415

CAG GAG CTC AGT TTG CAG GAG GAG GTG TCC ACA CAA GGC ACA TTA TTG      1296
Gln Glu Leu Ser Leu Gln Glu Glu Val Ser Thr Gln Gly Thr Leu Leu
                420                 425                 430

GAG TCG CAG GCA GCG TTG GCA GTC TTG GGC CCG CAA ACG TTA CAG TAC      1344
Glu Ser Gln Ala Ala Leu Ala Val Leu Gly Pro Gln Thr Leu Gln Tyr
            435                 440                 445

TCA TAC ACC CCT CAG CTC CAA GAC TTA GAC CCC CTG GCG CAG GAG CAT      1392
Ser Tyr Thr Pro Gln Leu Gln Asp Leu Asp Pro Leu Ala Gln Glu His
            450                 455                 460

ACA GAC TCG GAG GAG GGG CCG GAG GAA GAG CCA TCG ACG ACC CTG GTC      1440
Thr Asp Ser Glu Glu Gly Pro Glu Glu Glu Pro Ser Thr Thr Leu Val
465                 470                 475                 480

GAC TGG GAT CCC CAA ACT GGC AGG CTG TGT ATT CCT TCG CTG TCC AGC      1488
Asp Trp Asp Pro Gln Thr Gly Arg Leu Cys Ile Pro Ser Leu Ser Ser
                485                 490                 495

TTC GAC CAG GAT TCA GAG GGC TGC GAG CCT TCT GAG GGG GAT GGG CTC      1536
Phe Asp Gln Asp Ser Glu Gly Cys Glu Pro Ser Glu Gly Asp Gly Leu
            500                 505                 510

GGC GAG GAG GGT CTT CTA TCT AGA CTC TAT GAG GAG CCG GCT CCA GAC      1584
Gly Glu Glu Gly Leu Leu Ser Arg Leu Tyr Glu Glu Pro Ala Pro Asp
            515                 520                 525

AGG CCA CCA GGC GAA AAT GAA ACC TAT CTC ATG CAA TTC ATG GAG GAA      1632
Arg Pro Pro Gly Glu Asn Glu Thr Tyr Leu Met Gln Phe Met Glu Glu
            530                 535                 540

TGG GGG TTA TAT GTG CAG ATG GAA AAC                                  1659
Trp Gly Leu Tyr Val Gln Met Glu Asn
545                 550
```

(2) INFORMATION FOR SEQ ID NO:24:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:24:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30
```

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
         50                  55                  60

Val Lys Val Thr Tyr Thr Val Gln Tyr Phe Ile Tyr Gly Gln Lys Lys
 65              70                  75                  80

Trp Leu Asn Lys Ser Glu Cys Arg Asn Ile Asn Arg Thr Tyr Cys Asp
             85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
                180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
            210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Phe Val Pro Ala
            290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
            355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
            435                 440                 445
```

```
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                    485                 490                 495
Phe Asp Gln Asp Ser Glu Gly Cys Glu Pro Ser Glu Gly Asp Gly Leu
                500                 505                 510
Gly Glu Glu Gly Leu Leu Ser Arg Leu Tyr Glu Glu Pro Ala Pro Asp
                515                 520                 525
Arg Pro Pro Gly Glu Asn Glu Thr Tyr Leu Met Gln Phe Met Glu Glu
                530                 535                 540
Trp Gly Leu Tyr Val Gln Met Glu Asn
545                 550
```

(2) INFORMATION FOR SEQ ID NO:25:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:25:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGA CGG GCA GTT CCC TGT        96
Leu Leu Leu Leu Leu Leu Ala Ala Pro Trp Gly Arg Ala Val Pro Cys
            20                  25                  30

GTC TCT GGT GGT TTG CCT AAA CCT GCA AAC ATC ACC TTC TTA TCC ATC       144
Val Ser Gly Gly Leu Pro Lys Pro Ala Asn Ile Thr Phe Leu Ser Ile
        35                  40                  45

AAC ATG AAG AAT GTC CTA CAA TGG ACT CCA CCA GAG GGT CTT CAA GGA       192
Asn Met Lys Asn Val Leu Gln Trp Thr Pro Pro Glu Gly Leu Gln Gly
    50                  55                  60

GTT AAA GTT ACT TAC ACT GTG CAG TAT TTC ATC TAT GGG CAA AAG AAA       240
Val Lys Val Thr Tyr Thr Val Gln Tyr Phe Ile Tyr Gly Gln Lys Lys
65                  70                  75                  80

TGG CTG AAT AAA TCA GAA TGC AGA AAT ATC AAT AGA ACC TAC TGT GAT       288
Trp Leu Asn Lys Ser Glu Cys Arg Asn Ile Asn Arg Thr Tyr Cys Asp
                85                  90                  95

CTT TCT GCT GAA ACT TCT GAC TAC GAA CAT CAG TAT TAT GCC AAA GTT       336
Leu Ser Ala Glu Thr Ser Asp Tyr Glu His Gln Tyr Tyr Ala Lys Val
            100                 105                 110

AAG GCC ATT TGG GGA ACA AAG TGT TCC AAA TGG GCT GAA AGT GGA CGG       384
Lys Ala Ile Trp Gly Thr Lys Cys Ser Lys Trp Ala Glu Ser Gly Arg
        115                 120                 125

TTC TAT CCT TTT TTA GAA ACA CAA ATT GGC CCA CCA GAG GTG GCA CTG       432
Phe Tyr Pro Phe Leu Glu Thr Gln Ile Gly Pro Pro Glu Val Ala Leu
    130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160
```

| | | |
|---|---|---|
| TGG AAG AGA AAT CCA GAA GAC CTT CCT GTT TCC ATG CAA CAA ATC TAC<br>Trp Lys Arg Asn Pro Glu Asp Leu Pro Val Ser Met Gln Gln Ile Tyr<br>165 170 175 | | 528 |
| TCC AAT CTG AAG TAT AAC GTG TCT GTG TTG AAT ACT AAA TCA AAC AGA<br>Ser Asn Leu Lys Tyr Asn Val Ser Val Leu Asn Thr Lys Ser Asn Arg<br>180 185 190 | | 576 |
| ACG TGG TCC CAG TGT GTG ACC AAC CAT ACG CTG GTG CTC ACC TGG CTG<br>Thr Trp Ser Gln Cys Val Thr Asn His Thr Leu Val Leu Thr Trp Leu<br>195 200 205 | | 624 |
| GAG CCG AAC ACT CTT TAC TGC GTA CAT GTG GAG TCC TTC GTC CCA GGG<br>Glu Pro Asn Thr Leu Tyr Cys Val His Val Glu Ser Phe Val Pro Gly<br>210 215 220 | | 672 |
| CCC CCT CGC CGT GCT CAG CCT TCT GAG AAG CAG TGT GCC AGG ACT TTG<br>Pro Pro Arg Arg Ala Gln Pro Ser Glu Lys Gln Cys Ala Arg Thr Leu<br>225 230 235 240 | | 720 |
| AAA GAT CAA TCA TCA GAG TTC AAG GCT AAA ATC ATC TTC TGG TAT GTT<br>Lys Asp Gln Ser Ser Glu Phe Lys Ala Lys Ile Ile Phe Trp Tyr Val<br>245 250 255 | | 768 |
| TTG CCC ATC TCT ATT ACC GTG TTT CTT TTT TCT GTG ATG GGC TAT TCC<br>Leu Pro Ile Ser Ile Thr Val Phe Leu Phe Ser Val Met Gly Tyr Ser<br>260 265 270 | | 816 |
| ATC TAC CGA TAT ATC CAT GTT GGC AAA GAG AAA CAT CCA GCA AAT TTG<br>Ile Tyr Arg Tyr Ile His Val Gly Lys Glu Lys His Pro Ala Asn Leu<br>275 280 285 | | 864 |
| ATT TTG ATT TAT GGA AAT GAA TTT GAC AAA AGA TTC TTT GTG CCT GCT<br>Ile Leu Ile Tyr Gly Asn Glu Phe Asp Lys Arg Phe Phe Val Pro Ala<br>290 295 300 | | 912 |
| GAA AAA ATC GTG ATT AAC TTT ATC ACC CTC AAT ATC TCG GAT GAT TCT<br>Glu Lys Ile Val Ile Asn Phe Ile Thr Leu Asn Ile Ser Asp Asp Ser<br>305 310 315 320 | | 960 |
| AAA ATT TCT CAT CAG GAT ATG AGT TTA CTG GGA AAA AGC AGT GAT GTA<br>Lys Ile Ser His Gln Asp Met Ser Leu Leu Gly Lys Ser Ser Asp Val<br>325 330 335 | | 1008 |
| TCC AGC CTT AAT GAT CCT CAG CCC AGC GGG AAC CTG AGG CCC CCT CAG<br>Ser Ser Leu Asn Asp Pro Gln Pro Ser Gly Asn Leu Arg Pro Pro Gln<br>340 345 350 | | 1056 |
| GAG GAA GAG GAG GTG AAA CAT TTA GGG TAT GCT TCG CAT TTG ATG GAA<br>Glu Glu Glu Glu Val Lys His Leu Gly Tyr Ala Ser His Leu Met Glu<br>355 360 365 | | 1104 |
| ATT TTT TGT GAC TCT GAA GAA AAC ACG GAA GGT ACT TCT TTC ACC CAG<br>Ile Phe Cys Asp Ser Glu Glu Asn Thr Glu Gly Thr Ser Phe Thr Gln<br>370 375 380 | | 1152 |
| CAA GAG TCC CTC AGC AGA ACA ATC CCC CCG GAT AAA ACA GTC ATT GAA<br>Gln Glu Ser Leu Ser Arg Thr Ile Pro Pro Asp Lys Thr Val Ile Glu<br>385 390 395 400 | | 1200 |
| TAT GAA TAT GAT GTC AGA ACC ACT GAC ATT TGT GCG GGG CCT GAA GAG<br>Tyr Glu Tyr Asp Val Arg Thr Thr Asp Ile Cys Ala Gly Pro Glu Glu<br>405 410 415 | | 1248 |
| CAG GAG CTC AGT TTG CAG GAG GAG GTG TCC ACA CAA GGA ACA TTA TTG<br>Gln Glu Leu Ser Leu Gln Glu Glu Val Ser Thr Gln Gly Thr Leu Leu<br>420 425 430 | | 1296 |
| GAG TCG CAG GCA GCG TTG GCA GTC TTG GGC CCG CAA ACG TTA CAG TAC<br>Glu Ser Gln Ala Ala Leu Ala Val Leu Gly Pro Gln Thr Leu Gln Tyr<br>435 440 445 | | 1344 |
| TCA TAC ACC CCT CAG CTC CAA GAC TTA GAC CCC CTG GCG CAG GAG CAT<br>Ser Tyr Thr Pro Gln Leu Gln Asp Leu Asp Pro Leu Ala Gln Glu His<br>450 455 460 | | 1392 |
| ACA GAC TCG GAG GAG GGG CCG GAG GAA GAG CCA TCG ACG ACC CTG GTC<br>Thr Asp Ser Glu Glu Gly Pro Glu Glu Glu Pro Ser Thr Thr Leu Val<br>465 470 475 480 | | 1440 |

```
GAC TGG GAT CCC CAA ACT GGC AGG CTG TGT ATT CCT TCG CTG TCC AGC       1488
Asp Trp Asp Pro Gln Thr Gly Arg Leu Cys Ile Pro Ser Leu Ser Ser
                485                 490                 495

TTC GAC CAG GAT TCA GAG GGC TGC GAG CCT TCT GAG GGG GAT GGG CTC       1536
Phe Asp Gln Asp Ser Glu Gly Cys Glu Pro Ser Glu Gly Asp Gly Leu
                500                 505                 510

GGA GAG GAG GGT CTT CTA TCT AGA CTC TAT GAG GAG CCG GCT CCA GAC       1584
Gly Glu Glu Gly Leu Leu Ser Arg Leu Tyr Glu Glu Pro Ala Pro Asp
                515                 520                 525

AGG CCA CCA GGA GAA AAT GAA ACC TAT CTC ATG CAA TTC ATG GAG GAA       1632
Arg Pro Pro Gly Glu Asn Glu Thr Tyr Leu Met Gln Phe Met Glu Glu
        530                 535                 540

TGG GGG TTA TAT GTG CAG ATG GAA AAC                                    1659
Trp Gly Leu Tyr Val Gln Met Glu Asn
545                 550
```

(2) INFORMATION FOR SEQ ID NO:26:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:26:

```
Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240
```

-continued

```
Lys Asp Gln Ser Ser Glu Phe Lys Ala Lys Ile Ile Phe Trp Tyr Val
            245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Phe Val Pro Ala
            290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
            325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
            355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
            405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
            435                 440                 445

Ser Tyr Thr Pro Gln Leu Gln Asp Leu Asp Pro Leu Ala Gln Glu His
            450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
            485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
            515                 520                 525

Arg Pro Pro Gly Glu Asn Glu Thr Tyr Leu Met Gln Phe Met Glu Glu
            530                 535                 540

Trp Gly Leu Tyr Val Gln Met Glu Asn
545                 550
```

(2) INFORMATION FOR SEQ ID NO:27:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:27:

-continued

| | | | | | | | | | | | | | | | | |
|---|---|---|---|---|---|---|---|---|---|---|---|---|---|---|---|---|
| ATG | CGG | GCT | CCC | GGC | CGC | CCG | GCC | CTG | CGG | CCG | CTG | CCG | CTG | CCG | CCG | 48 |
| Met | Arg | Ala | Pro | Gly | Arg | Pro | Ala | Leu | Arg | Pro | Leu | Pro | Leu | Pro | Pro | |
| 1 | | | | 5 | | | | | 10 | | | | | 15 | | |

| CTG | CTG | CTG | TTG | CTC | CTG | GCG | GCG | CCT | TGG | GGA | CGG | GCA | GTT | CCC | TGT | 96 |
|---|---|---|---|---|---|---|---|---|---|---|---|---|---|---|---|---|
| Leu | Leu | Leu | Leu | Leu | Leu | Ala | Ala | Pro | Trp | Gly | Arg | Ala | Val | Pro | Cys | |
| | | | 20 | | | | | 25 | | | | | 30 | | | |

| GTC | TCT | GGT | GGT | TTG | CCT | AAG | CCT | GCA | AAC | ATC | ACC | TTC | TTA | TCC | ATC | 144 |
|---|---|---|---|---|---|---|---|---|---|---|---|---|---|---|---|---|
| Val | Ser | Gly | Gly | Leu | Pro | Lys | Pro | Ala | Asn | Ile | Thr | Phe | Leu | Ser | Ile | |
| | 35 | | | | | 40 | | | | | 45 | | | | | |

| AAC | ATG | AAG | AAT | GTC | CTA | CAA | TGG | ACT | CCA | CCA | GAG | GGT | CTT | CAA | GGA | 192 |
|---|---|---|---|---|---|---|---|---|---|---|---|---|---|---|---|---|
| Asn | Met | Lys | Asn | Val | Leu | Gln | Trp | Thr | Pro | Pro | Glu | Gly | Leu | Gln | Gly | |
| 50 | | | | | 55 | | | | | 60 | | | | | | |

| GTT | AAG | GTT | ACT | TAC | ACT | GTG | CAG | TAT | TTC | ATC | TAT | GGG | CAA | AAG | AAG | 240 |
|---|---|---|---|---|---|---|---|---|---|---|---|---|---|---|---|---|
| Val | Lys | Val | Thr | Tyr | Thr | Val | Gln | Tyr | Phe | Ile | Tyr | Gly | Gln | Lys | Lys | |
| 65 | | | | 70 | | | | | 75 | | | | | 80 | | |

| TGG | CTG | AAT | AAG | TCA | GAA | TGC | AGA | AAT | ATC | AAT | AGA | ACC | TAC | TGT | GAT | 288 |
|---|---|---|---|---|---|---|---|---|---|---|---|---|---|---|---|---|
| Trp | Leu | Asn | Lys | Ser | Glu | Cys | Arg | Asn | Ile | Asn | Arg | Thr | Tyr | Cys | Asp | |
| | | | | 85 | | | | | 90 | | | | | 95 | | |

| CTT | TCT | GCT | GAA | ACT | TCT | GAC | TAC | GAA | CAC | CAG | TAT | TAT | GCC | AAG | GTT | 336 |
|---|---|---|---|---|---|---|---|---|---|---|---|---|---|---|---|---|
| Leu | Ser | Ala | Glu | Thr | Ser | Asp | Tyr | Glu | His | Gln | Tyr | Tyr | Ala | Lys | Val | |
| | | | 100 | | | | | 105 | | | | | 110 | | | |

| AAG | GCC | ATT | TGG | GGA | ACA | AAG | TGT | TCC | AAG | TGG | GCT | GAA | AGT | GGA | CGG | 384 |
|---|---|---|---|---|---|---|---|---|---|---|---|---|---|---|---|---|
| Lys | Ala | Ile | Trp | Gly | Thr | Lys | Cys | Ser | Lys | Trp | Ala | Glu | Ser | Gly | Arg | |
| | | 115 | | | | | 120 | | | | | 125 | | | | |

| TTC | TAT | CCT | TTT | TTA | GAA | ACA | CAA | ATT | GGC | CCA | CCA | GAG | GTG | GCA | CTG | 432 |
|---|---|---|---|---|---|---|---|---|---|---|---|---|---|---|---|---|
| Phe | Tyr | Pro | Phe | Leu | Glu | Thr | Gln | Ile | Gly | Pro | Pro | Glu | Val | Ala | Leu | |
| | 130 | | | | | 135 | | | | | 140 | | | | | |

| ACT | ACA | GAT | GAG | AAG | TCC | ATT | TCT | GTT | GTC | CTG | ACA | GCT | CCA | GAG | AAG | 480 |
|---|---|---|---|---|---|---|---|---|---|---|---|---|---|---|---|---|
| Thr | Thr | Asp | Glu | Lys | Ser | Ile | Ser | Val | Val | Leu | Thr | Ala | Pro | Glu | Lys | |
| 145 | | | | | 150 | | | | | 155 | | | | | 160 | |

| TGG | AAG | AGA | AAT | CCA | GAA | GAC | CTT | CCT | GTT | TCC | ATG | CAA | CAA | ATC | TAC | 528 |
|---|---|---|---|---|---|---|---|---|---|---|---|---|---|---|---|---|
| Trp | Lys | Arg | Asn | Pro | Glu | Asp | Leu | Pro | Val | Ser | Met | Gln | Gln | Ile | Tyr | |
| | | | | 165 | | | | | 170 | | | | | 175 | | |

| TCC | AAT | CTG | AAG | TAT | AAC | GTG | TCT | GTG | TTG | AAT | ACT | AAG | TCA | AAC | AGA | 576 |
|---|---|---|---|---|---|---|---|---|---|---|---|---|---|---|---|---|
| Ser | Asn | Leu | Lys | Tyr | Asn | Val | Ser | Val | Leu | Asn | Thr | Lys | Ser | Asn | Arg | |
| | | | 180 | | | | | 185 | | | | | 190 | | | |

| ACG | TGG | TCC | CAG | TGT | GTG | ACC | AAC | CAC | ACG | CTG | GTG | CTC | ACC | TGG | CTG | 624 |
|---|---|---|---|---|---|---|---|---|---|---|---|---|---|---|---|---|
| Thr | Trp | Ser | Gln | Cys | Val | Thr | Asn | His | Thr | Leu | Val | Leu | Thr | Trp | Leu | |
| | | 195 | | | | | 200 | | | | | 205 | | | | |

| GAG | CCG | AAC | ACT | CTT | TAC | TGC | GTA | CAC | GTG | GAG | TCC | TTC | GTC | CCA | GGG | 672 |
|---|---|---|---|---|---|---|---|---|---|---|---|---|---|---|---|---|
| Glu | Pro | Asn | Thr | Leu | Tyr | Cys | Val | His | Val | Glu | Ser | Phe | Val | Pro | Gly | |
| | 210 | | | | | 215 | | | | | 220 | | | | | |

| CCC | CCT | CGC | CGT | GCT | CAG | CCT | TCT | GAG | AAG | CAG | TGT | GCC | AGG | ACT | TTG | 720 |
|---|---|---|---|---|---|---|---|---|---|---|---|---|---|---|---|---|
| Pro | Pro | Arg | Arg | Ala | Gln | Pro | Ser | Glu | Lys | Gln | Cys | Ala | Arg | Thr | Leu | |
| 225 | | | | | 230 | | | | | 235 | | | | | 240 | |

| AAG | GAT | CAA | TCA | TCA | GAG | TTC | AAG | GCT | AAG | ATC | ATC | TTC | TGG | TAT | GTT | 768 |
|---|---|---|---|---|---|---|---|---|---|---|---|---|---|---|---|---|
| Lys | Asp | Gln | Ser | Ser | Glu | Phe | Lys | Ala | Lys | Ile | Ile | Phe | Trp | Tyr | Val | |
| | | | | 245 | | | | | 250 | | | | | 255 | | |

| TTG | CCC | ATC | TCT | ATT | ACC | GTG | TTT | CTT | TTT | TCT | GTG | ATG | GGC | TAT | TCC | 816 |
|---|---|---|---|---|---|---|---|---|---|---|---|---|---|---|---|---|
| Leu | Pro | Ile | Ser | Ile | Thr | Val | Phe | Leu | Phe | Ser | Val | Met | Gly | Tyr | Ser | |
| | | | 260 | | | | | 265 | | | | | 270 | | | |

| ATC | TAC | CGA | TAT | ATC | CAC | GTT | GGC | AAG | GAG | AAG | CAC | CCA | GCA | AAT | TTG | 864 |
|---|---|---|---|---|---|---|---|---|---|---|---|---|---|---|---|---|
| Ile | Tyr | Arg | Tyr | Ile | His | Val | Gly | Lys | Glu | Lys | His | Pro | Ala | Asn | Leu | |
| | | 275 | | | | | 280 | | | | | 285 | | | | |

| ATT | TTG | ATT | TAT | GGA | AAT | GAA | TTT | GAC | AAG | AGA | TTC | TTT | GTG | CCT | GCT | 912 |
|---|---|---|---|---|---|---|---|---|---|---|---|---|---|---|---|---|
| Ile | Leu | Ile | Tyr | Gly | Asn | Glu | Phe | Asp | Lys | Arg | Phe | Phe | Val | Pro | Ala | |
| | 290 | | | | | 295 | | | | | 300 | | | | | |

| GAA | AAG | ATC | GTG | ATT | AAC | TTT | ATC | ACC | CTC | AAT | ATC | TCG | GAT | GAT | TCT | 960 |
|---|---|---|---|---|---|---|---|---|---|---|---|---|---|---|---|---|
| Glu | Lys | Ile | Val | Ile | Asn | Phe | Ile | Thr | Leu | Asn | Ile | Ser | Asp | Asp | Ser | |
| 305 | | | | | 310 | | | | | 315 | | | | | 320 | |

```
AAG ATT TCT CAT CAG GAT ATG AGT TTA CTG GGA AAG AGC AGT GAT GTA    1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG    1056
Ser Ser Leu Asn Asp Pro Gln Pro Ser Gly Asn Leu Arg Pro Pro Gln
            340                 345                 350

GAG GAA GAG GAG GTG AAG CAT TTA GGG TAT GCT TCG CAT TTG ATG GAA    1104
Glu Glu Glu Glu Val Lys His Leu Gly Tyr Ala Ser His Leu Met Glu
            355                 360                 365

ATT TTT TGT GAC TCT GAA GAA AAC ACG GAA GGT ACT TCT TTC ACC CAG    1152
Ile Phe Cys Asp Ser Glu Glu Asn Thr Glu Gly Thr Ser Phe Thr Gln
370                 375                 380

CAA GAG TCC CTC AGC AGA ACA ATC CCC CCG GAT AAG ACA GTC ATT GAA    1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG    1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTA TTG    1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC    1344
Glu Ser Gln Ala Ala Leu Ala Val Leu Gly Pro Gln Thr Leu Gln Tyr
            435                 440                 445

TCA TAC ACC CCT CAG CTC CAA GAC TTA GAC CCC CTG GCG CAG GAG CAC    1392
Ser Tyr Thr Pro Gln Leu Gln Asp Leu Asp Pro Leu Ala Gln Glu His
            450                 455                 460

ACA GAC TCG GAG GAG GGG CCG GAG GAA GAG CCA TCG ACG ACC CTG GTC    1440
Thr Asp Ser Glu Glu Gly Pro Glu Glu Glu Pro Ser Thr Thr Leu Val
465                 470                 475                 480

GAC TGG GAT CCC CAA ACT GGC AGG CTG TGT ATT CCT TCG CTG TCC AGC    1488
Asp Trp Asp Pro Gln Thr Gly Arg Leu Cys Ile Pro Ser Leu Ser Ser
            485                 490                 495

TTC GAC CAG GAT TCA GAG GGC TGC GAG CCT TCT GAG GGG GAT GGG CTC    1536
Phe Asp Gln Asp Ser Glu Gly Cys Glu Pro Ser Glu Gly Asp Gly Leu
            500                 505                 510

GGA GAG GAG GGT CTT CTA TCT AGA CTC TAT GAG GAG CCG GCT CCA GAC    1584
Gly Glu Glu Gly Leu Leu Ser Arg Leu Tyr Glu Glu Pro Ala Pro Asp
            515                 520                 525

AGG CCA CCA GGA GAA AAT GAA ACC TAT CTC ATG CAA TTC ATG GAG GAA    1632
Arg Pro Pro Gly Glu Asn Glu Thr Tyr Leu Met Gln Phe Met Glu Glu
530                 535                 540

TGG GGG TTA TAT GTG CAG ATG GAA AAC                                1659
Trp Gly Leu Tyr Val Gln Met Glu Asn
545                 550

(2) INFORMATION FOR SEQ ID NO:28:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:28:

Met Arg Ala Pro Gly Arg Pro Ala Leu Arg Pro Leu Pro Pro
1               5                   10                  15

Leu Leu Leu Leu Leu Leu Ala Ala Pro Trp Gly Arg Ala Val Pro Cys
            20                  25                  30
```

-continued

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
 50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
        130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
                180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
                260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Phe Val Pro Ala
        290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
            355                 360                 365

Ile Phe Cys Asp Ser Glu Glu Asn Thr Glu Gly Thr Ser Phe Thr Gln
        370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
                420                 425                 430

Glu Ser Gln Ala Ala Leu Ala Val Leu Gly Pro Gln Thr Leu Gln Tyr
            435                 440                 445
```

```
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                    485                 490                 495
Phe Asp Gln Asp Ser Glu Gly Cys Glu Pro Ser Glu Gly Asp Gly Leu
                500                 505                 510
Gly Glu Glu Gly Leu Leu Ser Arg Leu Tyr Glu Glu Pro Ala Pro Asp
            515                 520                 525
Arg Pro Pro Gly Glu Asn Glu Thr Tyr Leu Met Gln Phe Met Glu Glu
    530                 535                 540
Trp Gly Leu Tyr Val Gln Met Glu Asn
545                 550
```

(2) INFORMATION FOR SEQ ID NO:29:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:29:

```
ATG CGG GCT CCC GGC CGC CCG GCC CTG CGG CCG CTG CCG CTG CCG CCG      48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGA CGG GCA GTT CCC TGT      96
Leu Leu Leu Leu Leu Leu Ala Ala Pro Trp Gly Arg Ala Val Pro Cys
             20                  25                  30

GTC TCT GGT GGT TTG CCT AAG CCT GCA AAC ATC ACC TTC TTG TCC ATC     144
Val Ser Gly Gly Leu Pro Lys Pro Ala Asn Ile Thr Phe Leu Ser Ile
         35                  40                  45

AAC ATG AAG AAT GTC CTA CAA TGG ACT CCA CCA GAG GGT CTT CAA GGA     192
Asn Met Lys Asn Val Leu Gln Trp Thr Pro Pro Glu Gly Leu Gln Gly
     50                  55                  60

GTT AAG GTT ACT TAC ACT GTG CAG TAT TTC ATA TAT GGG CAA AAG AAG     240
Val Lys Val Thr Tyr Thr Val Gln Tyr Phe Ile Tyr Gly Gln Lys Lys
 65                  70                  75                  80

TGG CTG AAT AAG TCA GAA TGC AGA AAT ATC AAT AGA ACC TAC TGT GAT     288
Trp Leu Asn Lys Ser Glu Cys Arg Asn Ile Asn Arg Thr Tyr Cys Asp
                 85                  90                  95

CTT TCT GCT GAA ACT TCT GAC TAC GAA CAC CAG TAT TAT GCC AAG GTT     336
Leu Ser Ala Glu Thr Ser Asp Tyr Glu His Gln Tyr Tyr Ala Lys Val
            100                 105                 110

AAG GCC ATT TGG GGA ACA AAG TGT TCC AAG TGG GCT GAA AGT GGA CGG     384
Lys Ala Ile Trp Gly Thr Lys Cys Ser Lys Trp Ala Glu Ser Gly Arg
        115                 120                 125

TTC TAT CCT TTT TTG GAA ACA CAA ATT GGC CCA CCA GAG GTG GCA CTG     432
Phe Tyr Pro Phe Leu Glu Thr Gln Ile Gly Pro Pro Glu Val Ala Leu
    130                 135                 140

ACT ACA GAT GAG AAG TCC ATT TCT GTT GTC CTG ACA GCT CCA GAG AAG     480
Thr Thr Asp Glu Lys Ser Ile Ser Val Val Leu Thr Ala Pro Glu Lys
145                 150                 155                 160
```

```
TGG AAG AGA AAT CCA GAA GAC CTT CCT GTT TCC ATG CAA CAA ATA TAC      528
Trp Lys Arg Asn Pro Glu Asp Leu Pro Val Ser Met Gln Gln Ile Tyr
            165                 170                 175

TCC AAT CTG AAG TAT AAC GTG TCT GTG TTG AAT ACT AAG TCA AAC AGA      576
Ser Asn Leu Lys Tyr Asn Val Ser Val Leu Asn Thr Lys Ser Asn Arg
            180                 185                 190

ACG TGG TCC CAG TGT GTG ACC AAC CAC ACG CTG GTG CTC ACC TGG CTG      624
Thr Trp Ser Gln Cys Val Thr Asn His Thr Leu Val Leu Thr Trp Leu
            195                 200                 205

GAG CCG AAC ACT CTT TAC TGC GTA CAC GTG GAG TCC TTC GTC CCA GGG      672
Glu Pro Asn Thr Leu Tyr Cys Val His Val Glu Ser Phe Val Pro Gly
        210                 215                 220

CCC CCT CGC CGT GCT CAG CCT TCT GAG AAG CAG TGT GCC AGG ACT TTG      720
Pro Pro Arg Arg Ala Gln Pro Ser Glu Lys Gln Cys Ala Arg Thr Leu
225                 230                 235                 240

AAG GAT CAA TCA TCA GAG TTC AAG GCT AAG ATC ATC TTC TGG TAT GTT      768
Lys Asp Gln Ser Ser Glu Phe Lys Ala Lys Ile Ile Phe Trp Tyr Val
                245                 250                 255

TTG CCC ATA TCT ATT ACC GTG TTT CTT TTT TCT GTG ATG GGC TAT TCC      816
Leu Pro Ile Ser Ile Thr Val Phe Leu Phe Ser Val Met Gly Tyr Ser
                260                 265                 270

ATC TAC CGA TAT ATC CAC GTT GGC AAG GAG AAG CAC CCA GCA AAT TTG      864
Ile Tyr Arg Tyr Ile His Val Gly Lys Glu Lys His Pro Ala Asn Leu
            275                 280                 285

ATT TTG ATT TAT GGA AAT GAA TTT GAC AAG AGA TTC TTT GTG CCT GCT      912
Ile Leu Ile Tyr Gly Asn Glu Phe Asp Lys Arg Phe Phe Val Pro Ala
        290                 295                 300

GAA AAG ATC GTG ATT AAC TTT ATC ACC CTC AAT ATC TCG GAT GAT TCT      960
Glu Lys Ile Val Ile Asn Phe Ile Thr Leu Asn Ile Ser Asp Asp Ser
305                 310                 315                 320

AAG ATT TCT CAT CAG GAT ATG AGT TTG CTG GGA AAG AGC AGT GAT GTA     1008
Lys Ile Ser His Gln Asp Met Ser Leu Leu Gly Lys Ser Ser Asp Val
                325                 330                 335

TCC AGC CTT AAT GAT CCT CAG CCC AGC GGG AAC CTG AGG CCC CCT CAG     1056
Ser Ser Leu Asn Asp Pro Gln Pro Ser Gly Asn Leu Arg Pro Pro Gln
                340                 345                 350

GAG GAA GAG GAG GTG AAG CAT TTG GGG TAT GCT TCA CAT TTG ATG GAA     1104
Glu Glu Glu Glu Val Lys His Leu Gly Tyr Ala Ser His Leu Met Glu
            355                 360                 365

ATT TTT TGT GAC TCT GAA GAA AAC ACG GAA GGT ACT TCT TTC ACC CAG     1152
Ile Phe Cys Asp Ser Glu Glu Asn Thr Glu Gly Thr Ser Phe Thr Gln
        370                 375                 380

CAA GAG TCC CTC AGC AGA ACA ATA CCC CCG GAT AAG ACA GTC ATT GAA     1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG     1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTG TTG     1296
Gln Glu Leu Ser Leu Gln Glu Glu Val Ser Thr Gln Gly Thr Leu Leu
                420                 425                 430

GAG TCG CAG GCA GCG TTG GCA GTC TTG GGC CCG CAA ACG TTG CAG TAC     1344
Glu Ser Gln Ala Ala Leu Ala Val Leu Gly Pro Gln Thr Leu Gln Tyr
            435                 440                 445

TCA TAC ACC CCT CAG CTC CAA GAC TTG GAC CCC CTG GCG CAG GAG CAC     1392
Ser Tyr Thr Pro Gln Leu Gln Asp Leu Asp Pro Leu Ala Gln Glu His
        450                 455                 460

ACA GAC TCG GAG GAG GGG CCG GAG GAA GAG CCA TCG ACG ACC CTG GTC     1440
Thr Asp Ser Glu Glu Gly Pro Glu Glu Glu Pro Ser Thr Thr Leu Val
465                 470                 475                 480
```

```
GAC TGG GAT CCC CAA ACT GGC AGG CTG TGT ATT CCT TCG CTG TCC AGC      1488
Asp Trp Asp Pro Gln Thr Gly Arg Leu Cys Ile Pro Ser Leu Ser Ser
                485                 490                 495

TTC GAC CAG GAT TCA GAG GGC TGC GAG CCT TCT GAG GGG GAT GGG CTC      1536
Phe Asp Gln Asp Ser Glu Gly Cys Glu Pro Ser Glu Gly Asp Gly Leu
                500                 505                 510

GGA GAG GAG GGT CTT CTA TCT AGA CTC TAT GAG GAG CCG GCT CCA GAC      1584
Gly Glu Glu Gly Leu Leu Ser Arg Leu Tyr Glu Glu Pro Ala Pro Asp
                515                 520                 525

AGG CCA CCA GGA GAA AAT GAA ACC TAT CTC ATG CAA TTC ATG GAG GAA      1632
Arg Pro Pro Gly Glu Asn Glu Thr Tyr Leu Met Gln Phe Met Glu Glu
        530                 535                 540

TGG GGG TTG TAT GTG CAG ATG GAA AAC                                  1659
Trp Gly Leu Tyr Val Gln Met Glu Asn
545                 550

(2) INFORMATION FOR SEQ ID NO:30:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:30:

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
                20                  25                  30

Val Ser Gly Gly Leu Pro Lys Pro Ala Asn Ile Thr Phe Leu Ser Ile
                35                  40                  45

Asn Met Lys Asn Val Leu Gln Trp Thr Pro Glu Gly Leu Gln Gly
            50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
                115                 120                 125

Phe Tyr Pro Phe Leu Glu Thr Gln Ile Gly Pro Pro Glu Val Ala Leu
                130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
                180                 185                 190

Thr Trp Ser Gln Cys Val Thr Asn His Thr Leu Val Leu Thr Trp Leu
                195                 200                 205

Glu Pro Asn Thr Leu Tyr Cys Val His Val Glu Ser Phe Val Pro Gly
                210                 215                 220

Pro Pro Arg Arg Ala Gln Pro Ser Glu Lys Gln Cys Ala Arg Thr Leu
225                 230                 235                 240
```

```
Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
    290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Val Ser Thr Gln Gly Thr Leu Leu
                420                 425                 430

Glu Ser Gln Ala Ala Leu Ala Val Leu Gly Pro Gln Thr Leu Gln Tyr
                435                 440                 445

Ser Tyr Thr Pro Gln Leu Gln Asp Leu Asp Pro Leu Ala Gln Glu His
450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Glu Pro Ala Pro Asp
                515                 520                 525

Arg Pro Pro Gly Glu Asn Glu Thr Tyr Leu Met Gln Phe Met Glu Glu
                530                 535                 540

Trp Gly Leu Tyr Val Gln Met Glu Asn
545                 550
```

(2) INFORMATION FOR SEQ ID NO:31:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:31:

| | |
|---|---|
| ATG CGG GCT CCC GGC CGC CCG GCC CTG CGG CCG CTG CCG CTG CCG CCG<br>Met Arg Ala Pro Gly Arg Pro Ala Leu Arg Pro Leu Pro Leu Pro Pro<br>1               5                   10                  15 | 48 |
| CTG CTG CTG TTG CTC CTG GCG GCG CCT TGG GGA CGG GCA GTT CCC TGT<br>Leu Leu Leu Leu Leu Leu Ala Ala Pro Trp Gly Arg Ala Val Pro Cys<br>        20                  25                  30 | 96 |
| GTC TCT GGT GGT TTG CCT AAA CCT GCA AAT ATC ACC TTC TTG TCC ATC<br>Val Ser Gly Gly Leu Pro Lys Pro Ala Asn Ile Thr Phe Leu Ser Ile<br>            35                  40                  45 | 144 |
| AAT ATG AAG AAT GTC CTA CAA TGG ACT CCA CCA GAG GGT CTT CAA GGA<br>Asn Met Lys Asn Val Leu Gln Trp Thr Pro Pro Glu Gly Leu Gln Gly<br>    50                  55                  60 | 192 |
| GTT AAA GTT ACT TAC ACT GTG CAG TAT TTC ATA TAT GGG CAA AAG AAA<br>Val Lys Val Thr Tyr Thr Val Gln Tyr Phe Ile Tyr Gly Gln Lys Lys<br>65                  70                  75                  80 | 240 |
| TGG CTG AAT AAA TCA GAA TGC AGA AAT ATC AAT AGA ACC TAC TGT GAT<br>Trp Leu Asn Lys Ser Glu Cys Arg Asn Ile Asn Arg Thr Tyr Cys Asp<br>                85                  90                  95 | 288 |
| CTT TCT GCT GAA ACT TCT GAC TAC GAA CAC CAG TAT TAT GCC AAA GTT<br>Leu Ser Ala Glu Thr Ser Asp Tyr Glu His Gln Tyr Tyr Ala Lys Val<br>            100                 105                 110 | 336 |
| AAG GCC ATT TGG GGA ACA AAG TGT TCC AAA TGG GCT GAA AGT GGA CGG<br>Lys Ala Ile Trp Gly Thr Lys Cys Ser Lys Trp Ala Glu Ser Gly Arg<br>        115                 120                 125 | 384 |
| TTC TAT CCT TTT TTG GAA ACA CAA ATT GGC CCA CCA GAG GTG GCA CTG<br>Phe Tyr Pro Phe Leu Glu Thr Gln Ile Gly Pro Pro Glu Val Ala Leu<br>    130                 135                 140 | 432 |
| ACT ACA GAT GAG AAG TCC ATT TCT GTT GTC CTG ACA GCT CCA GAG AAG<br>Thr Thr Asp Glu Lys Ser Ile Ser Val Val Leu Thr Ala Pro Glu Lys<br>145                 150                 155                 160 | 480 |
| TGG AAG AGA AAT CCA GAA GAC CTT CCT GTT TCC ATG CAA CAA ATA TAC<br>Trp Lys Arg Asn Pro Glu Asp Leu Pro Val Ser Met Gln Gln Ile Tyr<br>                165                 170                 175 | 528 |
| TCC AAT CTG AAG TAT AAT GTG TCT GTG TTG AAT ACT AAA TCA AAT AGA<br>Ser Asn Leu Lys Tyr Asn Val Ser Val Leu Asn Thr Lys Ser Asn Arg<br>            180                 185                 190 | 576 |
| ACG TGG TCC CAG TGT GTG ACC AAT CAC ACG CTG GTG CTC ACC TGG CTG<br>Thr Trp Ser Gln Cys Val Thr Asn His Thr Leu Val Leu Thr Trp Leu<br>        195                 200                 205 | 624 |
| GAG CCG AAT ACT CTT TAC TGC GTA CAC GTG GAG TCC TTC GTC CCA GGG<br>Glu Pro Asn Thr Leu Tyr Cys Val His Val Glu Ser Phe Val Pro Gly<br>    210                 215                 220 | 672 |
| CCC CCT CGC CGT GCT CAG CCT TCT GAG AAG CAG TGT GCC AGG ACT TTG<br>Pro Pro Arg Arg Ala Gln Pro Ser Glu Lys Gln Cys Ala Arg Thr Leu<br>225                 230                 235                 240 | 720 |
| AAA GAT CAA TCA TCA GAG TTC AAG GCT AAA ATC ATC TTC TGG TAT GTT<br>Lys Asp Gln Ser Ser Glu Phe Lys Ala Lys Ile Ile Phe Trp Tyr Val<br>                245                 250                 255 | 768 |
| TTG CCC ATA TCT ATT ACC GTG TTT CTT TTT TCT GTG ATG GGC TAT TCC<br>Leu Pro Ile Ser Ile Thr Val Phe Leu Phe Ser Val Met Gly Tyr Ser<br>            260                 265                 270 | 816 |
| ATC TAC CGA TAT ATC CAC GTT GGC AAA GAG AAA CAC CCA GCA AAT TTG<br>Ile Tyr Arg Tyr Ile His Val Gly Lys Glu Lys His Pro Ala Asn Leu<br>        275                 280                 285 | 864 |
| ATT TTG ATT TAT GGA AAT GAA TTT GAC AAA AGA TTC TTT GTG CCT GCT<br>Ile Leu Ile Tyr Gly Asn Glu Phe Asp Lys Arg Phe Phe Val Pro Ala<br>    290                 295                 300 | 912 |
| GAA AAA ATC GTG ATT AAT TTT ATC ACC CTC AAT ATC TCG GAT GAT TCT<br>Glu Lys Ile Val Ile Asn Phe Ile Thr Leu Asn Ile Ser Asp Asp Ser<br>305                 310                 315                 320 | 960 |

| | |
|---|---|
| AAA ATT TCT CAT CAG GAT ATG AGT TTG CTG GGA AAA AGC AGT GAT GTA<br>Lys Ile Ser His Gln Asp Met Ser Leu Leu Gly Lys Ser Ser Asp Val<br>325 330 335 | 1008 |
| TCC AGC CTT AAT GAT CCT CAG CCC AGC GGG AAT CTG AGG CCC CCT CAG<br>Ser Ser Leu Asn Asp Pro Gln Pro Ser Gly Asn Leu Arg Pro Pro Gln<br>340 345 350 | 1056 |
| GAG GAA GAG GAG GTG AAA CAT TTG GGG TAT GCT TCG CAT TTG ATG GAA<br>Glu Glu Glu Glu Val Lys His Leu Gly Tyr Ala Ser His Leu Met Glu<br>355 360 365 | 1104 |
| ATT TTT TGT GAC TCT GAA GAA AAT ACG GAA GGT ACT TCT TTC ACC CAG<br>Ile Phe Cys Asp Ser Glu Glu Asn Thr Glu Gly Thr Ser Phe Thr Gln<br>370 375 380 | 1152 |
| CAA GAG TCC CTC AGC AGA ACA ATA CCC CCG GAT AAA ACA GTC ATT GAA<br>Gln Glu Ser Leu Ser Arg Thr Ile Pro Pro Asp Lys Thr Val Ile Glu<br>385 390 395 400 | 1200 |
| TAT GAA TAT GAT GTC AGA ACC ACT GAC ATT TGT GCG GGG CCT GAA GAG<br>Tyr Glu Tyr Asp Val Arg Thr Thr Asp Ile Cys Ala Gly Pro Glu Glu<br>405 410 415 | 1248 |
| CAG GAG CTC AGT TTG CAG GAG GAG GTG TCC ACA CAA GGA ACA TTG TTG<br>Gln Glu Leu Ser Leu Gln Glu Glu Val Ser Thr Gln Gly Thr Leu Leu<br>420 425 430 | 1296 |
| GAG TCG CAG GCA GCG TTG GCA GTC TTG GGC CCG CAA ACG TTG CAG TAC<br>Glu Ser Gln Ala Ala Leu Ala Val Leu Gly Pro Gln Thr Leu Gln Tyr<br>435 440 445 | 1344 |
| TCA TAC ACC CCT CAG CTC CAA GAC TTG GAC CCC CTG GCG CAG GAG CAC<br>Ser Tyr Thr Pro Gln Leu Gln Asp Leu Asp Pro Leu Ala Gln Glu His<br>450 455 460 | 1392 |
| ACA GAC TCG GAG GAG GGG CCG GAG GAA GAG CCA TCG ACG ACC CTG GTC<br>Thr Asp Ser Glu Glu Gly Pro Glu Glu Glu Pro Ser Thr Thr Leu Val<br>465 470 475 480 | 1440 |
| GAC TGG GAT CCC CAA ACT GGC AGG CTG TGT ATT CCT TCG CTG TCC AGC<br>Asp Trp Asp Pro Gln Thr Gly Arg Leu Cys Ile Pro Ser Leu Ser Ser<br>485 490 495 | 1488 |
| TTC GAC CAG GAT TCA GAG GGC TGC GAG CCT TCT GAG GGG GAT GGG CTC<br>Phe Asp Gln Asp Ser Glu Gly Cys Glu Pro Ser Glu Gly Asp Gly Leu<br>500 505 510 | 1536 |
| GGA GAG GAG GGT CTT CTA TCT AGA CTC TAT GAG GAG CCG GCT CCA GAC<br>Gly Glu Glu Gly Leu Leu Ser Arg Leu Tyr Glu Glu Pro Ala Pro Asp<br>515 520 525 | 1584 |
| AGG CCA CCA GGA GAA AAT GAA ACC TAT CTC ATG CAA TTC ATG GAG GAA<br>Arg Pro Pro Gly Glu Asn Glu Thr Tyr Leu Met Gln Phe Met Glu Glu<br>530 535 540 | 1632 |
| TGG GGG TTA TAT GTG CAG ATG GAA AAT<br>Trp Gly Leu Tyr Val Gln Met Glu Asn<br>545 550 | 1659 |

(2) INFORMATION FOR SEQ ID NO:32:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:32:

Met Arg Ala Pro Gly Arg Pro Ala Leu Arg Pro Leu Pro Leu Pro Pro
1 5 10 15

Leu Leu Leu Leu Leu Leu Ala Ala Pro Trp Gly Arg Ala Val Pro Cys
20 25 30

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
 65              70                  75                      80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
                180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
        290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
            355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
            435                 440                 445
```

```
Ser Tyr Thr Pro Gln Leu Gln Asp Leu Asp Pro Leu Ala Gln Glu His
    450                 455                 460
Thr Asp Ser Glu Glu Gly Pro Glu Glu Glu Pro Ser Thr Thr Leu Val
465                 470                 475                 480
Asp Trp Asp Pro Gln Thr Gly Arg Leu Cys Ile Pro Ser Leu Ser Ser
                    485                 490                 495
Phe Asp Gln Asp Ser Glu Gly Cys Glu Pro Ser Glu Gly Asp Gly Leu
                500                 505                 510
Gly Glu Glu Gly Leu Leu Ser Arg Leu Tyr Glu Glu Pro Ala Pro Asp
                515                 520                 525
Arg Pro Pro Gly Glu Asn Glu Thr Tyr Leu Met Gln Phe Met Glu Glu
                530                 535                 540
Trp Gly Leu Tyr Val Gln Met Glu Asn
545                 550
```

(2) INFORMATION FOR SEQ ID NO:33:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:33:

```
ATG CGG GCT CCC GGC CGC CCG GCC CTG CGG CCG CTG CCG CTG CCG CCG    48
Met Arg Ala Pro Gly Arg Pro Ala Leu Arg Pro Leu Pro Leu Pro Pro
1               5                   10                  15

CTG CTG CTG TTG CTC CTG GCG GCG CCT TGG GGA CGG GCA GTT CCC TGT    96
Leu Leu Leu Leu Leu Leu Ala Ala Pro Trp Gly Arg Ala Val Pro Cys
            20                  25                  30

GTC TCT GGT GGT TTG CCT AAA CCT GCA AAT ATC ACC TTC TTA TCC ATC   144
Val Ser Gly Gly Leu Pro Lys Pro Ala Asn Ile Thr Phe Leu Ser Ile
        35                  40                  45

AAT ATG AAG AAT GTC CTA CAA TGG ACT CCC CCC GAG GGT CTT CAA GGA   192
Asn Met Lys Asn Val Leu Gln Trp Thr Pro Pro Glu Gly Leu Gln Gly
50                  55                  60

GTT AAA GTT ACT TAC ACT GTG CAG TAT TTC ATA TAT GGG CAA AAG AAA   240
Val Lys Val Thr Tyr Thr Val Gln Tyr Phe Ile Tyr Gly Gln Lys Lys
65                  70                  75                  80

TGG CTG AAT AAA TCA GAA TGC AGA AAT ATC AAT AGA ACC TAC TGT GAT   288
Trp Leu Asn Lys Ser Glu Cys Arg Asn Ile Asn Arg Thr Tyr Cys Asp
                85                  90                  95

CTT TCT GCT GAA ACT TCT GAC TAC GAA CAC CAG TAT TAT GCC AAA GTT   336
Leu Ser Ala Glu Thr Ser Asp Tyr Glu His Gln Tyr Tyr Ala Lys Val
            100                 105                 110

AAG GCC ATT TGG GGA ACA AAG TGT TCC AAA TGG GCT GAA AGT GGA CGG   384
Lys Ala Ile Trp Gly Thr Lys Cys Ser Lys Trp Ala Glu Ser Gly Arg
        115                 120                 125

TTC TAT CCT TTT TTA GAA ACA CAA ATT GGC CCC CCC GAG GTG GCA CTG   432
Phe Tyr Pro Phe Leu Glu Thr Gln Ile Gly Pro Pro Glu Val Ala Leu
130                 135                 140

ACT ACA GAT GAG AAG TCC ATT TCT GTT GTC CTG ACA GCT CCC GAG AAG   480
Thr Thr Asp Glu Lys Ser Ile Ser Val Val Leu Thr Ala Pro Glu Lys
145                 150                 155                 160
```

```
TGG AAG AGA AAT CCC GAA GAC CTT CCT GTT TCC ATG CAA CAA ATA TAC      528
Trp Lys Arg Asn Pro Glu Asp Leu Pro Val Ser Met Gln Gln Ile Tyr
            165                 170                 175

TCC AAT CTG AAG TAT AAT GTG TCT GTG TTG AAT ACT AAA TCA AAT AGA      576
Ser Asn Leu Lys Tyr Asn Val Ser Val Leu Asn Thr Lys Ser Asn Arg
        180                 185                 190

ACG TGG TCC CAG TGT GTG ACC AAT CAC ACG CTG GTG CTC ACC TGG CTG      624
Thr Trp Ser Gln Cys Val Thr Asn His Thr Leu Val Leu Thr Trp Leu
        195                 200                 205

GAG CCG AAT ACT CTT TAC TGC GTA CAC GTG GAG TCC TTC GTC CCC GGG      672
Glu Pro Asn Thr Leu Tyr Cys Val His Val Glu Ser Phe Val Pro Gly
    210                 215                 220

CCC CCT CGC CGT GCT CAG CCT TCT GAG AAG CAG TGT GCC AGG ACT TTG      720
Pro Pro Arg Arg Ala Gln Pro Ser Glu Lys Gln Cys Ala Arg Thr Leu
225                 230                 235                 240

AAA GAT CAA TCA TCA GAG TTC AAG GCT AAA ATC ATC TTC TGG TAT GTT      768
Lys Asp Gln Ser Ser Glu Phe Lys Ala Lys Ile Ile Phe Trp Tyr Val
                245                 250                 255

TTG CCC ATA TCT ATT ACC GTG TTT CTT TTT TCT GTG ATG GGC TAT TCC      816
Leu Pro Ile Ser Ile Thr Val Phe Leu Phe Ser Val Met Gly Tyr Ser
            260                 265                 270

ATC TAC CGA TAT ATC CAC GTT GGC AAA GAG AAA CAC CCC GCA AAT TTG      864
Ile Tyr Arg Tyr Ile His Val Gly Lys Glu Lys His Pro Ala Asn Leu
        275                 280                 285

ATT TTG ATT TAT GGA AAT GAA TTT GAC AAA AGA TTC TTT GTG CCT GCT      912
Ile Leu Ile Tyr Gly Asn Glu Phe Asp Lys Arg Phe Phe Val Pro Ala
        290                 295                 300

GAA AAA TCG TGA TT AAT TTT ATC ACC CTC AAT ATC TCG GAT GAT TCT      960
Glu Lys Ile Val Ile Asn Phe Ile Thr Leu Asn Ile Ser Asp Asp Ser
305                 310                 315                 320

AAA ATT TCT CAT CAG GAT ATG AGT TTA CTG GGA AAA AGC AGT GAT GTA     1008
Lys Ile Ser His Gln Asp Met Ser Leu Leu Gly Lys Ser Ser Asp Val
                325                 330                 335

TCC AGC CTT AAT GAT CCT CAG CCC AGC GGG AAT CTG AGG CCC CCT CAG     1056
Ser Ser Leu Asn Asp Pro Gln Pro Ser Gly Asn Leu Arg Pro Pro Gln
            340                 345                 350

GAG GAA GAG GAG GTG AAA CAT TTA GGG TAT GCT TCG CAT TTG ATG GAA     1104
Glu Glu Glu Glu Val Lys His Leu Gly Tyr Ala Ser His Leu Met Glu
        355                 360                 365

ATT TTT TGT GAC TCT GAA GAA AAT ACG GAA GGT ACT TCT TTC ACC CAG     1152
Ile Phe Cys Asp Ser Glu Glu Asn Thr Glu Gly Thr Ser Phe Thr Gln
        370                 375                 380

CAA GAG TCC CTC AGC AGA ACA ATA CCC CCG GAT AAA ACA GTC ATT GAA     1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG     1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTA TTG     1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC     1344
Glu Ser Gln Ala Ala Leu Ala Val Leu Gly Pro Gln Thr Leu Gln Tyr
        435                 440                 445

TCA TAC ACC CCT CAG CTC CAA GAC TTA GAC CCC CTG GCG CAG GAG CAC     1392
Ser Tyr Thr Pro Gln Leu Gln Asp Leu Asp Pro Leu Ala Gln Glu His
        450                 455                 460

ACA GAC TCG GAG GAG GGG CCG GAG GAA GAG CCC TCG ACG ACC CTG GTC     1440
Thr Asp Ser Glu Glu Gly Pro Glu Glu Glu Pro Ser Thr Thr Leu Val
465                 470                 475                 480
```

```
GAC TGG GAT CCC CAA ACT GGC AGG CTG TGT ATT CCT TCG CTG TCC AGC      1488
Asp Trp Asp Pro Gln Thr Gly Arg Leu Cys Ile Pro Ser Leu Ser Ser
            485                 490                 495

TTC GAC CAG GAT TCA GAG GGC TGC GAG CCT TCT GAG GGG GAT GGG CTC      1536
Phe Asp Gln Asp Ser Glu Gly Cys Glu Pro Ser Glu Gly Asp Gly Leu
            500                 505                 510

GGA GAG GAG GGT CTT CTA TCT AGA CTC TAT GAG GAG CCG GCT CCC GAC      1584
Gly Glu Glu Gly Leu Leu Ser Arg Leu Tyr Glu Glu Pro Ala Pro Asp
            515                 520                 525

AGG CCC CCC GGA GAA AAT GAA ACC TAT CTC ATG CAA TTC ATG GAG GAA      1632
Arg Pro Pro Gly Glu Asn Glu Thr Tyr Leu Met Gln Phe Met Glu Glu
    530                 535                 540

TGG GGG TTA TAT GTG CAG ATG GAA AAC                                  1659
Trp Gly Leu Tyr Val Gln Met Glu Asn
545                 550
```

(2) INFORMATION FOR SEQ ID NO:34:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:34:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
            50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
210                 215                 220

Pro Pro Arg Arg Ala Gln Pro Ser Glu Lys Gln Cys Ala Arg Thr Leu
225                 230                 235                 240
```

| Lys | Asp | Gln | Ser | Ser | Glu | Phe | Lys | Ala | Lys | Ile | Ile | Phe | Trp | Tyr | Val |
| | | | 245 | | | | | 250 | | | | | 255 | | |

| Leu | Pro | Ile | Ser | Ile | Thr | Val | Phe | Leu | Phe | Ser | Val | Met | Gly | Tyr | Ser |
| | | | 260 | | | | | 265 | | | | | 270 | | |

| Ile | Tyr | Arg | Tyr | Ile | His | Val | Gly | Lys | Glu | Lys | His | Pro | Ala | Asn | Leu |
| | | | 275 | | | | | 280 | | | | | 285 | | |

| Ile | Leu | Ile | Tyr | Gly | Asn | Glu | Phe | Asp | Lys | Arg | Phe | Phe | Val | Pro | Ala |
| | | | 290 | | | | | 295 | | | | | 300 | | |

| Glu | Lys | Ile | Val | Ile | Asn | Phe | Ile | Thr | Leu | Asn | Ile | Ser | Asp | Asp | Ser |
| 305 | | | | | 310 | | | | | 315 | | | | | 320 |

| Lys | Ile | Ser | His | Gln | Asp | Met | Ser | Leu | Leu | Gly | Lys | Ser | Ser | Asp | Val |
| | | | | 325 | | | | | 330 | | | | | 335 | |

| Ser | Ser | Leu | Asn | Asp | Pro | Gln | Pro | Ser | Gly | Asn | Leu | Arg | Pro | Pro | Gln |
| | | | | 340 | | | | | 345 | | | | | 350 | |

| Glu | Glu | Glu | Glu | Val | Lys | His | Leu | Gly | Tyr | Ala | Ser | His | Leu | Met | Glu |
| | | | | 355 | | | | | 360 | | | | | 365 | |

| Ile | Phe | Cys | Asp | Ser | Glu | Glu | Asn | Thr | Glu | Gly | Thr | Ser | Phe | Thr | Gln |
| | | | 370 | | | | | 375 | | | | | 380 | | |

| Gln | Glu | Ser | Leu | Ser | Arg | Thr | Ile | Pro | Pro | Asp | Lys | Thr | Val | Ile | Glu |
| 385 | | | | | 390 | | | | | 395 | | | | | 400 |

| Tyr | Glu | Tyr | Asp | Val | Arg | Thr | Thr | Asp | Ile | Cys | Ala | Gly | Pro | Glu | Glu |
| | | | | 405 | | | | | 410 | | | | | 415 | |

| Gln | Glu | Leu | Ser | Leu | Gln | Glu | Glu | Val | Ser | Thr | Gln | Gly | Thr | Leu | Leu |
| | | | | 420 | | | | | 425 | | | | | 430 | |

| Glu | Ser | Gln | Ala | Ala | Leu | Ala | Val | Leu | Gly | Pro | Gln | Thr | Leu | Gln | Tyr |
| | | | 435 | | | | | 440 | | | | | 445 | | |

| Ser | Tyr | Thr | Pro | Gln | Leu | Gln | Asp | Leu | Asp | Pro | Leu | Ala | Gln | Glu | His |
| 450 | | | | | 455 | | | | | 460 | | | | | |

| Thr | Asp | Ser | Glu | Glu | Gly | Pro | Glu | Glu | Pro | Ser | Thr | Thr | Leu | Val |
| 465 | | | | | 470 | | | | | 475 | | | | | 480 |

| Asp | Trp | Asp | Pro | Gln | Thr | Gly | Arg | Leu | Cys | Ile | Pro | Ser | Leu | Ser | Ser |
| | | | | 485 | | | | | 490 | | | | | 495 | |

| Phe | Asp | Gln | Asp | Ser | Glu | Gly | Cys | Glu | Pro | Ser | Glu | Gly | Asp | Gly | Leu |
| | | | | 500 | | | | | 505 | | | | | 510 | |

| Gly | Glu | Glu | Gly | Leu | Leu | Ser | Arg | Leu | Tyr | Glu | Glu | Pro | Ala | Pro | Asp |
| | | | 515 | | | | | 520 | | | | | 525 | | |

| Arg | Pro | Pro | Gly | Glu | Asn | Glu | Thr | Tyr | Leu | Met | Gln | Phe | Met | Glu | Glu |
| | | | | 530 | | | | | 535 | | | | | 540 | |

| Trp | Gly | Leu | Tyr | Val | Gln | Met | Glu | Asn |
| 545 | | | | | 550 | | | |

(2) INFORMATION FOR SEQ ID NO:35:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:35:

| | | |
|---|---|---|
| ATG CGG GCT CCC GGC CGC CCG GCC CTG CGG CCG CTG CCG CTG CCG CCG<br>Met Arg Ala Pro Gly Arg Pro Ala Leu Arg Pro Leu Pro Leu Pro Pro<br>1                          5                      10                    15 | 48 |
| CTG CTG CTG TTG CTC CTG GCG GCG CCT TGG GGA CGG GCA GTT CCC TGT<br>Leu Leu Leu Leu Leu Leu Ala Ala Pro Trp Gly Arg Ala Val Pro Cys<br>                  20                      25                      30 | 96 |
| GTC TCT GGT GGT TTG CCT AAA CCT GCA AAC ATC ACC TTC TTA TCC ATC<br>Val Ser Gly Gly Leu Pro Lys Pro Ala Asn Ile Thr Phe Leu Ser Ile<br>        35                      40                      45 | 144 |
| AAC ATG AAG AAT GTC CTA CAG TGG ACT CCC CCC GAG GGT CTT CAG GGA<br>Asn Met Lys Asn Val Leu Gln Trp Thr Pro Pro Glu Gly Leu Gln Gly<br>50                        55                      60 | 192 |
| GTT AAA GTT ACT TAC ACT GTG CAG TAT TTC ATA TAT GGG CAG AAG AAA<br>Val Lys Val Thr Tyr Thr Val Gln Tyr Phe Ile Tyr Gly Gln Lys Lys<br>65                        70                      75                      80 | 240 |
| TGG CTG AAT AAA TCA GAA TGC AGA AAT ATC AAT AGA ACC TAC TGT GAT<br>Trp Leu Asn Lys Ser Glu Cys Arg Asn Ile Asn Arg Thr Tyr Cys Asp<br>                      85                      90                      95 | 288 |
| CTT TCT GCT GAA ACT TCT GAC TAC GAA CAC CAG TAT TAT GCC AAA GTT<br>Leu Ser Ala Glu Thr Ser Asp Tyr Glu His Gln Tyr Tyr Ala Lys Val<br>                  100                    105                  110 | 336 |
| AAG GCC ATT TGG GGA ACA AAG TGT TCC AAA TGG GCT GAA AGT GGA CGG<br>Lys Ala Ile Trp Gly Thr Lys Cys Ser Lys Trp Ala Glu Ser Gly Arg<br>            115                    120                    125 | 384 |
| TTC TAT CCT TTT TTA GAA ACA CAG ATT GGC CCC CCC GAG GTG GCA CTG<br>Phe Tyr Pro Phe Leu Glu Thr Gln Ile Gly Pro Pro Glu Val Ala Leu<br>130                        135                    140 | 432 |
| ACT ACA GAT GAG AAG TCC ATT TCT GTT GTC CTG ACA GCT CCC GAG AAG<br>Thr Thr Asp Glu Lys Ser Ile Ser Val Val Leu Thr Ala Pro Glu Lys<br>145                        150                    155                  160 | 480 |
| TGG AAG AGA AAT CCC GAA GAC CTT CCT GTT TCC ATG CAG CAG ATA TAC<br>Trp Lys Arg Asn Pro Glu Asp Leu Pro Val Ser Met Gln Gln Ile Tyr<br>                  165                    170                  175 | 528 |
| TCC AAT CTG AAG TAT AAC GTG TCT GTG TTG AAT ACT AAA TCA AAC AGA<br>Ser Asn Leu Lys Tyr Asn Val Ser Val Leu Asn Thr Lys Ser Asn Arg<br>        180                      185                    190 | 576 |
| ACG TGG TCC CAG TGT GTG ACC AAC CAC ACG CTG GTG CTC ACC TGG CTG<br>Thr Trp Ser Gln Cys Val Thr Asn His Thr Leu Val Leu Thr Trp Leu<br>            195                    200                    205 | 624 |
| GAG CCG AAC ACT CTT TAC TGC GTA CAC GTG GAG TCC TTC GTC CCC GGG<br>Glu Pro Asn Thr Leu Tyr Cys Val His Val Glu Ser Phe Val Pro Gly<br>210                        215                    220 | 672 |
| CCC CCT CGC CGT GCT CAG CCT TCT GAG AAG CAG TGT GCC AGG ACT TTG<br>Pro Pro Arg Arg Ala Gln Pro Ser Glu Lys Gln Cys Ala Arg Thr Leu<br>225                        230                    235                  240 | 720 |
| AAA GAT CAG TCA TCA GAG TTC AAG GCT AAA ATC ATC TTC TGG TAT GTT<br>Lys Asp Gln Ser Ser Glu Phe Lys Ala Lys Ile Ile Phe Trp Tyr Val<br>                  245                    250                  255 | 768 |
| TTG CCC ATA TCT ATT ACC GTG TTT CTT TTT TCT GTG ATG GGC TAT TCC<br>Leu Pro Ile Ser Ile Thr Val Phe Leu Phe Ser Val Met Gly Tyr Ser<br>        260                      265                    270 | 816 |
| ATC TAC CGA TAT ATC CAC GTT GGC AAA GAG AAA CAC CCC GCA AAT TTG<br>Ile Tyr Arg Tyr Ile His Val Gly Lys Glu Lys His Pro Ala Asn Leu<br>            275                    280                    285 | 864 |
| ATT TTG ATT TAT GGA AAT GAA TTT GAC AAA AGA TTC TTT GTG CCT GCT<br>Ile Leu Ile Tyr Gly Asn Glu Phe Asp Lys Arg Phe Phe Val Pro Ala<br>290                        295                    300 | 912 |
| GAA AAA ATC GTG ATT AAC TTT ATC ACC CTC AAT ATC TCG GAT GAT TCT<br>Glu Lys Ile Val Ile Asn Phe Ile Thr Leu Asn Ile Ser Asp Asp Ser<br>305                        310                    315                  320 | 960 |

```
AAA ATT TCT CAT CAG GAT ATG AGT TTA CTG GGA AAA AGC AGT GAT GTA    1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG    1056
Ser Ser Leu Asn Asp Pro Gln Pro Ser Gly Asn Leu Arg Pro Pro Gln
        340                 345                 350

GAG GAA GAG GAG GTG AAA CAT TTA GGG TAT GCT TCG CAT TTG ATG GAA    1104
Glu Glu Glu Glu Val Lys His Leu Gly Tyr Ala Ser His Leu Met Glu
                355                 360                 365

ATT TTT TGT GAC TCT GAA GAA AAC ACG GAA GGT ACT TCT TTC ACC CAG    1152
Ile Phe Cys Asp Ser Glu Glu Asn Thr Glu Gly Thr Ser Phe Thr Gln
        370                 375                 380

CAG GAG TCC CTC AGC AGA ACA ATA CCC CCG GAT AAA ACA GTC ATT GAA    1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG    1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAG GGA ACA TTA TTG    1296
Gln Glu Leu Ser Leu Gln Glu Glu Val Ser Thr Gln Gly Thr Leu Leu
        420                 425                 430

GAG TCG CAG GCA GCG TTG GCA GTC TTG GGC CCG CAG ACG TTA CAG TAC    1344
Glu Ser Gln Ala Ala Leu Ala Val Leu Gly Pro Gln Thr Leu Gln Tyr
            435                 440                 445

TCA TAC ACC CCT CAG CTC CAG GAC TTA GAC CCC CTG GCG CAG GAG CAC    1392
Ser Tyr Thr Pro Gln Leu Gln Asp Leu Asp Pro Leu Ala Gln Glu His
    450                 455                 460

ACA GAC TCG GAG GAG GGG CCG GAG GAA GAG CCC TCG ACG ACC CTG GTC    1440
Thr Asp Ser Glu Glu Gly Pro Glu Glu Glu Pro Ser Thr Thr Leu Val
465                 470                 475                 480

GAC TGG GAT CCC CAG ACT GGC AGG CTG TGT ATT CCT TCG CTG TCC AGC    1488
Asp Trp Asp Pro Gln Thr Gly Arg Leu Cys Ile Pro Ser Leu Ser Ser
                485                 490                 495

TTC GAC CAG GAT TCA GAG GGC TGC GAG CCT TCT GAG GGG GAT GGG CTC    1536
Phe Asp Gln Asp Ser Glu Gly Cys Glu Pro Ser Glu Gly Asp Gly Leu
        500                 505                 510

GGA GAG GAG GGT CTT CTA TCT AGA CTC TAT GAG GAG CCG GCT CCC GAC    1584
Gly Glu Glu Gly Leu Leu Ser Arg Leu Tyr Glu Glu Pro Ala Pro Asp
            515                 520                 525

AGG CCC CCA GGA GAA AAT GAA ACC TAT CTC ATG CAG TTC ATG GAG GAA    1632
Arg Pro Pro Gly Glu Asn Glu Thr Tyr Leu Met Gln Phe Met Glu Glu
    530                 535                 540

TGG GGG TTA TAT GTG CAG ATG GAA AAC                                1659
Trp Gly Leu Tyr Val Gln Met Glu Asn
545                 550

(2) INFORMATION FOR SEQ ID NO:36:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:36:

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
                20                  25                  30
```

-continued

Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
             100                 105                 110

Lys Ala Ile Trp Gly Thr Lys Cys Ser Lys Trp Ala Glu Ser Gly Arg
         115                 120                 125

Phe Tyr Pro Phe Leu Glu Thr Gln Ile Gly Pro Pro Glu Val Ala Leu
     130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                 165                 170                 175

Ser Asn Leu Lys Tyr Asn Val Ser Val Leu Asn Thr Lys Ser Asn Arg
             180                 185                 190

Thr Trp Ser Gln Cys Val Thr Asn His Thr Leu Val Leu Thr Trp Leu
         195                 200                 205

Glu Pro Asn Thr Leu Tyr Cys Val His Val Glu Ser Phe Val Pro Gly
     210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                 245                 250                 255

Leu Pro Ile Ser Ile Thr Val Phe Leu Phe Ser Val Met Gly Tyr Ser
             260                 265                 270

Ile Tyr Arg Tyr Ile His Val Gly Lys Glu Lys His Pro Ala Asn Leu
         275                 280                 285

Ile Leu Ile Tyr Gly Asn Glu Phe Asp Lys Arg Phe Phe Val Pro Ala
     290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                 325                 330                 335

Ser Ser Leu Asn Asp Pro Gln Pro Ser Gly Asn Leu Arg Pro Pro Gln
             340                 345                 350

Glu Glu Glu Glu Val Lys His Leu Gly Tyr Ala Ser His Leu Met Glu
         355                 360                 365

Ile Phe Cys Asp Ser Glu Glu Asn Thr Glu Gly Thr Ser Phe Thr Gln
     370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                 405                 410                 415

Gln Glu Leu Ser Leu Gln Glu Val Ser Thr Gln Gly Thr Leu Leu
             420                 425                 430

Glu Ser Gln Ala Ala Leu Ala Val Leu Gly Pro Gln Thr Leu Gln Tyr
         435                 440                 445

```
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                    485                 490                 495
Phe Asp Gln Asp Ser Glu Gly Cys Glu Pro Ser Glu Gly Asp Gly Leu
                500                 505                 510
Gly Glu Glu Gly Leu Leu Ser Arg Leu Tyr Glu Glu Pro Ala Pro Asp
                515                 520                 525
Arg Pro Pro Gly Glu Asn Glu Thr Tyr Leu Met Gln Phe Met Glu Glu
                530                 535                 540
Trp Gly Leu Tyr Val Gln Met Glu Asn
545                 550
```

(2) INFORMATION FOR SEQ ID NO:37:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:37:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
1               5                   10                  15

CTG CTG CTG TTG CTC CTG GCG GCG CCT TGG GGA CGG GCA GTT CCC TGT        96
Leu Leu Leu Leu Leu Leu Ala Ala Pro Trp Gly Arg Ala Val Pro Cys
            20                  25                  30

GTC TCT GGT GGT TTG CCT AAA CCT GCA AAC ATC ACC TTC TTA TCC ATC       144
Val Ser Gly Gly Leu Pro Lys Pro Ala Asn Ile Thr Phe Leu Ser Ile
        35                  40                  45

AAC ATG AAG AAT GTC CTA CAG TGG ACT CCA CCA GAG GGT CTT CAG GGA       192
Asn Met Lys Asn Val Leu Gln Trp Thr Pro Pro Glu Gly Leu Gln Gly
50                  55                  60

GTT AAA GTT ACT TAC ACT GTG CAG TAT TTC ATA TAT GGG CAG AAG AAA       240
Val Lys Val Thr Tyr Thr Val Gln Tyr Phe Ile Tyr Gly Gln Lys Lys
65                  70                  75                  80

TGG CTG AAT AAA TCA GAA TGC AGG AAT ATC AAT AGG ACC TAC TGT GAT       288
Trp Leu Asn Lys Ser Glu Cys Arg Asn Ile Asn Arg Thr Tyr Cys Asp
                85                  90                  95

CTT TCT GCT GAA ACT TCT GAC TAC GAA CAC CAG TAT TAT GCC AAA GTT       336
Leu Ser Ala Glu Thr Ser Asp Tyr Glu His Gln Tyr Tyr Ala Lys Val
            100                 105                 110

AAG GCC ATT TGG GGA ACA AAG TGT TCC AAA TGG GCT GAA AGT GGA CGG       384
Lys Ala Ile Trp Gly Thr Lys Cys Ser Lys Trp Ala Glu Ser Gly Arg
        115                 120                 125

TTC TAT CCT TTT TTA GAA ACA CAG ATT GGC CCA CCA GAG GTG GCA CTG       432
Phe Tyr Pro Phe Leu Glu Thr Gln Ile Gly Pro Pro Glu Val Ala Leu
130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160
```

```
TGG AAG AGG AAT CCA GAA GAC CTT CCT GTT TCC ATG CAG CAG ATA TAC        528
Trp Lys Arg Asn Pro Glu Asp Leu Pro Val Ser Met Gln Gln Ile Tyr
            165                 170                 175

TCC AAT CTG AAG TAT AAC GTG TCT GTG TTG AAT ACT AAA TCA AAC AGG        576
Ser Asn Leu Lys Tyr Asn Val Ser Val Leu Asn Thr Lys Ser Asn Arg
        180                 185                 190

ACG TGG TCC CAG TGT GTG ACC AAC CAC ACG CTG GTG CTC ACC TGG CTG        624
Thr Trp Ser Gln Cys Val Thr Asn His Thr Leu Val Leu Thr Trp Leu
            195                 200                 205

GAG CCG AAC ACT CTT TAC TGC GTA CAC GTG GAG TCC TTC GTC CCA GGG        672
Glu Pro Asn Thr Leu Tyr Cys Val His Val Glu Ser Phe Val Pro Gly
        210                 215                 220

CCC CCT CGC CGT GCT CAG CCT TCT GAG AAG CAG TGT GCC AGG ACT TTG        720
Pro Pro Arg Arg Ala Gln Pro Ser Glu Lys Gln Cys Ala Arg Thr Leu
225                 230                 235                 240

AAA GAT CAG TCA TCA GAG TTC AAG GCT AAA ATC ATC TTC TGG TAT GTT        768
Lys Asp Gln Ser Ser Glu Phe Lys Ala Lys Ile Ile Phe Trp Tyr Val
            245                 250                 255

TTG CCC ATA TCT ATT ACC GTG TTT CTT TTT TCT GTG ATG GGC TAT TCC        816
Leu Pro Ile Ser Ile Thr Val Phe Leu Phe Ser Val Met Gly Tyr Ser
        260                 265                 270

ATC TAC CGA TAT ATC CAC GTT GGC AAA GAG AAA CAC CCA GCA AAT TTG        864
Ile Tyr Arg Tyr Ile His Val Gly Lys Glu Lys His Pro Ala Asn Leu
            275                 280                 285

ATT TTG ATT TAT GGA AAT GAA TTT GAC AAA AGG TTC TTT GTG CCT GCT        912
Ile Leu Ile Tyr Gly Asn Glu Phe Asp Lys Arg Phe Phe Val Pro Ala
        290                 295                 300

GAA AAA ATC GTG ATT AAC TTT ATC ACC CTC AAT ATC TCG GAT GAT TCT        960
Glu Lys Ile Val Ile Asn Phe Ile Thr Leu Asn Ile Ser Asp Asp Ser
305                 310                 315                 320

AAA ATT TCT CAT CAG GAT ATG AGT TTA CTG GGA AAA AGC AGT GAT GTA       1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG       1056
Ser Ser Leu Asn Asp Pro Gln Pro Ser Gly Asn Leu Arg Pro Pro Gln
        340                 345                 350

GAG GAA GAG GAG GTG AAA CAT TTA GGG TAT GCT TCG CAT TTG ATG GAA       1104
Glu Glu Glu Glu Val Lys His Leu Gly Tyr Ala Ser His Leu Met Glu
            355                 360                 365

ATT TTT TGT GAC TCT GAA GAA AAC ACG GAA GGT ACT TCT TTC ACC CAG       1152
Ile Phe Cys Asp Ser Glu Glu Asn Thr Glu Gly Thr Ser Phe Thr Gln
        370                 375                 380

CAG GAG TCC CTC AGC AGG ACA ATA CCC CCG GAT AAA ACA GTC ATT GAA       1200
Gln Glu Ser Leu Ser Arg Thr Ile Pro Pro Asp Lys Thr Val Ile Glu
385                 390                 395                 400

TAT GAA TAT GAT GTC AGG ACC ACT GAC ATT TGT GCG GGG CCT GAA GAG       1248
Tyr Glu Tyr Asp Val Arg Thr Thr Asp Ile Cys Ala Gly Pro Glu Glu
            405                 410                 415

CAG GAG CTC AGT TTG CAG GAG GAG GTG TCC ACA CAG GGA ACA TTA TTG       1296
Gln Glu Leu Ser Leu Gln Glu Glu Val Ser Thr Gln Gly Thr Leu Leu
        420                 425                 430

GAG TCG CAG GCA GCG TTG GCA GTC TTG GGC CCG CAG ACG TTA CAG TAC       1344
Glu Ser Gln Ala Ala Leu Ala Val Leu Gly Pro Gln Thr Leu Gln Tyr
            435                 440                 445

TCA TAC ACC CCT CAG CTC CAG GAC TTA GAC CCC CTG GCG CAG GAG CAC       1392
Ser Tyr Thr Pro Gln Leu Gln Asp Leu Asp Pro Leu Ala Gln Glu His
        450                 455                 460

ACA GAC TCG GAG GAG GGG CCG GAG GAA GAG CCA TCG ACG ACC CTG GTC       1440
Thr Asp Ser Glu Glu Gly Pro Glu Glu Glu Pro Ser Thr Thr Leu Val
465                 470                 475                 480
```

```
GAC TGG GAT CCC CAG ACT GGC AGG CTG TGT ATT CCT TCG CTG TCC AGC      1488
Asp Trp Asp Pro Gln Thr Gly Arg Leu Cys Ile Pro Ser Leu Ser Ser
                485                 490                 495

TTC GAC CAG GAT TCA GAG GGC TGC GAG CCT TCT GAG GGG GAT GGG CTC      1536
Phe Asp Gln Asp Ser Glu Gly Cys Glu Pro Ser Glu Gly Asp Gly Leu
                500                 505                 510

GGA GAG GAG GGT CTT CTA TCT AGG CTC TAT GAG GAG CCG GCT CCA GAC      1584
Gly Glu Glu Gly Leu Leu Ser Arg Leu Tyr Glu Glu Pro Ala Pro Asp
                515                 520                 525

AGG CCA CCA GGA GAA AAT GAA ACC TAT CTC ATG CAA TTC ATG GAG GAA      1632
Arg Pro Pro Gly Glu Asn Glu Thr Tyr Leu Met Gln Phe Met Glu Glu
        530                 535                 540

TGG GGG TTA TAT GTG CAG ATG GAA AAC                                  1659
Trp Gly Leu Tyr Val Gln Met Glu Asn
545                 550
```

(2) INFORMATION FOR SEQ ID NO:38:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:38:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
                20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240
```

```
Lys Asp Gln Ser Ser Glu Phe Lys Ala Lys Ile Ile Phe Trp Tyr Val
            245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Phe Val Pro Ala
            290                 295                 300

Glu Lys Ile Val Ile Asn Phe Ile Thr Leu Asn Ile Ser Asp Asp Ser
305             310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385             390                 395                 400

Tyr Glu Tyr Asp Val Arg Thr Thr Asp Ile Cys Ala Gly Pro Glu Glu
                405                 410                 415

Gln Glu Leu Ser Leu Gln Glu Val Ser Thr Gln Gly Thr Leu Leu
                420                 425                 430

Glu Ser Gln Ala Ala Leu Ala Val Leu Gly Pro Gln Thr Leu Gln Tyr
            435                 440                 445

Ser Tyr Thr Pro Gln Leu Gln Asp Leu Asp Pro Leu Ala Gln Glu His
            450                 455                 460

Thr Asp Ser Glu Glu Gly Pro Glu Glu Pro Ser Thr Thr Leu Val
465             470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
            515                 520                 525

Arg Pro Pro Gly Glu Asn Glu Thr Tyr Leu Met Gln Phe Met Glu Glu
            530                 535                 540

Trp Gly Leu Tyr Val Gln Met Glu Asn
545                 550
```

(2) INFORMATION FOR SEQ ID NO:39:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:39:

-continued

| | |
|---|---|
| ATG CGG GCT CCC GGC CGC CCG GCC CTG CGG CCG CTG CCG CTG CCG CCG<br>Met Arg Ala Pro Gly Arg Pro Ala Leu Arg Pro Leu Pro Leu Pro Pro<br>1               5                   10                  15 | 48 |
| CTG CTG CTG TTG CTC CTG GCG GCG CCT TGG GGA CGG GCA GTT CCC TGT<br>Leu Leu Leu Leu Leu Leu Ala Ala Pro Trp Gly Arg Ala Val Pro Cys<br>            20                  25                  30 | 96 |
| GTC TCT GGT GGT TTG CCT AAA CCT GCA AAC ATC ACC TTC TTA TCC ATC<br>Val Ser Gly Gly Leu Pro Lys Pro Ala Asn Ile Thr Phe Leu Ser Ile<br>        35                  40                  45 | 144 |
| AAC ATG AAG AAT GTC CTA CAA TGG ACT CCA CCA GAG GGT CTT CAA GGA<br>Asn Met Lys Asn Val Leu Gln Trp Thr Pro Pro Glu Gly Leu Gln Gly<br>    50                  55                  60 | 192 |
| GTT AAA GTT ACT TAC ACT GTG CAG TAT TTC ATA TAT GGG CAA AAG AAA<br>Val Lys Val Thr Tyr Thr Val Gln Tyr Phe Ile Tyr Gly Gln Lys Lys<br>65              70                  75                  80 | 240 |
| TGG CTG AAT AAA TCA GAA TGC AGG AAT ATC AAT AGG ACC TAC TGT GAT<br>Trp Leu Asn Lys Ser Glu Cys Arg Asn Ile Asn Arg Thr Tyr Cys Asp<br>                85                  90                  95 | 288 |
| CTT TCT GCT GAA ACT TCT GAC TAC GAA CAC CAG TAT TAT GCC AAA GTT<br>Leu Ser Ala Glu Thr Ser Asp Tyr Glu His Gln Tyr Tyr Ala Lys Val<br>            100                 105                 110 | 336 |
| AAG GCC ATT TGG GGA ACA AAG TGT TCC AAA TGG GCT GAA AGT GGA CGG<br>Lys Ala Ile Trp Gly Thr Lys Cys Ser Lys Trp Ala Glu Ser Gly Arg<br>        115                 120                 125 | 384 |
| TTC TAT CCT TTT TTA GAA ACA CAA ATT GGC CCA CCA GAG GTG GCA CTG<br>Phe Tyr Pro Phe Leu Glu Thr Gln Ile Gly Pro Pro Glu Val Ala Leu<br>    130                 135                 140 | 432 |
| ACT ACA GAT GAG AAG TCC ATT TCT GTT GTC CTG ACA GCT CCA GAG AAG<br>Thr Thr Asp Glu Lys Ser Ile Ser Val Val Leu Thr Ala Pro Glu Lys<br>145                 150                 155                 160 | 480 |
| TGG AAG AGG AAT CCA GAA GAC CTT CCT GTT TCC ATG CAA CAA ATA TAC<br>Trp Lys Arg Asn Pro Glu Asp Leu Pro Val Ser Met Gln Gln Ile Tyr<br>                165                 170                 175 | 528 |
| TCC AAT CTG AAG TAT AAC GTG TCT GTG TTG AAT ACT AAA TCA AAC AGG<br>Ser Asn Leu Lys Tyr Asn Val Ser Val Leu Asn Thr Lys Ser Asn Arg<br>            180                 185                 190 | 576 |
| ACG TGG TCC CAG TGT GTG ACC AAC CAC ACG CTG GTG CTC ACC TGG CTG<br>Thr Trp Ser Gln Cys Val Thr Asn His Thr Leu Val Leu Thr Trp Leu<br>        195                 200                 205 | 624 |
| GAG CCG AAC ACT CTT TAC TGC GTA CAC GTG GAG TCC TTC GTC CCA GGG<br>Glu Pro Asn Thr Leu Tyr Cys Val His Val Glu Ser Phe Val Pro Gly<br>    210                 215                 220 | 672 |
| CCC CCT CGC CGT GCT CAG CCT TCT GAG AAG CAG TGT GCC AGG ACT TTG<br>Pro Pro Arg Arg Ala Gln Pro Ser Glu Lys Gln Cys Ala Arg Thr Leu<br>225                 230                 235                 240 | 720 |
| AAA GAT CAA TCA TCA GAG TTC AAG GCT AAA ATC ATC TTC TGG TAT GTT<br>Lys Asp Gln Ser Ser Glu Phe Lys Ala Lys Ile Ile Phe Trp Tyr Val<br>                245                 250                 255 | 768 |
| TTG CCC ATA TCT ATT ACC GTG TTT CTT TTT TCT GTG ATG GGC TAT TCC<br>Leu Pro Ile Ser Ile Thr Val Phe Leu Phe Ser Val Met Gly Tyr Ser<br>            260                 265                 270 | 816 |
| ATC TAC CGA TAT ATC CAC GTT GGC AAA GAG AAA CAC CCA GCA AAT TTG<br>Ile Tyr Arg Tyr Ile His Val Gly Lys Glu Lys His Pro Ala Asn Leu<br>        275                 280                 285 | 864 |
| ATT TTG ATT TAT GGA AAT GAA TTT GAC AAA AGG TTC TTT GTG CCT GCT<br>Ile Leu Ile Tyr Gly Asn Glu Phe Asp Lys Arg Phe Phe Val Pro Ala<br>    290                 295                 300 | 912 |
| GAA AAA ATC GTG ATT AAC TTT ATC ACC CTC AAT ATC TCG GAT GAT TCT<br>Glu Lys Ile Val Ile Asn Phe Ile Thr Leu Asn Ile Ser Asp Asp Ser<br>305                 310                 315                 320 | 960 |

```
AAA ATT TCT CAT CAG GAT ATG AGT TTA CTG GGA AAA AGT AGT GAT GTA      1008
Lys Ile Ser His Gln Asp Met Ser Leu Leu Gly Lys Ser Ser Asp Val
            325                 330                 335

TCC AGT CTT AAT GAT CCT CAG CCC AGT GGG AAC CTG AGG CCC CCT CAG      1056
Ser Ser Leu Asn Asp Pro Gln Pro Ser Gly Asn Leu Arg Pro Pro Gln
            340                 345                 350

GAG GAA GAG GAG GTG AAA CAT TTA GGG TAT GCT TCG CAT TTG ATG GAA      1104
Glu Glu Glu Glu Val Lys His Leu Gly Tyr Ala Ser His Leu Met Glu
            355                 360                 365

ATT TTT TGT GAC TCT GAA GAA AAC ACG GAA GGT ACT TCT TTC ACC CAG      1152
Ile Phe Cys Asp Ser Glu Glu Asn Thr Glu Gly Thr Ser Phe Thr Gln
        370                 375                 380

CAA GAG TCC CTC AGT AGG ACA ATA CCC CCG GAT AAA ACA GTC ATT GAA      1200
Gln Glu Ser Leu Ser Arg Thr Ile Pro Pro Asp Lys Thr Val Ile Glu
385                 390                 395                 400

TAT GAA TAT GAT GTC AGG ACC ACT GAC ATT TGT GCG GGG CCT GAA GAG      1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACA CAA GGA ACA TTA TTG      1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC      1344
Glu Ser Gln Ala Ala Leu Ala Val Leu Gly Pro Gln Thr Leu Gln Tyr
            435                 440                 445

TCA TAC ACC CCT CAG CTC CAA GAC TTA GAC CCC CTG GCG CAG GAG CAC      1392
Ser Tyr Thr Pro Gln Leu Gln Asp Leu Asp Pro Leu Ala Gln Glu His
            450                 455                 460

ACA GAC TCG GAG GAG GGG CCG GAG GAA GAG CCA TCG ACG ACC CTG GTC      1440
Thr Asp Ser Glu Glu Gly Pro Glu Glu Glu Pro Ser Thr Thr Leu Val
465                 470                 475                 480

GAC TGG GAT CCC CAA ACT GGC AGG CTG TGT ATT CCT TCG CTG TCC AGT      1488
Asp Trp Asp Pro Gln Thr Gly Arg Leu Cys Ile Pro Ser Leu Ser Ser
            485                 490                 495

TTC GAC CAG GAT TCA GAG GGC TGC GAG CCT TCT GAG GGG GAT GGG CTC      1536
Phe Asp Gln Asp Ser Glu Gly Cys Glu Pro Ser Glu Gly Asp Gly Leu
            500                 505                 510

GGA GAG GAG GGT CTT CTA TCT AGG CTC TAT GAG GAG CCG GCT CCA GAC      1584
Gly Glu Glu Gly Leu Leu Ser Arg Leu Tyr Glu Glu Pro Ala Pro Asp
            515                 520                 525

AGG CCA CCA GGA GAA AAT GAA ACC TAT CTC ATG CAA TTC ATG GAG GAA      1632
Arg Pro Pro Gly Glu Asn Glu Thr Tyr Leu Met Gln Phe Met Glu Glu
            530                 535                 540

TGG GGG TTA TAT GTG CAG ATG GAA AAC                                  1659
Trp Gly Leu Tyr Val Gln Met Glu Asn
545                 550
```

(2) INFORMATION FOR SEQ ID NO:40:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:40:

```
Met Arg Ala Pro Gly Arg Pro Ala Leu Arg Pro Leu Pro Leu Pro Pro
1               5                   10                  15

Leu Leu Leu Leu Leu Ala Ala Pro Trp Gly Arg Ala Val Pro Cys
            20                  25                  30
```

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
 50                  55                  60

Val Lys Val Thr Tyr Thr Val Gln Tyr Phe Ile Tyr Gly Gln Lys Lys
 65              70                  75                      80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125

Phe Tyr Pro Phe Leu Glu Thr Gln Ile Gly Pro Pro Glu Val Ala Leu
        130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
        210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
        290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
        355                 360                 365

Ile Phe Cys Asp Ser Glu Glu Asn Thr Glu Gly Thr Ser Phe Thr Gln
        370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445
```

```
Ser Tyr Thr Pro Gln Leu Gln Asp Leu Asp Pro Leu Ala Gln Glu His
    450                 455                 460
Thr Asp Ser Glu Glu Gly Pro Glu Glu Pro Ser Thr Thr Leu Val
465                 470                 475                 480
Asp Trp Asp Pro Gln Thr Gly Arg Leu Cys Ile Pro Ser Leu Ser Ser
                    485                 490                 495
Phe Asp Gln Asp Ser Glu Gly Cys Glu Pro Ser Glu Gly Asp Gly Leu
                500                 505                 510
Gly Glu Glu Gly Leu Leu Ser Arg Leu Tyr Glu Glu Pro Ala Pro Asp
            515                 520                 525
Arg Pro Pro Gly Glu Asn Glu Thr Tyr Leu Met Gln Phe Met Glu Glu
    530                 535                 540
Trp Gly Leu Tyr Val Gln Met Glu Asn
545                 550
```

(2) INFORMATION FOR SEQ ID NO:41:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:41:

```
ATG CGG GCT CCC GGC CGC CCG GCC CTG CGG CCG CTG CCG CTG CCG CCG         48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGA CGG GCA GTT CCC TGT         96
Leu Leu Leu Leu Leu Leu Ala Ala Pro Trp Gly Arg Ala Val Pro Cys
             20                  25                  30

GTC TCT GGT GGT TTG CCT AAA CCT GCA AAC ATC ACC TTC TTA TCC ATC        144
Val Ser Gly Gly Leu Pro Lys Pro Ala Asn Ile Thr Phe Leu Ser Ile
         35                  40                  45

AAC ATG AAG AAT GTC CTA CAA TGG ACT CCA CCA GAG GGT CTT CAA GGA        192
Asn Met Lys Asn Val Leu Gln Trp Thr Pro Pro Glu Gly Leu Gln Gly
     50                  55                  60

GTT AAA GTT ACT TAC ACT GTG CAG TAT TTC ATA TAT GGG CAA AAG AAA        240
Val Lys Val Thr Tyr Thr Val Gln Tyr Phe Ile Tyr Gly Gln Lys Lys
 65                  70                  75                  80

TGG CTG AAT AAA TCA GAA TGC AGA AAT ATC AAT AGA ACC TAC TGT GAT        288
Trp Leu Asn Lys Ser Glu Cys Arg Asn Ile Asn Arg Thr Tyr Cys Asp
                 85                  90                  95

CTT TCT GCT GAA ACT TCT GAC TAC GAA CAC CAG TAT TAT GCC AAA GTT        336
Leu Ser Ala Glu Thr Ser Asp Tyr Glu His Gln Tyr Tyr Ala Lys Val
            100                 105                 110

AAG GCC ATT TGG GGA ACC AAG TGT TCC AAA TGG GCT GAA AGT GGA CGG        384
Lys Ala Ile Trp Gly Thr Lys Cys Ser Lys Trp Ala Glu Ser Gly Arg
        115                 120                 125

TTC TAT CCT TTT TTA GAA ACC CAA ATT GGC CCA CCA GAG GTG GCA CTG        432
Phe Tyr Pro Phe Leu Glu Thr Gln Ile Gly Pro Pro Glu Val Ala Leu
    130                 135                 140

ACT ACC GAT GAG AAG TCC ATT TCT GTT GTC CTG ACC GCT CCA GAG AAG        480
Thr Thr Asp Glu Lys Ser Ile Ser Val Val Leu Thr Ala Pro Glu Lys
145                 150                 155                 160
```

| | | | | | | | | | | | | | | | | |
|---|---|---|---|---|---|---|---|---|---|---|---|---|---|---|---|---|
| TGG | AAG | AGA | AAT | CCA | GAA | GAC | CTT | CCT | GTT | TCC | ATG | CAA | CAA | ATA | TAC | 528 |
| Trp | Lys | Arg | Asn | Pro | Glu | Asp | Leu | Pro | Val | Ser | Met | Gln | Gln | Ile | Tyr | |
| | | | | 165 | | | | | 170 | | | | | 175 | | |
| TCC | AAT | CTG | AAG | TAT | AAC | GTG | TCT | GTG | TTG | AAT | ACT | AAA | TCA | AAC | AGA | 576 |
| Ser | Asn | Leu | Lys | Tyr | Asn | Val | Ser | Val | Leu | Asn | Thr | Lys | Ser | Asn | Arg | |
| | | | 180 | | | | | 185 | | | | | 190 | | | |
| ACG | TGG | TCC | CAG | TGT | GTG | ACC | AAC | CAC | ACG | CTG | GTG | CTC | ACC | TGG | CTG | 624 |
| Thr | Trp | Ser | Gln | Cys | Val | Thr | Asn | His | Thr | Leu | Val | Leu | Thr | Trp | Leu | |
| | | | 195 | | | | | 200 | | | | | 205 | | | |
| GAG | CCG | AAC | ACT | CTT | TAC | TGC | GTA | CAC | GTG | GAG | TCC | TTC | GTC | CCA | GGG | 672 |
| Glu | Pro | Asn | Thr | Leu | Tyr | Cys | Val | His | Val | Glu | Ser | Phe | Val | Pro | Gly | |
| | | 210 | | | | | 215 | | | | | 220 | | | | |
| CCC | CCT | CGC | CGT | GCT | CAG | CCT | TCT | GAG | AAG | CAG | TGT | GCC | AGG | ACT | TTG | 720 |
| Pro | Pro | Arg | Arg | Ala | Gln | Pro | Ser | Glu | Lys | Gln | Cys | Ala | Arg | Thr | Leu | |
| 225 | | | | | 230 | | | | | 235 | | | | | 240 | |
| AAA | GAT | CAA | TCA | TCA | GAG | TTC | AAG | GCT | AAA | ATC | ATC | TTC | TGG | TAT | GTT | 768 |
| Lys | Asp | Gln | Ser | Ser | Glu | Phe | Lys | Ala | Lys | Ile | Ile | Phe | Trp | Tyr | Val | |
| | | | | 245 | | | | | 250 | | | | | 255 | | |
| TTG | CCC | ATA | TCT | ATT | ACC | GTG | TTT | CTT | TTT | TCT | GTG | ATG | GGC | TAT | TCC | 816 |
| Leu | Pro | Ile | Ser | Ile | Thr | Val | Phe | Leu | Phe | Ser | Val | Met | Gly | Tyr | Ser | |
| | | | | 260 | | | | | 265 | | | | | 270 | | |
| ATC | TAC | CGA | TAT | ATC | CAC | GTT | GGC | AAA | GAG | AAA | CAC | CCA | GCA | AAT | TTG | 864 |
| Ile | Tyr | Arg | Tyr | Ile | His | Val | Gly | Lys | Glu | Lys | His | Pro | Ala | Asn | Leu | |
| | | | 275 | | | | | 280 | | | | | 285 | | | |
| ATT | TTG | ATT | TAT | GGA | AAT | GAA | TTT | GAC | AAA | AGA | TTC | TTT | GTG | CCT | GCT | 912 |
| Ile | Leu | Ile | Tyr | Gly | Asn | Glu | Phe | Asp | Lys | Arg | Phe | Phe | Val | Pro | Ala | |
| | | | 290 | | | | | 295 | | | | | 300 | | | |
| GAA | AAA | ATC | GTG | ATT | AAC | TTT | ATC | ACC | CTC | AAT | ATC | TCG | GAT | GAT | TCT | 960 |
| Glu | Lys | Ile | Val | Ile | Asn | Phe | Ile | Thr | Leu | Asn | Ile | Ser | Asp | Asp | Ser | |
| 305 | | | | | 310 | | | | | 315 | | | | | 320 | |
| AAA | ATT | TCT | CAT | CAG | GAT | ATG | AGT | TTA | CTG | GGA | AAA | AGT | AGT | GAT | GTA | 1008 |
| Lys | Ile | Ser | His | Gln | Asp | Met | Ser | Leu | Leu | Gly | Lys | Ser | Ser | Asp | Val | |
| | | | | 325 | | | | | 330 | | | | | 335 | | |
| TCC | AGT | CTT | AAT | GAT | CCT | CAG | CCC | AGT | GGG | AAC | CTG | AGG | CCC | CCT | CAG | 1056 |
| Ser | Ser | Leu | Asn | Asp | Pro | Gln | Pro | Ser | Gly | Asn | Leu | Arg | Pro | Pro | Gln | |
| | | | 340 | | | | | 345 | | | | | 350 | | | |
| GAG | GAA | GAG | GAG | GTG | AAA | CAT | TTA | GGG | TAT | GCT | TCG | CAT | TTG | ATG | GAA | 1104 |
| Glu | Glu | Glu | Glu | Val | Lys | His | Leu | Gly | Tyr | Ala | Ser | His | Leu | Met | Glu | |
| | | | 355 | | | | | 360 | | | | | 365 | | | |
| ATT | TTT | TGT | GAC | TCT | GAA | GAA | AAC | ACG | GAA | GGT | ACT | TCT | TTC | ACC | CAG | 1152 |
| Ile | Phe | Cys | Asp | Ser | Glu | Glu | Asn | Thr | Glu | Gly | Thr | Ser | Phe | Thr | Gln | |
| | | | 370 | | | | | 375 | | | | | 380 | | | |
| CAA | GAG | TCC | CTC | AGT | AGA | ACC | ATA | CCC | CCG | GAT | AAA | ACC | GTC | ATT | GAA | 1200 |
| Gln | Glu | Ser | Leu | Ser | Arg | Thr | Ile | Pro | Pro | Asp | Lys | Thr | Val | Ile | Glu | |
| 385 | | | | | 390 | | | | | 395 | | | | | 400 | |
| TAT | GAA | TAT | GAT | GTC | AGA | ACC | ACT | GAC | ATT | TGT | GCG | GGG | CCT | GAA | GAG | 1248 |
| Tyr | Glu | Tyr | Asp | Val | Arg | Thr | Thr | Asp | Ile | Cys | Ala | Gly | Pro | Glu | Glu | |
| | | | | 405 | | | | | 410 | | | | | 415 | | |
| CAG | GAG | CTC | AGT | TTG | CAG | GAG | GAG | GTG | TCC | ACC | CAA | GGA | ACC | TTA | TTG | 1296 |
| Gln | Glu | Leu | Ser | Leu | Gln | Glu | Glu | Val | Ser | Thr | Gln | Gly | Thr | Leu | Leu | |
| | | | 420 | | | | | 425 | | | | | 430 | | | |
| GAG | TCG | CAG | GCA | GCG | TTG | GCA | GTC | TTG | GGC | CCG | CAA | ACG | TTA | CAG | TAC | 1344 |
| Glu | Ser | Gln | Ala | Ala | Leu | Ala | Val | Leu | Gly | Pro | Gln | Thr | Leu | Gln | Tyr | |
| | | | 435 | | | | | 440 | | | | | 445 | | | |
| TCA | TAC | ACC | CCT | CAG | CTC | CAA | GAC | TTA | GAC | CCC | CTG | GCG | CAG | GAG | CAC | 1392 |
| Ser | Tyr | Thr | Pro | Gln | Leu | Gln | Asp | Leu | Asp | Pro | Leu | Ala | Gln | Glu | His | |
| | | | 450 | | | | | 455 | | | | | 460 | | | |
| ACC | GAC | TCG | GAG | GAG | GGG | CCG | GAG | GAA | GAG | CCA | TCG | ACG | ACC | CTG | GTC | 1440 |
| Thr | Asp | Ser | Glu | Glu | Gly | Pro | Glu | Glu | Glu | Pro | Ser | Thr | Thr | Leu | Val | |
| 465 | | | | | 470 | | | | | 475 | | | | | 480 | |

-continued

```
GAC TGG GAT CCC CAA ACT GGC AGG CTG TGT ATT CCT TCG CTG TCC AGT       1488
Asp Trp Asp Pro Gln Thr Gly Arg Leu Cys Ile Pro Ser Leu Ser Ser
            485                 490                 495

TTC GAC CAG GAT TCA GAG GGC TGC GAG CCT TCT GAG GGG GAT GGG CTC       1536
Phe Asp Gln Asp Ser Glu Gly Cys Glu Pro Ser Glu Gly Asp Gly Leu
                500                 505                 510

GGA GAG GAG GGT CTT CTA TCT AGA CTC TAT GAG GAG CCG GCT CCA GAC       1584
Gly Glu Glu Gly Leu Leu Ser Arg Leu Tyr Glu Glu Pro Ala Pro Asp
            515                 520                 525

AGG CCA CCA GGA GAA AAT GAA ACC TAT CTC ATG CAA TTC ATG GAG GAA       1632
Arg Pro Pro Gly Glu Asn Glu Thr Tyr Leu Met Gln Phe Met Glu Glu
        530                 535                 540

TGG GGG TTA TAT GTG CAG ATG GAA AAC                                   1659
Trp Gly Leu Tyr Val Gln Met Glu Asn
545                 550
```

(2) INFORMATION FOR SEQ ID NO:42:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:42:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
        35                  40                  45

Asn Met Lys Asn Val Leu Gln Trp Thr Pro Glu Gly Leu Gln Gly
    50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
        115                 120                 125

Phe Tyr Pro Phe Leu Glu Thr Gln Ile Gly Pro Pro Glu Val Ala Leu
    130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240
```

Lys Asp Gln Ser Ser Glu Phe Lys Ala Lys Ile Ile Phe Trp Tyr Val
            245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Phe Val Pro Ala
            290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
            325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
            355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
            405                 410                 415

Gln Glu Leu Ser Leu Gln Glu Val Ser Thr Gln Gly Thr Leu Leu
            420                 425                 430

Glu Ser Gln Ala Ala Leu Ala Val Leu Gly Pro Gln Thr Leu Gln Tyr
            435                 440                 445

Ser Tyr Thr Pro Gln Leu Gln Asp Leu Asp Pro Leu Ala Gln Glu His
            450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
            485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
            515                 520                 525

Arg Pro Pro Gly Glu Asn Glu Thr Tyr Leu Met Gln Phe Met Glu Glu
            530                 535                 540

Trp Gly Leu Tyr Val Gln Met Glu Asn
545                 550

(2) INFORMATION FOR SEQ ID NO:43:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:43:

```
ATG CGG GCT CCC GGC CGC CCG GCC CTG CGG CCG CTG CCG CTG CCG CCG    48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGA CGG GCA GTT CCC TGT    96
Leu Leu Leu Leu Leu Leu Ala Ala Pro Trp Gly Arg Ala Val Pro Cys
             20                  25                  30

GTC TCT GGT GGT TTG CCT AAA CCT GCA AAC ATC ACC TTC TTA TCC ATC   144
Val Ser Gly Gly Leu Pro Lys Pro Ala Asn Ile Thr Phe Leu Ser Ile
         35                  40                  45

AAC ATG AAG AAT GTC CTA CAA TGG ACT CCA CCA GAG GGT CTT CAA GGA   192
Asn Met Lys Asn Val Leu Gln Trp Thr Pro Pro Glu Gly Leu Gln Gly
 50                  55                  60

GTT AAA GTT ACT TAC ACT GTG CAG TAT TTC ATA TAT GGG CAA AAG AAA   240
Val Lys Val Thr Tyr Thr Val Gln Tyr Phe Ile Tyr Gly Gln Lys Lys
 65                  70                  75                  80

TGG CTG AAT AAA TCA GAA TGC AGA AAT ATC AAT AGA ACC TAC TGT GAT   288
Trp Leu Asn Lys Ser Glu Cys Arg Asn Ile Asn Arg Thr Tyr Cys Asp
                 85                  90                  95

CTT TCT GCT GAA ACT TCT GAC TAC GAA CAC CAG TAT TAT GCC AAA GTT   336
Leu Ser Ala Glu Thr Ser Asp Tyr Glu His Gln Tyr Tyr Ala Lys Val
            100                 105                 110

AAG GCC ATT TGG GGA ACC AAG TGT TCC AAA TGG GCT GAA AGT GGA CGG   384
Lys Ala Ile Trp Gly Thr Lys Cys Ser Lys Trp Ala Glu Ser Gly Arg
            115                 120                 125

TTC TAT CCT TTT TTA GAA ACC CAA ATT GGC CCA CCA GAG GTG GCA CTG   432
Phe Tyr Pro Phe Leu Glu Thr Gln Ile Gly Pro Pro Glu Val Ala Leu
130                 135                 140

ACT ACC GAT GAG AAG TCC ATT TCT GTT GTC CTG ACC GCT CCA GAG AAG   480
Thr Thr Asp Glu Lys Ser Ile Ser Val Val Leu Thr Ala Pro Glu Lys
145                 150                 155                 160

TGG AAG AGA AAT CCA GAA GAC CTT CCT GTT TCC ATG CAA CAA ATA TAC   528
Trp Lys Arg Asn Pro Glu Asp Leu Pro Val Ser Met Gln Gln Ile Tyr
                165                 170                 175

TCC AAT CTG AAG TAT AAC GTG TCT GTG TTG AAT ACT AAA TCA AAC AGA   576
Ser Asn Leu Lys Tyr Asn Val Ser Val Leu Asn Thr Lys Ser Asn Arg
            180                 185                 190

ACG TGG TCC CAG TGT GTG ACC AAC CAC ACG CTG GTG CTC ACC TGG CTG   624
Thr Trp Ser Gln Cys Val Thr Asn His Thr Leu Val Leu Thr Trp Leu
            195                 200                 205

GAG CCG AAC ACT CTT TAC TGC GTC CAC GTG GAG TCC TTC GTC CCA GGG   672
Glu Pro Asn Thr Leu Tyr Cys Val His Val Glu Ser Phe Val Pro Gly
210                 215                 220

CCC CCT CGC CGT GCT CAG CCT TCT GAG AAG CAG TGT GCC AGG ACT TTG   720
Pro Pro Arg Arg Ala Gln Pro Ser Glu Lys Gln Cys Ala Arg Thr Leu
225                 230                 235                 240

AAA GAT CAA TCA TCA GAG TTC AAG GCT AAA ATC ATC TTC TGG TAT GTT   768
Lys Asp Gln Ser Ser Glu Phe Lys Ala Lys Ile Ile Phe Trp Tyr Val
                245                 250                 255

TTG CCC ATA TCT ATT ACC GTG TTT CTT TTT TCT GTG ATG GGC TAT TCC   816
Leu Pro Ile Ser Ile Thr Val Phe Leu Phe Ser Val Met Gly Tyr Ser
            260                 265                 270

ATC TAC CGA TAT ATC CAC GTT GGC AAA GAG AAA CAC CCA GCA AAT TTG   864
Ile Tyr Arg Tyr Ile His Val Gly Lys Glu Lys His Pro Ala Asn Leu
            275                 280                 285

ATT TTG ATT TAT GGA AAT GAA TTT GAC AAA AGA TTC TTT GTG CCT GCT   912
Ile Leu Ile Tyr Gly Asn Glu Phe Asp Lys Arg Phe Phe Val Pro Ala
290                 295                 300

GAA AAA ATC GTG ATT AAC TTT ATC ACC CTC AAT ATC TCG GAT GAT TCT   960
Glu Lys Ile Val Ile Asn Phe Ile Thr Leu Asn Ile Ser Asp Asp Ser
305                 310                 315                 320
```

```
AAA ATT TCT CAT CAG GAT ATG AGT TTA CTG GGA AAA AGC AGT GAT GTC     1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG     1056
Ser Ser Leu Asn Asp Pro Gln Pro Ser Gly Asn Leu Arg Pro Pro Gln
        340                 345                 350

GAG GAA GAG GAG GTG AAA CAT TTA GGG TAT GCT TCG CAT TTG ATG GAA     1104
Glu Glu Glu Glu Val Lys His Leu Gly Tyr Ala Ser His Leu Met Glu
    355                 360                 365

ATT TTT TGT GAC TCT GAA GAA AAC ACG GAA GGT ACT TCT TTC ACC CAG     1152
Ile Phe Cys Asp Ser Glu Glu Asn Thr Glu Gly Thr Ser Phe Thr Gln
370                 375                 380

CAA GAG TCC CTC AGC AGA ACC ATA CCC CCG GAT AAA ACC GTC ATT GAA     1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG     1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACC CAA GGA ACC TTA TTG     1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAC     1344
Glu Ser Gln Ala Ala Leu Ala Val Leu Gly Pro Gln Thr Leu Gln Tyr
        435                 440                 445

TCA TAC ACC CCT CAG CTC CAA GAC TTA GAC CCC CTG GCG CAG GAG CAC     1392
Ser Tyr Thr Pro Gln Leu Gln Asp Leu Asp Pro Leu Ala Gln Glu His
    450                 455                 460

ACC GAC TCG GAG GAG GGG CCG GAG GAA GAG CCA TCG ACG ACC CTG GTC     1440
Thr Asp Ser Glu Glu Gly Pro Glu Glu Glu Pro Ser Thr Thr Leu Val
465                 470                 475                 480

GAC TGG GAT CCC CAA ACT GGC AGG CTG TGT ATT CCT TCG CTG TCC AGC     1488
Asp Trp Asp Pro Gln Thr Gly Arg Leu Cys Ile Pro Ser Leu Ser Ser
                485                 490                 495

TTC GAC CAG GAT TCA GAG GGC TGC GAG CCT TCT GAG GGG GAT GGG CTC     1536
Phe Asp Gln Asp Ser Glu Gly Cys Glu Pro Ser Glu Gly Asp Gly Leu
            500                 505                 510

GGA GAG GAG GGT CTT CTA TCT AGA CTC TAT GAG GAG CCG GCT CCA GAC     1584
Gly Glu Glu Gly Leu Leu Ser Arg Leu Tyr Glu Glu Pro Ala Pro Asp
        515                 520                 525

AGG CCA CCA GGA GAA AAT GAA ACC TAT CTC ATG CAA TTC ATG GAG GAA     1632
Arg Pro Pro Gly Glu Asn Glu Thr Tyr Leu Met Gln Phe Met Glu Glu
    530                 535                 540

TGG GGG TTA TAT GTG CAG ATG GAA AAC                                 1659
Trp Gly Leu Tyr Val Gln Met Glu Asn
545                 550
```

(2) INFORMATION FOR SEQ ID NO:44:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:44:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30
```

```
Val Ser Gly Gly Leu Pro Lys Pro Ala Asn Ile Thr Phe Leu Ser Ile
            35                  40                  45

Asn Met Lys Asn Val Leu Gln Trp Thr Pro Pro Glu Gly Leu Gln Gly
 50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
            275                 280                 285

Ile Leu Ile Tyr Gly Asn Glu Phe Asp Lys Arg Phe Phe Val Pro Ala
            290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
            355                 360                 365

Ile Phe Cys Asp Ser Glu Glu Asn Thr Glu Gly Thr Ser Phe Thr Gln
            370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Val Ser Thr Gln Gly Thr Leu Leu
            420                 425                 430

Glu Ser Gln Ala Ala Leu Ala Val Leu Gly Pro Gln Thr Leu Gln Tyr
            435                 440                 445
```

```
Ser Tyr Thr Pro Gln Leu Gln Asp Leu Asp Pro Leu Ala Gln Glu His
    450             455             460

Thr Asp Ser Glu Glu Gly Pro Glu Glu Pro Ser Thr Thr Leu Val
465             470             475             480

Asp Trp Asp Pro Gln Thr Gly Arg Leu Cys Ile Pro Ser Leu Ser Ser
                485             490             495

Phe Asp Gln Asp Ser Glu Gly Cys Glu Pro Ser Glu Gly Asp Gly Leu
            500             505             510

Gly Glu Glu Gly Leu Leu Ser Arg Leu Tyr Glu Glu Pro Ala Pro Asp
        515             520             525

Arg Pro Pro Gly Glu Asn Glu Thr Tyr Leu Met Gln Phe Met Glu Glu
    530             535             540

Trp Gly Leu Tyr Val Gln Met Glu Asn
545             550
```

(2) INFORMATION FOR SEQ ID NO:45:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:45:

```
ATG CGG GCT CCC GGC CGC CCG GCC CTG CGG CCG CTG CCG CTG CCG CCG        48
Met Arg Ala Pro Gly Arg Pro Ala Leu Arg Pro Leu Pro Leu Pro Pro
1               5                   10                  15

CTG CTG CTG TTG CTC CTG GCG GCG CCT TGG GGA CGG GCA GTT CCC TGT        96
Leu Leu Leu Leu Leu Leu Ala Ala Pro Trp Gly Arg Ala Val Pro Cys
            20                  25                  30

GTC TCT GGT GGT TTG CCT AAA CCT GCA AAC ATC ACC TTC TTA TCC ATC       144
Val Ser Gly Gly Leu Pro Lys Pro Ala Asn Ile Thr Phe Leu Ser Ile
        35                  40                  45

AAC ATG AAG AAT GTC CTA CAA TGG ACT CCA CCA GAG GGT CTT CAA GGA       192
Asn Met Lys Asn Val Leu Gln Trp Thr Pro Pro Glu Gly Leu Gln Gly
    50                  55                  60

GTT AAA GTT ACT TAT ACT GTG CAG TAT TTC ATA TAT GGG CAA AAG AAA       240
Val Lys Val Thr Tyr Thr Val Gln Tyr Phe Ile Tyr Gly Gln Lys Lys
65                  70                  75                  80

TGG CTG AAT AAA TCA GAA TGC AGA AAT ATC AAT AGA ACC TAT TGT GAT       288
Trp Leu Asn Lys Ser Glu Cys Arg Asn Ile Asn Arg Thr Tyr Cys Asp
                85                  90                  95

CTT TCT GCT GAA ACT TCT GAC TAT GAA CAC CAG TAT TAT GCC AAA GTT       336
Leu Ser Ala Glu Thr Ser Asp Tyr Glu His Gln Tyr Tyr Ala Lys Val
            100                 105                 110

AAG GCC ATT TGG GGA ACA AAG TGT TCC AAA TGG GCT GAA AGT GGA CGG       384
Lys Ala Ile Trp Gly Thr Lys Cys Ser Lys Trp Ala Glu Ser Gly Arg
        115                 120                 125

TTC TAT CCT TTT TTA GAA ACA CAA ATT GGC CCA CCA GAG GTG GCA CTG       432
Phe Tyr Pro Phe Leu Glu Thr Gln Ile Gly Pro Pro Glu Val Ala Leu
    130                 135                 140

ACT ACA GAT GAG AAG TCC ATT TCT GTT GTC CTG ACA GCT CCA GAG AAG       480
Thr Thr Asp Glu Lys Ser Ile Ser Val Val Leu Thr Ala Pro Glu Lys
145                 150                 155                 160
```

```
TGG AAG AGA AAT CCA GAA GAC CTT CCT GTT TCC ATG CAA CAA ATA TAT      528
Trp Lys Arg Asn Pro Glu Asp Leu Pro Val Ser Met Gln Gln Ile Tyr
            165                 170                 175

TCC AAT CTG AAG TAT AAC GTG TCT GTG TTG AAT ACT AAA TCA AAC AGA      576
Ser Asn Leu Lys Tyr Asn Val Ser Val Leu Asn Thr Lys Ser Asn Arg
            180                 185                 190

ACG TGG TCC CAG TGT GTG ACC AAC CAC ACG CTG GTG CTC ACC TGG CTG      624
Thr Trp Ser Gln Cys Val Thr Asn His Thr Leu Val Leu Thr Trp Leu
            195                 200                 205

GAG CCG AAC ACT CTT TAT TGC GTC CAC GTG GAG TCC TTC GTC CCA GGG      672
Glu Pro Asn Thr Leu Tyr Cys Val His Val Glu Ser Phe Val Pro Gly
210                 215                 220

CCC CCT CGC CGT GCT CAG CCT TCT GAG AAG CAG TGT GCC AGG ACT TTG      720
Pro Pro Arg Arg Ala Gln Pro Ser Glu Lys Gln Cys Ala Arg Thr Leu
225                 230                 235                 240

AAA GAT CAA TCA TCA GAG TTC AAG GCT AAA ATC ATC TTC TGG TAT GTT      768
Lys Asp Gln Ser Ser Glu Phe Lys Ala Lys Ile Ile Phe Trp Tyr Val
            245                 250                 255

TTG CCC ATA TCT ATT ACC GTG TTT CTT TTT TCT GTG ATG GGC TAT TCC      816
Leu Pro Ile Ser Ile Thr Val Phe Leu Phe Ser Val Met Gly Tyr Ser
            260                 265                 270

ATC TAT CGA TAT ATC CAC GTT GGC AAA GAG AAA CAC CCA GCA AAT TTG      864
Ile Tyr Arg Tyr Ile His Val Gly Lys Glu Lys His Pro Ala Asn Leu
            275                 280                 285

ATT TTG ATT TAT GGA AAT GAA TTT GAC AAA AGA TTC TTT GTG CCT GCT      912
Ile Leu Ile Tyr Gly Asn Glu Phe Asp Lys Arg Phe Phe Val Pro Ala
290                 295                 300

GAA AAA ATC GTG ATT AAC TTT ATC ACC CTC AAT ATC TCG GAT GAT TCT      960
Glu Lys Ile Val Ile Asn Phe Ile Thr Leu Asn Ile Ser Asp Asp Ser
305                 310                 315                 320

AAA ATT TCT CAT CAG GAT ATG AGT TTA CTG GGA AAA AGC AGT GAT GTC     1008
Lys Ile Ser His Gln Asp Met Ser Leu Leu Gly Lys Ser Ser Asp Val
            325                 330                 335

TCC AGC CTT AAT GAT CCT CAG CCC AGC GGG AAC CTG AGG CCC CCT CAG     1056
Ser Ser Leu Asn Asp Pro Gln Pro Ser Gly Asn Leu Arg Pro Pro Gln
            340                 345                 350

GAG GAA GAG GAG GTG AAA CAT TTA GGG TAT GCT TCG CAT TTG ATG GAA     1104
Glu Glu Glu Glu Val Lys His Leu Gly Tyr Ala Ser His Leu Met Glu
            355                 360                 365

ATT TTT TGT GAC TCT GAA GAA AAC ACG GAA GGT ACT TCT TTC ACC CAG     1152
Ile Phe Cys Asp Ser Glu Glu Asn Thr Glu Gly Thr Ser Phe Thr Gln
370                 375                 380

CAA GAG TCC CTC AGC AGA ACA ATA CCC CCG GAT AAA ACA GTC ATT GAA     1200
Gln Glu Ser Leu Ser Arg Thr Ile Pro Pro Asp Lys Thr Val Ile Glu
385                 390                 395                 400

TAT GAA TAT GAT GTC AGA ACC ACT GAC ATT TGT GCG GGG CCT GAA GAG     1248
Tyr Glu Tyr Asp Val Arg Thr Thr Asp Ile Cys Ala Gly Pro Glu Glu
            405                 410                 415

CAG GAG CTC AGT TTG CAG GAG GAG GTG TCC ACA CAA GGA ACA TTA TTG     1296
Gln Glu Leu Ser Leu Gln Glu Glu Val Ser Thr Gln Gly Thr Leu Leu
            420                 425                 430

GAG TCG CAG GCA GCG TTG GCA GTC TTG GGC CCG CAA ACG TTA CAG TAT     1344
Glu Ser Gln Ala Ala Leu Ala Val Leu Gly Pro Gln Thr Leu Gln Tyr
            435                 440                 445

TCA TAT ACC CCT CAG CTC CAA GAC TTA GAC CCC CTG GCG CAG GAG CAC     1392
Ser Tyr Thr Pro Gln Leu Gln Asp Leu Asp Pro Leu Ala Gln Glu His
            450                 455                 460

ACA GAC TCG GAG GAG GGG CCG GAG GAA GAG CCA TCG ACG ACC CTG GTC     1440
Thr Asp Ser Glu Glu Gly Pro Glu Glu Glu Pro Ser Thr Thr Leu Val
465                 470                 475                 480
```

```
GAC TGG GAT CCC CAA ACT GGC AGG CTG TGT ATT CCT TCG CTG TCC AGC    1488
Asp Trp Asp Pro Gln Thr Gly Arg Leu Cys Ile Pro Ser Leu Ser Ser
            485                 490                 495

TTC GAC CAG GAT TCA GAG GGC TGC GAG CCT TCT GAG GGG GAT GGG CTC    1536
Phe Asp Gln Asp Ser Glu Gly Cys Glu Pro Ser Glu Gly Asp Gly Leu
        500                 505                 510

GGA GAG GAG GGT CTT CTA TCT AGA CTC TAT GAG GAG CCG GCT CCA GAC    1584
Gly Glu Glu Gly Leu Leu Ser Arg Leu Tyr Glu Glu Pro Ala Pro Asp
        515                 520                 525

AGG CCA CCA GGA GAA AAT GAA ACC TAT CTC ATG CAA TTC ATG GAG GAA    1632
Arg Pro Pro Gly Glu Asn Glu Thr Tyr Leu Met Gln Phe Met Glu Glu
    530                 535                 540

TGG GGG TTA TAT GTG CAG ATG GAA AAC                                1659
Trp Gly Leu Tyr Val Gln Met Glu Asn
545                 550
```

(2) INFORMATION FOR SEQ ID NO:46:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:46:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
                20                  25                  30

Val Ser Gly Gly Leu Pro Lys Pro Ala Asn Ile Thr Phe Leu Ser Ile
            35                  40                  45

Asn Met Lys Asn Val Leu Gln Trp Thr Pro Glu Gly Leu Gln Gly
        50                  55                  60

Val Lys Val Thr Tyr Thr Val Gln Tyr Phe Ile Tyr Gly Gln Lys Lys
65                  70                  75                  80

Trp Leu Asn Lys Ser Glu Cys Arg Asn Ile Asn Arg Thr Tyr Cys Asp
                85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
    210                 215                 220

Pro Pro Arg Arg Ala Gln Pro Ser Glu Lys Gln Cys Ala Arg Thr Leu
225                 230                 235                 240
```

-continued

```
Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
                260                 265                 270

Ile Tyr Arg Tyr Ile His Val Gly Lys Glu Lys His Pro Ala Asn Leu
                275                 280                 285

Ile Leu Ile Tyr Gly Asn Glu Phe Asp Lys Arg Phe Phe Val Pro Ala
                290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
                340                 345                 350

Glu Glu Glu Glu Val Lys His Leu Gly Tyr Ala Ser His Leu Met Glu
                355                 360                 365

Ile Phe Cys Asp Ser Glu Glu Asn Thr Glu Gly Thr Ser Phe Thr Gln
                370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Val Ser Thr Gln Gly Thr Leu Leu
                420                 425                 430

Glu Ser Gln Ala Ala Leu Ala Val Leu Gly Pro Gln Thr Leu Gln Tyr
                435                 440                 445

Ser Tyr Thr Pro Gln Leu Gln Asp Leu Asp Pro Leu Ala Gln Glu His
450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Glu Pro Ala Pro Asp
                515                 520                 525

Arg Pro Pro Gly Glu Asn Glu Thr Tyr Leu Met Gln Phe Met Glu Glu
530                 535                 540

Trp Gly Leu Tyr Val Gln Met Glu Asn
545                 550
```

(2) INFORMATION FOR SEQ ID NO:47:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1659
        (D) OTHER INFORMATION:

(xi) SEQUENCE DESCRIPTION: SEQ ID NO:47:

```
ATG CGG GCT CCC GGC CGC CCG GCC CTG CGG CCG CTG CCG CTG CCG CCG         48
Met Arg Ala Pro Gly Arg Pro Ala Leu Arg Pro Leu Pro Leu Pro Pro
 1               5                  10                  15

CTG CTG CTG TTG CTC CTG GCG GCG CCT TGG GGG CGG GCG GTT CCC TGT         96
Leu Leu Leu Leu Leu Leu Ala Ala Pro Trp Gly Arg Ala Val Pro Cys
            20                  25                  30

GTC TCT GGT GGT TTG CCT AAG CCT GCG AAT ATC ACC TTT CTA TCC ATC        144
Val Ser Gly Gly Leu Pro Lys Pro Ala Asn Ile Thr Phe Leu Ser Ile
        35                  40                  45

AAT ATG AAG AAT GTC CTA CAG TGG ACT CCG CCG GAG GGT CTT CAG GGG        192
Asn Met Lys Asn Val Leu Gln Trp Thr Pro Pro Glu Gly Leu Gln Gly
    50                  55                  60

GTT AAG GTT ACT TAT ACT GTG CAG TAT TTT ATT TAT GGG CAG AAG AAG        240
Val Lys Val Thr Tyr Thr Val Gln Tyr Phe Ile Tyr Gly Gln Lys Lys
65                  70                  75                  80

TGG CTG AAT AAG TCA GAG TGT CGA AAT ATC AAT CGA ACC TAT TGT GAT        288
Trp Leu Asn Lys Ser Glu Cys Arg Asn Ile Asn Arg Thr Tyr Cys Asp
                85                  90                  95

CTT TCT GCT GAG ACT TCT GAT TAT GAG CAT CAG TAT TAT GCC AAG GTT        336
Leu Ser Ala Glu Thr Ser Asp Tyr Glu His Gln Tyr Tyr Ala Lys Val
            100                 105                 110

AAG GCC ATT TGG GGG ACG AAG TGT TCC AAG TGG GCT GAG AGT GGG CGG        384
Lys Ala Ile Trp Gly Thr Lys Cys Ser Lys Trp Ala Glu Ser Gly Arg
        115                 120                 125

TTT TAT CCT TTT CTA GAG ACG CAG ATT GGC CCG CCG GAG GTG GCG CTG        432
Phe Tyr Pro Phe Leu Glu Thr Gln Ile Gly Pro Pro Glu Val Ala Leu
    130                 135                 140

ACT ACG GAT GAG AAG TCC ATT TCT GTT GTC CTG ACG GCT CCG GAG AAG        480
Thr Thr Asp Glu Lys Ser Ile Ser Val Val Leu Thr Ala Pro Glu Lys
145                 150                 155                 160

TGG AAG CGA AAT CCG GAG GAT CTT CCT GTT TCC ATG CAG CAG ATT TAT        528
Trp Lys Arg Asn Pro Glu Asp Leu Pro Val Ser Met Gln Gln Ile Tyr
                165                 170                 175

TCC AAT CTG AAG TAT AAT GTG TCT GTG TTG AAT ACT AAG TCA AAT CGA        576
Ser Asn Leu Lys Tyr Asn Val Ser Val Leu Asn Thr Lys Ser Asn Arg
            180                 185                 190

ACG TGG TCC CAG TGT GTG ACC AAT CAT ACG CTG GTG CTC ACC TGG CTG        624
Thr Trp Ser Gln Cys Val Thr Asn His Thr Leu Val Leu Thr Trp Leu
        195                 200                 205

GAG CCG AAT ACT CTT TAT TGT GTG CAT GTG GAG TCC TTT GTC CCG GGG        672
Glu Pro Asn Thr Leu Tyr Cys Val His Val Glu Ser Phe Val Pro Gly
    210                 215                 220

CCC CCT CGC CGT GCT CAG CCT TCT GAG AAG CAG TGT GCC AGG ACT TTG        720
Pro Pro Arg Arg Ala Gln Pro Ser Glu Lys Gln Cys Ala Arg Thr Leu
225                 230                 235                 240

AAG GAT CAG TCA TCA GAG TTT AAG GCT AAG ATC ATC TTT TGG TAT GTT        768
Lys Asp Gln Ser Ser Glu Phe Lys Ala Lys Ile Ile Phe Trp Tyr Val
                245                 250                 255

TTG CCC ATT TCT ATT ACC GTG TTT CTT TTT TCT GTG ATG GGC TAT TCC        816
Leu Pro Ile Ser Ile Thr Val Phe Leu Phe Ser Val Met Gly Tyr Ser
            260                 265                 270

ATC TAT CGA TAT ATC CAT GTT GGC AAG GAG AAG CAT CCG GCG AAT TTG        864
Ile Tyr Arg Tyr Ile His Val Gly Lys Glu Lys His Pro Ala Asn Leu
        275                 280                 285

ATT TTG ATT TAT GGG AAT GAG TTT GAT AAG CGA TTT TTT GTG CCT GCT        912
Ile Leu Ile Tyr Gly Asn Glu Phe Asp Lys Arg Phe Phe Val Pro Ala
    290                 295                 300

GAG AAG ATC GTG ATT AAT TTT ATC ACC CTC AAT ATC TCG GAT GAT TCT        960
Glu Lys Ile Val Ile Asn Phe Ile Thr Leu Asn Ile Ser Asp Asp Ser
305                 310                 315                 320
```

```
AAG ATT TCT CAT CAG GAT ATG AGT CTA CTG GGG AAG TCA AGT GAT GTG      1008
Lys Ile Ser His Gln Asp Met Ser Leu Leu Gly Lys Ser Ser Asp Val
            325                 330                 335

TCC TCA CTT AAT GAT CCT CAG CCC TCA GGG AAT CTG AGG CCC CCT CAG      1056
Ser Ser Leu Asn Asp Pro Gln Pro Ser Gly Asn Leu Arg Pro Pro Gln
            340                 345                 350

GAG GAG GAG GAG GTG AAG CAT CTA GGG TAT GCT TCG CAT TTG ATG GAG      1104
Glu Glu Glu Glu Val Lys His Leu Gly Tyr Ala Ser His Leu Met Glu
            355                 360                 365

ATT TTT TGT GAT TCT GAG GAG AAT ACG GAG GGT ACT TCT TTT ACC CAG      1152
Ile Phe Cys Asp Ser Glu Glu Asn Thr Glu Gly Thr Ser Phe Thr Gln
        370                 375                 380

CAG GAG TCC CTC TCA CGA ACG ATT CCC CCG GAT AAG ACG GTC ATT GAG      1200
Gln Glu Ser Leu Ser Arg Thr Ile Pro Pro Asp Lys Thr Val Ile Glu
385                 390                 395                 400

TAT GAG TAT GAT GTC CGA ACC ACT GAT ATT TGT GCG GGG CCT GAG GAG      1248
Tyr Glu Tyr Asp Val Arg Thr Thr Asp Ile Cys Ala Gly Pro Glu Glu
                405                 410                 415

CAG GAG CTC AGT TTG CAG GAG GAG GTG TCC ACG CAG GGG ACG CTA TTG      1296
Gln Glu Leu Ser Leu Gln Glu Glu Val Ser Thr Gln Gly Thr Leu Leu
            420                 425                 430

GAG TCG CAG GCG GCG TTG GCG GTC TTG GGC CCG CAG ACG CTA CAG TAT      1344
Glu Ser Gln Ala Ala Leu Ala Val Leu Gly Pro Gln Thr Leu Gln Tyr
            435                 440                 445

TCA TAT ACC CCT CAG CTC CAG GAT CTA GAT CCC CTG GCG CAG GAG CAT      1392
Ser Tyr Thr Pro Gln Leu Gln Asp Leu Asp Pro Leu Ala Gln Glu His
            450                 455                 460

ACG GAT TCG GAG GAG GGG CCG GAG GAG GAG CCG TCG ACG ACC CTG GTC      1440
Thr Asp Ser Glu Glu Gly Pro Glu Glu Glu Pro Ser Thr Thr Leu Val
465                 470                 475                 480

GAT TGG GAT CCC CAG ACT GGC AGG CTG TGT ATT CCT TCG CTG TCC TCA      1488
Asp Trp Asp Pro Gln Thr Gly Arg Leu Cys Ile Pro Ser Leu Ser Ser
            485                 490                 495

TTT GAT CAG GAT TCA GAG GGC TGT GAG CCT TCT GAG GGG GAT GGG CTC      1536
Phe Asp Gln Asp Ser Glu Gly Cys Glu Pro Ser Glu Gly Asp Gly Leu
            500                 505                 510

GGG GAG GAG GGT CTT CTA TCT CGA CTC TAT GAG GAG CCG GCT CCG GAT      1584
Gly Glu Glu Gly Leu Leu Ser Arg Leu Tyr Glu Glu Pro Ala Pro Asp
            515                 520                 525

AGG CCG CCG GGG GAG AAT GAG ACC TAT CTC ATG CAG TTT ATG GAG GAG      1632
Arg Pro Pro Gly Glu Asn Glu Thr Tyr Leu Met Gln Phe Met Glu Glu
            530                 535                 540

TGG GGG CTA TAT GTG CAG ATG GAG AAT                                  1659
Trp Gly Leu Tyr Val Gln Met Glu Asn
545                 550
```

(2) INFORMATION FOR SEQ ID NO:48:

(i) SEQUENCE CHARACTERISTICS:
        (A) LENGTH: 553 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:48:

```
Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30
```

```
Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
     50                  55                  60

Val Lys Val Thr Tyr Thr Val Gln Tyr Phe Ile Tyr Gly Gln Lys Lys
 65              70                  75                      80

Trp Leu Asn Lys Ser Glu Cys Arg Asn Ile Asn Arg Thr Tyr Cys Asp
             85                  90                  95

Leu Ser Ala Glu Thr Ser Asp Tyr Glu His Gln Tyr Tyr Ala Lys Val
             100                 105                 110

Lys Ala Ile Trp Gly Thr Lys Cys Ser Lys Trp Ala Glu Ser Gly Arg
             115                 120                 125

Phe Tyr Pro Phe Leu Glu Thr Gln Ile Gly Pro Pro Glu Val Ala Leu
             130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                 165                 170                 175

Ser Asn Leu Lys Tyr Asn Val Ser Val Leu Asn Thr Lys Ser Asn Arg
             180                 185                 190

Thr Trp Ser Gln Cys Val Thr Asn His Thr Leu Val Leu Thr Trp Leu
             195                 200                 205

Glu Pro Asn Thr Leu Tyr Cys Val His Val Glu Ser Phe Val Pro Gly
             210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                 245                 250                 255

Leu Pro Ile Ser Ile Thr Val Phe Leu Phe Ser Val Met Gly Tyr Ser
             260                 265                 270

Ile Tyr Arg Tyr Ile His Val Gly Lys Glu Lys His Pro Ala Asn Leu
             275                 280                 285

Ile Leu Ile Tyr Gly Asn Glu Phe Asp Lys Arg Phe Phe Val Pro Ala
             290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                 325                 330                 335

Ser Ser Leu Asn Asp Pro Gln Pro Ser Gly Asn Leu Arg Pro Pro Gln
             340                 345                 350

Glu Glu Glu Glu Val Lys His Leu Gly Tyr Ala Ser His Leu Met Glu
             355                 360                 365

Ile Phe Cys Asp Ser Glu Glu Asn Thr Glu Gly Thr Ser Phe Thr Gln
             370                 375                 380

Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                 405                 410                 415

Gln Glu Leu Ser Leu Gln Glu Glu Val Ser Thr Gln Gly Thr Leu Leu
             420                 425                 430

Glu Ser Gln Ala Ala Leu Ala Val Leu Gly Pro Gln Thr Leu Gln Tyr
             435                 440                 445
```

```
Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
                500                 505                 510

Gly Glu Glu Gly Leu Leu Ser Arg Leu Tyr Glu Glu Pro Ala Pro Asp
            515                 520                 525

Arg Pro Pro Gly Glu Asn Glu Thr Tyr Leu Met Gln Phe Met Glu Glu
            530                 535                 540

Trp Gly Leu Tyr Val Gln Met Glu Asn
545                 550
```

(2) INFORMATION FOR SEQ ID NO:49:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...663
        (D) OTHER INFORMATION:

(xi) SEQUENCE DESCRIPTION: SEQ ID NO:49:

```
GTT CCC TGT GTC TCT GGT GGT TTG CCT AAA CCT GCA AAC ATC ACC TTC    48
Val Pro Cys Val Ser Gly Gly Leu Pro Lys Pro Ala Asn Ile Thr Phe
1               5                   10                  15

TTA TCC ATC AAC ATG AAG AAT GTC CTA CAA TGG ACT CCA CCA GAG GGT    96
Leu Ser Ile Asn Met Lys Asn Val Leu Gln Trp Thr Pro Pro Glu Gly
                20                  25                  30

CTT CAA GGA GTT AAA GTT ACT TAC ACT GTG CAG TAT TTC ATA TAT GGG   144
Leu Gln Gly Val Lys Val Thr Tyr Thr Val Gln Tyr Phe Ile Tyr Gly
            35                  40                  45

CAA AAG AAA TGG CTG AAT AAA TCA GAA TGC AGA AAT ATC AAT AGA ACC   192
Gln Lys Lys Trp Leu Asn Lys Ser Glu Cys Arg Asn Ile Asn Arg Thr
50                  55                  60

TAC TGT GAT CTT TCT GCT GAA ACT TCT GAC TAC GAA CAC CAG TAT TAT   240
Tyr Cys Asp Leu Ser Ala Glu Thr Ser Asp Tyr Glu His Gln Tyr Tyr
65                  70                  75                  80

GCC AAA GTT AAG GCC ATT TGG GGA ACA AAG TGT TCC AAA TGG GCT GAA   288
Ala Lys Val Lys Ala Ile Trp Gly Thr Lys Cys Ser Lys Trp Ala Glu
                85                  90                  95

AGT GGA CGG TTC TAT CCT TTT TTA GAA ACA CAA ATT GGC CCA CCA GAG   336
Ser Gly Arg Phe Tyr Pro Phe Leu Glu Thr Gln Ile Gly Pro Pro Glu
            100                 105                 110

GTG GCA CTG ACT ACA GAT GAG AAG TCC ATT TCT GTT GTC CTG ACA GCT   384
Val Ala Leu Thr Thr Asp Glu Lys Ser Ile Ser Val Val Leu Thr Ala
        115                 120                 125

CCA GAG AAG TGG AAG AGA AAT CCA GAA GAC CTT CCT GTT TCC ATG CAA   432
Pro Glu Lys Trp Lys Arg Asn Pro Glu Asp Leu Pro Val Ser Met Gln
130                 135                 140

CAA ATA TAC TCC AAT CTG AAG TAT AAC GTG TCT GTG TTG AAT ACT AAA   480
Gln Ile Tyr Ser Asn Leu Lys Tyr Asn Val Ser Val Leu Asn Thr Lys
145                 150                 155                 160
```

| | | |
|---|---|---|
| TCA AAC AGA ACG TGG TCC CAG TGT GTG ACC AAC CAC ACG CTG GTG CTC | | 528 |
| Ser Asn Arg Thr Trp Ser Gln Cys Val Thr Asn His Thr Leu Val Leu | | |
|               165                    170                  175 | | |
| ACC TGG CTG GAG CCG AAC ACT CTT TAC TGC GTA CAC GTG GAG TCC TTC | | 576 |
| Thr Trp Leu Glu Pro Asn Thr Leu Tyr Cys Val His Val Glu Ser Phe | | |
|     180                    185                    190 | | |
| GTC CCA GGG CCC CCT CGC CGT GCT CAG CCT TCT GAG AAG CAG TGT GCC | | 624 |
| Val Pro Gly Pro Pro Arg Arg Ala Gln Pro Ser Glu Lys Gln Cys Ala | | |
|         195                    200                  205 | | |
| AGG ACT TTG AAA GAT CAA TCA TCA GAG TTC AAG GCT AAA | | 663 |
| Arg Thr Leu Lys Asp Gln Ser Ser Glu Phe Lys Ala Lys | | |
|   210                    215                    220 | | |

(2) INFORMATION FOR SEQ ID NO:50:

(i) SEQUENCE CHARACTERISTICS:
        (A) LENGTH: 221 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:50:

```
Val Pro Cys Val Ser Gly Gly Leu Pro Lys Pro Ala Asn Ile Thr Phe
 1               5                  10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
        35                  40                  45

Gln Lys Lys Trp Leu Asn Lys Ser Glu Cys Arg Asn Ile Asn Arg Thr
 50                  55                  60

Tyr Cys Asp Leu Ser Ala Glu Thr Ser Asp Tyr Glu His Gln Tyr Tyr
 65                  70                  75                  80

Ala Lys Val Lys Ala Ile Trp Gly Thr Lys Cys Ser Lys Trp Ala Glu
            85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125

Pro Glu Lys Trp Lys Arg Asn Pro Glu Asp Leu Pro Val Ser Met Gln
130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
            165                 170                 175

Thr Trp Leu Glu Pro Asn Thr Leu Tyr Cys Val His Val Glu Ser Phe
        180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Phe Lys Ala Lys
    210                 215                 220
```

(2) INFORMATION FOR SEQ ID NO:51:

(i) SEQUENCE CHARACTERISTICS:
        (A) LENGTH: 663 base pairs
        (B) TYPE: nucleic acid
        (C) STRANDEDNESS: single (D) TOPOLOGY: linear (ii) MOLECULE TYPE: cDNA (ix) FEATURE:
         (A) NAME/KEY: Coding Sequence
         (B) LOCATION: 1...663
         (D) OTHER INFORMATION:

(xi) SEQUENCE DESCRIPTION: SEQ ID NO:51:

```
GTT CCC TGT GTC TCT GGT GGT TTG CCT AAA CCT GGA AAC ATC ACC TTC      48
Val Pro Cys Val Ser Gly Gly Leu Pro Lys Pro Gly Asn Ile Thr Phe
 1               5                  10                  15

TTA TCC ATC AAC ATG AAG AAT GTC CTA CAA TGG ACT CCA CCA GAG GGT      96
Leu Ser Ile Asn Met Lys Asn Val Leu Gln Trp Thr Pro Pro Glu Gly
             20                  25                  30

CTT CAA GGA GTT AAA GTT ACT TAC ACT GTG CAG TAT TTC ATA TAT GGG     144
Leu Gln Gly Val Lys Val Thr Tyr Thr Val Gln Tyr Phe Ile Tyr Gly
         35                  40                  45

CAA AAG AAA TGG CTG AAT AAA TCA GAA TGC AGA AAT ATC AAT AGA ACC     192
Gln Lys Lys Trp Leu Asn Lys Ser Glu Cys Arg Asn Ile Asn Arg Thr
     50                  55                  60

TAC TGT GAT CTT TCT GCT GAA ACT TCT GAC TAC GAA CAC CAG TAT TAT     240
Tyr Cys Asp Leu Ser Ala Glu Thr Ser Asp Tyr Glu His Gln Tyr Tyr
 65                  70                  75                  80

GCC AAA GTT AAG GCC ATT TGG GGA ACA AAG TGT TCC AAA TGG GCT GAA     288
Ala Lys Val Lys Ala Ile Trp Gly Thr Lys Cys Ser Lys Trp Ala Glu
                 85                  90                  95

AGT GGA CGG TTC TAT CCT TTT TTA GAA ACA CAA ATT GGC CCA CCA GAG     336
Ser Gly Arg Phe Tyr Pro Phe Leu Glu Thr Gln Ile Gly Pro Pro Glu
            100                 105                 110

GTG GGA CTG ACT ACA GAT GAG AAG TCC ATT TCT GTT GTC CTG ACA GCT     384
Val Gly Leu Thr Thr Asp Glu Lys Ser Ile Ser Val Val Leu Thr Ala
        115                 120                 125

CCA GAG AAG TGG AAG AGA AAT CCA GAA GAC CTT CCT GTT TCC ATG CAA     432
Pro Glu Lys Trp Lys Arg Asn Pro Glu Asp Leu Pro Val Ser Met Gln
    130                 135                 140

CAA ATA TAC TCC AAT CTG AAG TAT AAC GTG TCT GTG TTG AAT ACT AAA     480
Gln Ile Tyr Ser Asn Leu Lys Tyr Asn Val Ser Val Leu Asn Thr Lys
145                 150                 155                 160

TCA AAC AGA ACG TGG TCC CAG TGT GTG ACC AAC CAC ACG CTG GTG CTC     528
Ser Asn Arg Thr Trp Ser Gln Cys Val Thr Asn His Thr Leu Val Leu
                165                 170                 175

ACC TGG CTG GAG CCG AAC ACT CTT TAC TGC GTA CAC GTG GAG TCC TTC     576
Thr Trp Leu Glu Pro Asn Thr Leu Tyr Cys Val His Val Glu Ser Phe
            180                 185                 190

GTC CCA GGG CCC CCT CGC CGT GCT CAG CCT TCT GAG AAG CAG TGT GCC     624
Val Pro Gly Pro Pro Arg Arg Ala Gln Pro Ser Glu Lys Gln Cys Ala
        195                 200                 205

AGG ACT TTG AAA GAT CAA TCA TCA GAG TTC AAG GCT AAA                 663
Arg Thr Leu Lys Asp Gln Ser Ser Glu Phe Lys Ala Lys
    210                 215                 220
```

(2) INFORMATION FOR SEQ ID NO:52:

(i) SEQUENCE CHARACTERISTICS:
        (A) LENGTH: 221 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:52:

```
Val Pro Cys Val Ser Gly Gly Leu Pro Lys Pro Gly Asn Ile Thr Phe
 1               5                  10                  15

Leu Ser Ile Asn Met Lys Asn Val Leu Gln Trp Thr Pro Pro Glu Gly
             20                  25                  30

Leu Gln Gly Val Lys Val Thr Tyr Thr Val Gln Tyr Phe Ile Tyr Gly
         35                  40                  45

Gln Lys Lys Trp Leu Asn Lys Ser Glu Cys Arg Asn Ile Asn Arg Thr
 50                  55                  60

Tyr Cys Asp Leu Ser Ala Glu Thr Ser Asp Tyr Glu His Gln Tyr Tyr
 65                  70                  75                  80

Ala Lys Val Lys Ala Ile Trp Gly Thr Lys Cys Ser Lys Trp Ala Glu
             85                  90                  95

Ser Gly Arg Phe Tyr Pro Phe Leu Glu Thr Gln Ile Gly Pro Pro Glu
            100                 105                 110

Val Gly Leu Thr Thr Asp Glu Lys Ser Ile Ser Val Val Leu Thr Ala
            115                 120                 125

Pro Glu Lys Trp Lys Arg Asn Pro Glu Asp Leu Pro Val Ser Met Gln
        130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Phe Lys Ala Lys
210                 215                 220
```

(2) INFORMATION FOR SEQ ID NO:53:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...663
        (D) OTHER INFORMATION:

(xi) SEQUENCE DESCRIPTION: SEQ ID NO:53:

```
GTT CCC TGT GTC TCT GGT GGT TTG CCT AAA CCT GCA AAC ATC ACC TTC    48
Val Pro Cys Val Ser Gly Gly Leu Pro Lys Pro Ala Asn Ile Thr Phe
 1               5                  10                  15

TTA TCC ATC AAC ATG AAG AAT GTC CTA CAA TGG ACT CCA CCA GAG GGT    96
Leu Ser Ile Asn Met Lys Asn Val Leu Gln Trp Thr Pro Pro Glu Gly
             20                  25                  30

CTT CAA GGA GTT AAA GTT ACT TAC ACT GTG CAG TAT TTC TTA TAT GGG   144
Leu Gln Gly Val Lys Val Thr Tyr Thr Val Gln Tyr Phe Leu Tyr Gly
         35                  40                  45

CAA AAG AAA TGG CTG AAT AAA TCA GAA TGC AGA AAT ATC AAT AGA ACC   192
Gln Lys Lys Trp Leu Asn Lys Ser Glu Cys Arg Asn Ile Asn Arg Thr
 50                  55                  60
```

```
TAC TGT GAT CTT TCT GCT GAA ACT TCT GAC TAC GAA CAC CAG TAT TAT         240
Tyr Cys Asp Leu Ser Ala Glu Thr Ser Asp Tyr Glu His Gln Tyr Tyr
 65                  70                  75                  80

GCC AAA GTT AAG GCC ATT TGG GGA ACA AAG TGT TCC AAA TGG GCT GAA         288
Ala Lys Val Lys Ala Ile Trp Gly Thr Lys Cys Ser Lys Trp Ala Glu
                 85                  90                  95

AGT GGA CGG TTC TAT CCT TTT TTA GAA ACA CAA ATT GGC CCA CCA GAG         336
Ser Gly Arg Phe Tyr Pro Phe Leu Glu Thr Gln Ile Gly Pro Pro Glu
            100                 105                 110

GTG GCA CTG ACT ACA GAT GAG AAG TCC ATT TCT GTT GTC CTG ACA GCT         384
Val Ala Leu Thr Thr Asp Glu Lys Ser Ile Ser Val Val Leu Thr Ala
        115                 120                 125

CCA GAG AAG TGG AAG AGA AAT CCA GAA GAC CTT CCT GTT TCC ATG CAA         432
Pro Glu Lys Trp Lys Arg Asn Pro Glu Asp Leu Pro Val Ser Met Gln
    130                 135                 140

CAA TTA TAC TCC AAT CTG AAG TAT AAC GTG TCT GTG TTG AAT ACT AAA         480
Gln Leu Tyr Ser Asn Leu Lys Tyr Asn Val Ser Val Leu Asn Thr Lys
145                 150                 155                 160

TCA AAC AGA ACG TGG TCC CAG TGT GTG ACC AAC CAC ACG CTG GTG CTC         528
Ser Asn Arg Thr Trp Ser Gln Cys Val Thr Asn His Thr Leu Val Leu
                165                 170                 175

ACC TGG CTG GAG CCG AAC ACT CTT TAC TGC GTA CAC GTG GAG TCC TTC         576
Thr Trp Leu Glu Pro Asn Thr Leu Tyr Cys Val His Val Glu Ser Phe
            180                 185                 190

GTC CCA GGG CCC CCT CGC CGT GCT CAG CCT TCT GAG AAG CAG TGT GCC         624
Val Pro Gly Pro Pro Arg Arg Ala Gln Pro Ser Glu Lys Gln Cys Ala
        195                 200                 205

AGG ACT TTG AAA GAT CAA TCA TCA GAG TTC AAG GCT AAA                     663
Arg Thr Leu Lys Asp Gln Ser Ser Glu Phe Lys Ala Lys
    210                 215                 220

(2) INFORMATION FOR SEQ ID NO:54:

(i) SEQUENCE CHARACTERISTICS:
        (A) LENGTH: 221 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:54:

Val Pro Cys Val Ser Gly Gly Leu Pro Lys Pro Ala Asn Ile Thr Phe
 1               5                  10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Leu Tyr Gly
        35                  40                  45

Gln Lys Lys Trp Leu Asn Lys Ser Glu Cys Arg Asn Ile Asn Arg Thr
 50                  55                  60

Tyr Cys Asp Leu Ser Ala Glu Thr Ser Asp Tyr Glu His Gln Tyr Tyr
 65                  70                  75                  80

Ala Lys Val Lys Ala Ile Trp Gly Thr Lys Cys Ser Lys Trp Ala Glu
                 85                  90                  95

Ser Gly Arg Phe Tyr Pro Phe Leu Glu Thr Gln Ile Gly Pro Pro Glu
            100                 105                 110

Val Ala Leu Thr Thr Asp Glu Lys Ser Ile Ser Val Val Leu Thr Ala
        115                 120                 125
```

| | | | | | | | | | | | | |
|---|---|---|---|---|---|---|---|---|---|---|---|---|
|Pro|Glu|Lys|Trp|Lys|Arg|Asn|Pro|Glu|Asp|Leu|Pro|Val|Ser|Met|Gln|
| |130| | | |135| | | |140| | | |

Gln Leu Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
            165                 170                 175

Thr Trp Leu Glu Pro Asn Thr Leu Tyr Cys Val His Val Glu Ser Phe
        180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Phe Lys Ala Lys
    210                 215                 220

(2) INFORMATION FOR SEQ ID NO:55:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...663
        (D) OTHER INFORMATION:

(xi) SEQUENCE DESCRIPTION: SEQ ID NO:55:

```
GTT CCC TGT GTC TCT GGT GGT TTG CCT AAA CCT GCA AAC ATC ACC TTC     48
Val Pro Cys Val Ser Gly Gly Leu Pro Lys Pro Ala Asn Ile Thr Phe
 1               5                  10                  15

TTA TCC ATC AAC ATG AAG AAT GTC CTA CAA TGG ACT CCA CCA GAG GGT     96
Leu Ser Ile Asn Met Lys Asn Val Leu Gln Trp Thr Pro Pro Glu Gly
            20                  25                  30

CTT CAA GGA GTT AAA GTT ACT TAC ACT GTG CAG TAT TTC ATA TAT GGG    144
Leu Gln Gly Val Lys Val Thr Tyr Thr Val Gln Tyr Phe Ile Tyr Gly
        35                  40                  45

CAA AAG AAA TGG CTG AAT AAA TCA GAA TGC AGA AAT ATC AAT AGA ACC    192
Gln Lys Lys Trp Leu Asn Lys Ser Glu Cys Arg Asn Ile Asn Arg Thr
    50                  55                  60

TAC TGT GAT CTT TCT GCT GAA ACT TCT GAC TAC GAA CAC CAG TAT TAT    240
Tyr Cys Asp Leu Ser Ala Glu Thr Ser Asp Tyr Glu His Gln Tyr Tyr
 65                 70                  75                  80

GCC AAA GTT AAG GCC ATT TGG GGA AGC AAG TGT TCC AAA TGG GCT GAA    288
Ala Lys Val Lys Ala Ile Trp Gly Ser Lys Cys Ser Lys Trp Ala Glu
                85                  90                  95

AGT GGA CGG TTC TAT CCT TTT TTA GAA AGC CAA ATT GGC CCA CCA GAG    336
Ser Gly Arg Phe Tyr Pro Phe Leu Glu Ser Gln Ile Gly Pro Pro Glu
            100                 105                 110

GTG GCA CTG ACT AGC GAT GAG AAG TCC ATT TCT GTT GTC CTG AGC GCT    384
Val Ala Leu Thr Ser Asp Glu Lys Ser Ile Ser Val Val Leu Ser Ala
        115                 120                 125

CCA GAG AAG TGG AAG AGA AAT CCA GAA GAC CTT CCT GTT TCC ATG CAA    432
Pro Glu Lys Trp Lys Arg Asn Pro Glu Asp Leu Pro Val Ser Met Gln
    130                 135                 140

CAA ATA TAC TCC AAT CTG AAG TAT AAC GTG TCT GTG TTG AAT ACT AAA    480
Gln Ile Tyr Ser Asn Leu Lys Tyr Asn Val Ser Val Leu Asn Thr Lys
145                 150                 155                 160

TCA AAC AGA ACG TGG TCC CAG TGT GTG ACC AAC CAC ACG CTG GTG CTC    528
Ser Asn Arg Thr Trp Ser Gln Cys Val Thr Asn His Thr Leu Val Leu
            165                 170                 175
```

```
ACC TGG CTG GAG CCG AAC ACT CTT TAC TGC GTA CAC GTG GAG TCC TTC       576
Thr Trp Leu Glu Pro Asn Thr Leu Tyr Cys Val His Val Glu Ser Phe
        180                 185                 190

GTC CCA GGG CCC CCT CGC CGT GCT CAG CCT TCT GAG AAG CAG TGT GCC       624
Val Pro Gly Pro Pro Arg Arg Ala Gln Pro Ser Glu Lys Gln Cys Ala
            195                 200                 205

AGG ACT TTG AAA GAT CAA TCA TCA GAG TTC AAG GCT AAA                    663
Arg Thr Leu Lys Asp Gln Ser Ser Glu Phe Lys Ala Lys
        210                 215                 220
```

(2) INFORMATION FOR SEQ ID NO:56:

(i) SEQUENCE CHARACTERISTICS:
        (A) LENGTH: 221 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:56:

```
Val Pro Cys Val Ser Gly Gly Leu Pro Lys Pro Ala Asn Ile Thr Phe
 1               5                  10                  15

Leu Ser Ile Asn Met Lys Asn Val Leu Gln Trp Thr Pro Pro Glu Gly
            20                  25                  30

Leu Gln Gly Val Lys Val Thr Tyr Thr Val Gln Tyr Phe Ile Tyr Gly
        35                  40                  45

Gln Lys Lys Trp Leu Asn Lys Ser Glu Cys Arg Asn Ile Asn Arg Thr
 50                  55                  60

Tyr Cys Asp Leu Ser Ala Glu Thr Ser Asp Tyr Glu His Gln Tyr Tyr
 65                  70                  75                  80

Ala Lys Val Lys Ala Ile Trp Gly Ser Lys Cys Ser Lys Trp Ala Glu
                85                  90                  95

Ser Gly Arg Phe Tyr Pro Phe Leu Glu Ser Gln Ile Gly Pro Pro Glu
            100                 105                 110

Val Ala Leu Thr Ser Asp Glu Lys Ser Ile Ser Val Val Leu Ser Ala
        115                 120                 125

Pro Glu Lys Trp Lys Arg Asn Pro Glu Asp Leu Pro Val Ser Met Gln
    130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
        195                 200                 205

Arg Thr Leu Lys Asp Gln Ser Ser Glu Phe Lys Ala Lys
    210                 215                 220
```

(2) INFORMATION FOR SEQ ID NO:57:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA -continued (ix) FEATURE:
    (A) NAME/KEY: Coding Sequence
    (B) LOCATION: 1...663
    (D) OTHER INFORMATION:

(xi) SEQUENCE DESCRIPTION: SEQ ID NO:57:

| | | | | | | | | | | | | | | | | |
|---|---|---|---|---|---|---|---|---|---|---|---|---|---|---|---|---|
| GTT | CCC | TGT | GTC | TCT | GGT | GGT | TTG | CCT | AAA | CCT | GCA | AAC | ATC | ACC | TTC | 48 |
| Val | Pro | Cys | Val | Ser | Gly | Gly | Leu | Pro | Lys | Pro | Ala | Asn | Ile | Thr | Phe | |
| 1 | | | | 5 | | | | | 10 | | | | | 15 | | |

| TTA | TCC | ATC | AAC | ATG | AAG | AAT | GTC | CTA | CAA | TGG | ACT | CCA | CCA | GAG | GGT | 96 |
|---|---|---|---|---|---|---|---|---|---|---|---|---|---|---|---|---|
| Leu | Ser | Ile | Asn | Met | Lys | Asn | Val | Leu | Gln | Trp | Thr | Pro | Pro | Glu | Gly | |
| | | | 20 | | | | | 25 | | | | | 30 | | | |

| CTT | CAA | GGA | GTT | AAA | GTT | ACT | TAC | ACT | GTG | CAG | TAT | TTC | ATA | TAT | GGG | 144 |
|---|---|---|---|---|---|---|---|---|---|---|---|---|---|---|---|---|
| Leu | Gln | Gly | Val | Lys | Val | Thr | Tyr | Thr | Val | Gln | Tyr | Phe | Ile | Tyr | Gly | |
| | | 35 | | | | | 40 | | | | | 45 | | | | |

| CAA | AAG | AAA | TGG | CTG | AAT | AAA | TCA | GAC | TGC | AGA | AAT | ATC | AAT | AGA | ACC | 192 |
|---|---|---|---|---|---|---|---|---|---|---|---|---|---|---|---|---|
| Gln | Lys | Lys | Trp | Leu | Asn | Lys | Ser | Asp | Cys | Arg | Asn | Ile | Asn | Arg | Thr | |
| 50 | | | | | 55 | | | | | 60 | | | | | | |

| TAC | TGT | GAT | CTT | TCT | GCT | GAC | ACT | TCT | GAC | TAC | GAC | CAC | CAG | TAT | TAT | 240 |
|---|---|---|---|---|---|---|---|---|---|---|---|---|---|---|---|---|
| Tyr | Cys | Asp | Leu | Ser | Ala | Asp | Thr | Ser | Asp | Tyr | Asp | His | Gln | Tyr | Tyr | |
| 65 | | | | | 70 | | | | | 75 | | | | | 80 | |

| GCC | AAA | GTT | AAG | GCC | ATT | TGG | GGA | ACA | AAG | TGT | TCC | AAA | TGG | GCT | GAC | 288 |
|---|---|---|---|---|---|---|---|---|---|---|---|---|---|---|---|---|
| Ala | Lys | Val | Lys | Ala | Ile | Trp | Gly | Thr | Lys | Cys | Ser | Lys | Trp | Ala | Asp | |
| | | | | 85 | | | | | 90 | | | | | 95 | | |

| AGT | GGA | CGG | TTC | TAT | CCT | TTT | TTA | GAC | ACA | CAA | ATT | GGC | CCA | CCA | GAG | 336 |
|---|---|---|---|---|---|---|---|---|---|---|---|---|---|---|---|---|
| Ser | Gly | Arg | Phe | Tyr | Pro | Phe | Leu | Asp | Thr | Gln | Ile | Gly | Pro | Pro | Glu | |
| | | | | 100 | | | | | 105 | | | | | 110 | | |

| GTG | GCA | CTG | ACT | ACA | GAT | GAG | AAG | TCC | ATT | TCT | GTT | GTC | CTG | ACA | GCT | 384 |
|---|---|---|---|---|---|---|---|---|---|---|---|---|---|---|---|---|
| Val | Ala | Leu | Thr | Thr | Asp | Glu | Lys | Ser | Ile | Ser | Val | Val | Leu | Thr | Ala | |
| | | | 115 | | | | | 120 | | | | | 125 | | | |

| CCA | GAG | AAG | TGG | AAG | AGA | AAT | CCA | GAC | GAC | CTT | CCT | GTT | TCC | ATG | CAA | 432 |
|---|---|---|---|---|---|---|---|---|---|---|---|---|---|---|---|---|
| Pro | Glu | Lys | Trp | Lys | Arg | Asn | Pro | Asp | Asp | Leu | Pro | Val | Ser | Met | Gln | |
| | 130 | | | | | 135 | | | | | 140 | | | | | |

| CAA | ATA | TAC | TCC | AAT | CTG | AAG | TAT | AAC | GTG | TCT | GTG | TTG | AAT | ACT | AAA | 480 |
|---|---|---|---|---|---|---|---|---|---|---|---|---|---|---|---|---|
| Gln | Ile | Tyr | Ser | Asn | Leu | Lys | Tyr | Asn | Val | Ser | Val | Leu | Asn | Thr | Lys | |
| 145 | | | | | 150 | | | | | 155 | | | | | 160 | |

| TCA | AAC | AGA | ACG | TGG | TCC | CAG | TGT | GTG | ACC | AAC | CAC | ACG | CTG | GTG | CTC | 528 |
|---|---|---|---|---|---|---|---|---|---|---|---|---|---|---|---|---|
| Ser | Asn | Arg | Thr | Trp | Ser | Gln | Cys | Val | Thr | Asn | His | Thr | Leu | Val | Leu | |
| | | | | 165 | | | | | 170 | | | | | 175 | | |

| ACC | TGG | CTG | GAG | CCG | AAC | ACT | CTT | TAC | TGC | GTA | CAC | GTG | GAG | TCC | TTC | 576 |
|---|---|---|---|---|---|---|---|---|---|---|---|---|---|---|---|---|
| Thr | Trp | Leu | Glu | Pro | Asn | Thr | Leu | Tyr | Cys | Val | His | Val | Glu | Ser | Phe | |
| | | | 180 | | | | | 185 | | | | | 190 | | | |

| GTC | CCA | GGG | CCC | CCT | CGC | CGT | GCT | CAG | CCT | TCT | GAG | AAG | CAG | TGT | GCC | 624 |
|---|---|---|---|---|---|---|---|---|---|---|---|---|---|---|---|---|
| Val | Pro | Gly | Pro | Pro | Arg | Arg | Ala | Gln | Pro | Ser | Glu | Lys | Gln | Cys | Ala | |
| | | 195 | | | | | 200 | | | | | 205 | | | | |

| AGG | ACT | TTG | AAA | GAT | CAA | TCA | TCA | GAG | TTC | AAG | GCT | AAA | | | | 663 |
|---|---|---|---|---|---|---|---|---|---|---|---|---|---|---|---|---|
| Arg | Thr | Leu | Lys | Asp | Gln | Ser | Ser | Glu | Phe | Lys | Ala | Lys | | | | |
| | 210 | | | | | 215 | | | | | 220 | | | | | |

(2) INFORMATION FOR SEQ ID NO:58:

(i) SEQUENCE CHARACTERISTICS:
      (A) LENGTH: 221 amino acids
      (B) TYPE: amino acid
      (C) STRANDEDNESS: single
      (D) TOPOLOGY: linear (ii) MOLECULE TYPE: protein (v) FRAGMENT TYPE: internal (xi) SEQUENCE DESCRIPTION: SEQ ID NO:58:

| Val | Pro | Cys | Val | Ser | Gly | Gly | Leu | Pro | Lys | Pro | Ala | Asn | Ile | Thr | Phe |
|---|---|---|---|---|---|---|---|---|---|---|---|---|---|---|---|
| 1 | | | | 5 | | | | | 10 | | | | | 15 | |

```
Leu Ser Ile Asn Met Lys Asn Val Leu Gln Trp Thr Pro Pro Glu Gly
                20                  25                  30

Leu Gln Gly Val Lys Val Thr Tyr Thr Val Gln Tyr Phe Ile Tyr Gly
            35                  40                  45

Gln Lys Lys Trp Leu Asn Lys Ser Asp Cys Arg Asn Ile Asn Arg Thr
 50                  55                  60

Tyr Cys Asp Leu Ser Ala Asp Thr Ser Asp Tyr Asp His Gln Tyr Tyr
 65                  70                  75                  80

Ala Lys Val Lys Ala Ile Trp Gly Thr Lys Cys Ser Lys Trp Ala Asp
                85                  90                  95

Ser Gly Arg Phe Tyr Pro Phe Leu Asp Thr Gln Ile Gly Pro Pro Glu
            100                 105                 110

Val Ala Leu Thr Thr Asp Glu Lys Ser Ile Ser Val Val Leu Thr Ala
            115                 120                 125

Pro Glu Lys Trp Lys Arg Asn Pro Asp Asp Leu Pro Val Ser Met Gln
130                 135                 140

Gln Ile Tyr Ser Asn Leu Lys Tyr Asn Val Ser Val Leu Asn Thr Lys
145                 150                 155                 160

Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
            180                 185                 190

Val Pro Gly Pro Pro Arg Arg Ala Gln Pro Ser Glu Lys Gln Cys Ala
            195                 200                 205

Arg Thr Leu Lys Asp Gln Ser Ser Glu Phe Lys Ala Lys
        210                 215                 220

(2) INFORMATION FOR SEQ ID NO:59:

(i) SEQUENCE CHARACTERISTICS:
        (A) LENGTH: 663 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...663
        (D) OTHER INFORMATION:

(xi) SEQUENCE DESCRIPTION: SEQ ID NO:59:

GTT CCC TGT GTC TCT GGT GGT TTG CCT AAA CCT GCA AAC ATC ACC TTC     48
Val Pro Cys Val Ser Gly Gly Leu Pro Lys Pro Ala Asn Ile Thr Phe
 1               5                  10                  15

TTA TCC ATC AAC ATG AAG AAT GTC CTA AAC TGG ACT CCA CCA GAG GGT     96
Leu Ser Ile Asn Met Lys Asn Val Leu Asn Trp Thr Pro Pro Glu Gly
                20                  25                  30

CTT AAC GGA GTT AAA GTT ACT TAC ACT GTG CAG TAT TTC ATA TAT GGG    144
Leu Asn Gly Val Lys Val Thr Tyr Thr Val Gln Tyr Phe Ile Tyr Gly
            35                  40                  45

AAC AAG AAA TGG CTG AAT AAA TCA GAA TGC AGA AAT ATC AAT AGA ACC    192
Asn Lys Lys Trp Leu Asn Lys Ser Glu Cys Arg Asn Ile Asn Arg Thr
 50                  55                  60

TAC TGT GAT CTT TCT GCT GAA ACT TCT GAC TAC GAA CAC CAG TAT TAT    240
Tyr Cys Asp Leu Ser Ala Glu Thr Ser Asp Tyr Glu His Gln Tyr Tyr
 65                  70                  75                  80
```

```
GCC AAA GTT AAG GCC ATT TGG GGA ACA AAG TGT TCC AAA TGG GCT GAA      288
Ala Lys Val Lys Ala Ile Trp Gly Thr Lys Cys Ser Lys Trp Ala Glu
             85                  90                  95

AGT GGA CGG TTC TAT CCT TTT TTA GAA ACA AAC ATT GGC CCA CCA GAG      336
Ser Gly Arg Phe Tyr Pro Phe Leu Glu Thr Asn Ile Gly Pro Pro Glu
            100                 105                 110

GTG GCA CTG ACT ACA GAT GAG AAG TCC ATT TCT GTT GTC CTG ACA GCT      384
Val Ala Leu Thr Thr Asp Glu Lys Ser Ile Ser Val Val Leu Thr Ala
            115                 120                 125

CCA GAG AAG TGG AAG AGA AAT CCA GAA GAC CTT CCT GTT TCC ATG AAC      432
Pro Glu Lys Trp Lys Arg Asn Pro Glu Asp Leu Pro Val Ser Met Asn
130                 135                 140

AAC ATA TAC TCC AAT CTG AAG TAT AAC GTG TCT GTG TTG AAT ACT AAA      480
Asn Ile Tyr Ser Asn Leu Lys Tyr Asn Val Ser Val Leu Asn Thr Lys
145                 150                 155                 160

TCA AAC AGA ACG TGG TCC CAG TGT GTG ACC AAC CAC ACG CTG GTG CTC      528
Ser Asn Arg Thr Trp Ser Gln Cys Val Thr Asn His Thr Leu Val Leu
            165                 170                 175

ACC TGG CTG GAG CCG AAC ACT CTT TAC TGC GTA CAC GTG GAG TCC TTC      576
Thr Trp Leu Glu Pro Asn Thr Leu Tyr Cys Val His Val Glu Ser Phe
            180                 185                 190

GTC CCA GGG CCC CCT CGC CGT GCT CAG CCT TCT GAG AAG CAG TGT GCC      624
Val Pro Gly Pro Pro Arg Arg Ala Gln Pro Ser Glu Lys Gln Cys Ala
            195                 200                 205

AGG ACT TTG AAA GAT AAC TCA TCA GAG TTC AAG GCT AAA                  663
Arg Thr Leu Lys Asp Asn Ser Ser Glu Phe Lys Ala Lys
210                 215                 220

(2) INFORMATION FOR SEQ ID NO:60:

(i) SEQUENCE CHARACTERISTICS:
        (A) LENGTH: 221 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:60:

Val Pro Cys Val Ser Gly Gly Leu Pro Lys Pro Ala Asn Ile Thr Phe
1               5                   10                  15

Leu Ser Ile Asn Met Lys Asn Val Leu Asn Trp Thr Pro Pro Glu Gly
            20                  25                  30

Leu Asn Gly Val Lys Val Thr Tyr Thr Val Gln Tyr Phe Ile Tyr Gly
            35                  40                  45

Asn Lys Lys Trp Leu Asn Lys Ser Glu Cys Arg Asn Ile Asn Arg Thr
50                  55                  60

Tyr Cys Asp Leu Ser Ala Glu Thr Ser Asp Tyr Glu His Gln Tyr Tyr
65                  70                  75                  80

Ala Lys Val Lys Ala Ile Trp Gly Thr Lys Cys Ser Lys Trp Ala Glu
            85                  90                  95

Ser Gly Arg Phe Tyr Pro Phe Leu Glu Thr Asn Ile Gly Pro Pro Glu
            100                 105                 110

Val Ala Leu Thr Thr Asp Glu Lys Ser Ile Ser Val Val Leu Thr Ala
            115                 120                 125

Pro Glu Lys Trp Lys Arg Asn Pro Glu Asp Leu Pro Val Ser Met Asn
            130                 135                 140

Asn Ile Tyr Ser Asn Leu Lys Tyr Asn Val Ser Val Leu Asn Thr Lys
145                 150                 155                 160
```

```
Ser Asn Arg Thr Trp Ser Gln Cys Val Thr Asn His Thr Leu Val Leu
                165                 170                 175

Thr Trp Leu Glu Pro Asn Thr Leu Tyr Cys Val His Val Glu Ser Phe
                180                 185                 190

Val Pro Gly Pro Pro Arg Arg Ala Gln Pro Ser Glu Lys Gln Cys Ala
            195                 200                 205

Arg Thr Leu Lys Asp Asn Ser Ser Glu Phe Lys Ala Lys
    210                 215                 220
```